United States Patent
Kao et al.

(10) Patent No.: US 12,251,272 B2
(45) Date of Patent: Mar. 18, 2025

(54) SYSTEMS AND METHODS FOR OPTOGENETIC IMAGING USING SEMI-KINEMATIC COUPLING

(71) Applicant: INSCOPIX, INC., Palo Alto, CA (US)

(72) Inventors: Kelvin Kao, Mountain View, CA (US); David Pignatelli, Saratoga, CA (US); Mark O. Trulson, San Jose, CA (US); Alice Stamatakis, Mountain View, CA (US); Koen Visscher, Tucson, AR (US)

(73) Assignee: INSCOPIX, INC., Mountain View, CA (US)

( * ) Notice: Subject to any disclaimer, the term of this patent is extended or adjusted under 35 U.S.C. 154(b) by 240 days.

(21) Appl. No.: 17/843,819

(22) Filed: Jun. 17, 2022

(65) Prior Publication Data
US 2022/0387127 A1 Dec. 8, 2022

Related U.S. Application Data

(63) Continuation-in-part of application No. 17/484,791, filed on Sep. 24, 2021, now Pat. No. 11,690,696, (Continued)

(51) Int. Cl.
*A61B 90/20* (2016.01)
*A61B 5/00* (2006.01)
(Continued)

(52) U.S. Cl.
CPC ............ *A61B 90/20* (2016.02); *A61B 5/0059* (2013.01); *A61B 5/0071* (2013.01);
(Continued)

(58) Field of Classification Search
None
See application file for complete search history.

(56) References Cited

U.S. PATENT DOCUMENTS

| | | |
|---|---|---|
| 5,736,410 A | 4/1998 | Zarling et al. |
| 6,072,622 A | 6/2000 | Biber et al. |

(Continued)

FOREIGN PATENT DOCUMENTS

| | | |
|---|---|---|
| CN | 1668913 A | 9/2005 |
| CN | 101116023 A | 1/2008 |

(Continued)

OTHER PUBLICATIONS

Co-pending U.S. Appl. No. 15/331,549, inventors Trulson; Mark O. et al., filed Oct. 21, 2016.

(Continued)

*Primary Examiner* — Eileen M Adams
(74) *Attorney, Agent, or Firm* — Quarles & Brady LLP; Yakov Sidorin

(57) ABSTRACT

Provided herein are systems and methods for imaging using a microscope system comprising removeable or replaceable component parts. Such systems and methods employ semi-kinetic coupling for easy, tool-free attachment of the microscope system to a baseplate. Systems and methods provided herein may comprise simultaneous imaging and stimulation using a microscope system. The microscope system can have a relatively small size compared to an average microscope system.

20 Claims, 27 Drawing Sheets

Related U.S. Application Data which is a continuation of application No. 16/851,678, filed on Apr. 17, 2020, now Pat. No. 11,197,735, which is a continuation of application No. 15/964,832, filed on Apr. 27, 2018, now Pat. No. 10,682,197, which is a continuation of application No. PCT/US2016/060717, filed on Nov. 4, 2016.

(60) Provisional application No. 62/383,122, filed on Sep. 2, 2016, provisional application No. 62/251,501, filed on Nov. 5, 2015.

(51) Int. Cl.

| | | |
|---|---|---|
| *G01N 21/64* | (2006.01) | |
| *G02B 21/00* | (2006.01) | |
| *G02B 21/02* | (2006.01) | |
| *G02B 21/06* | (2006.01) | |
| *G02B 21/16* | (2006.01) | |
| *G02B 21/32* | (2006.01) | |
| *A61B 5/24* | (2021.01) | |
| *G01Q 10/00* | (2010.01) | |
| *G02B 3/14* | (2006.01) | |
| *G02B 21/24* | (2006.01) | |

(52) U.S. Cl.
CPC ....... *A61B 5/4064* (2013.01); *G01N 21/6458* (2013.01); *G02B 21/0004* (2013.01); *G02B 21/0096* (2013.01); *G02B 21/025* (2013.01); *G02B 21/06* (2013.01); *G02B 21/16* (2013.01); *G02B 21/32* (2013.01); *A61B 5/0035* (2013.01); *A61B 5/24* (2021.01); *G01N 2021/6439* (2013.01); *G01N 2021/6441* (2013.01); *G01Q 10/00* (2013.01); *G02B 3/14* (2013.01); *G02B 21/242* (2013.01)

(56) References Cited

U.S. PATENT DOCUMENTS

| | | | |
|---|---|---|---|
| 7,511,891 | B2 | 3/2009 | Messerschmidt |
| 8,346,346 | B1 | 1/2013 | Schnitzer et al. |
| 8,624,967 | B2 | 1/2014 | O'Connell et al. |
| 8,696,722 | B2 | 4/2014 | Lee et al. |
| 8,788,021 | B1 | 7/2014 | Flusberg et al. |
| 9,161,694 | B2 | 10/2015 | Schnitzer et al. |
| 9,195,043 | B2 | 11/2015 | Ghosh et al. |
| 9,474,448 | B2 | 10/2016 | Ghosh et al. |
| 9,498,135 | B2 | 11/2016 | Ghosh et al. |
| 9,629,554 | B2 | 4/2017 | Ghosh et al. |
| 9,636,020 | B2 | 5/2017 | Flusberg et al. |
| 9,839,361 | B2 | 12/2017 | Schnitzer et al. |
| 10,200,657 | B2 | 2/2019 | Ghosh |
| 10,386,623 | B2 | 8/2019 | Visscher et al. |
| 10,682,197 | B2 | 6/2020 | Trulson et al. |
| 10,813,552 | B2 | 10/2020 | Ghosh et al. |
| 10,908,405 | B2 | 2/2021 | Trulson et al. |
| 2003/0037953 | A1* | 2/2003 | Sarkinen ............... G02B 6/4452 174/72 R |
| 2004/0184660 | A1 | 9/2004 | Treado et al. |
| 2005/0094260 | A1 | 5/2005 | Tokuda et al. |
| 2006/0210962 | A1 | 9/2006 | Imaizumi et al. |
| 2007/0109634 | A1 | 5/2007 | Araki et al. |
| 2007/0253057 | A1 | 11/2007 | Potsaid et al. |
| 2009/0201577 | A1 | 8/2009 | Laplante et al. |
| 2010/0073669 | A1* | 3/2010 | Colvin, Jr. ............ G01J 3/0256 356/218 |
| 2010/0309547 | A1 | 12/2010 | Hirata et al. |
| 2011/0127405 | A1* | 6/2011 | Grossman .......... G02B 21/0032 250/492.1 |
| 2011/0242649 | A1 | 10/2011 | Murayama |
| 2011/0282331 | A1 | 11/2011 | Brennan et al. |
| 2012/0062723 | A1 | 3/2012 | Ghosh et al. |
| 2012/0105949 | A1 | 5/2012 | Cummings et al. |
| 2012/0281211 | A1 | 11/2012 | Murugkar et al. |
| 2013/0087517 | A1* | 4/2013 | Zhong ................. F16M 11/105 211/26 |
| 2013/0260382 | A1* | 10/2013 | Ghosh .................... G02B 21/33 435/6.12 |
| 2014/0043462 | A1 | 2/2014 | Ghosh et al. |
| 2014/0046408 | A1 | 2/2014 | Shoham et al. |
| 2015/0087902 | A1 | 3/2015 | Mertz et al. |
| 2015/0116812 | A1 | 4/2015 | Matsumoto et al. |
| 2015/0148615 | A1 | 5/2015 | Brennan et al. |
| 2015/0309295 | A1* | 10/2015 | Cocker ............... G02B 21/362 600/476 |
| 2016/0022148 | A1 | 1/2016 | Mark et al. |
| 2016/0183782 | A1 | 6/2016 | Yu et al. |
| 2018/0136446 | A1 | 5/2018 | Werley et al. |
| 2018/0177401 | A1 | 6/2018 | Yang et al. |
| 2018/0217364 | A1 | 8/2018 | Cocker et al. |
| 2018/0220106 | A1 | 8/2018 | Ghosh |
| 2018/0296074 | A1 | 10/2018 | Trulson et al. |
| 2018/0303573 | A1 | 10/2018 | Trulson et al. |
| 2019/0133449 | A1 | 5/2019 | Flusberg et al. |
| 2019/0133453 | A1 | 5/2019 | Schnitzer et al. |
| 2019/0356884 | A1 | 11/2019 | Ghosh |
| 2020/0057290 | A1 | 2/2020 | Visscher et al. |
| 2021/0029329 | A1 | 1/2021 | Ghosh |
| 2021/0059578 | A1 | 3/2021 | Nassi et al. |
| 2021/0059782 | A1 | 3/2021 | Trulson et al. |
| 2021/0141204 | A1 | 5/2021 | Visscher et al. |
| 2021/0247603 | A1 | 8/2021 | Trulson et al. |

FOREIGN PATENT DOCUMENTS

| | | |
|---|---|---|
| CN | 102003936 A | 4/2011 |
| CN | 102540446 A | 7/2012 |
| CN | 103097809 A | 5/2013 |
| CN | 103513411 A | 1/2014 |
| JP | 2001183524 A | 7/2001 |
| JP | 2001238229 A | 8/2001 |
| JP | 2005173487 A | 6/2005 |
| JP | 2005321753 A | 11/2005 |
| JP | 2006091506 A | 4/2006 |
| JP | 2006154230 A | 6/2006 |
| JP | 4125609 B2 | 7/2008 |
| JP | 2009175486 A | 8/2009 |
| JP | 2009528577 A | 8/2009 |
| JP | 2013545116 A | 12/2013 |
| WO | 9202839 A1 | 2/1992 |
| WO | 9729709 A1 | 8/1997 |
| WO | 2012026379 A1 | 3/2012 |
| WO | 2013157606 A1 | 10/2013 |
| WO | 2013172085 A1 | 11/2013 |
| WO | 2014057774 A1 | 4/2014 |
| WO | 2014071390 A1 | 5/2014 |
| WO | 2015087824 A1 | 6/2015 |

OTHER PUBLICATIONS

Co-pending U.S. Appl. No. 15/403,819, inventor Ghosh; Kunal, filed Jan. 11, 2017.
Co-pending U.S. Appl. No. 15/443,999, inventors Flusberg; Benjamin A. et al., filed Feb. 27, 2017.
Co-pending U.S. Appl. No. 15/727,317, inventors Flusberg; Benjamin A. et al., filed Oct. 6, 2017.
Co-pending U.S. Appl. No. 15/830,894, inventors Schnitzer; Mark J. et al., filed Dec. 4, 2017.
Co-pending U.S. Appl. No. 17/080,295, inventors Ghosh; Kunal et al., filed Oct. 26, 2020.
Co-pending U.S. Appl. No. 17/316,394, inventor Ghoshkunal, filed May 10, 2021.
Co-pending U.S. Appl. No. 17/481,123, inventors Visscherkoen et al., filed Sep. 21, 2021.
EP16843147.6 European Search Report dated Jun. 17, 2019.
EP16843147.6 European Search Report dated Mar. 8, 2019.
EP16863123.2 European Examination report dated Feb. 20, 2020.
EP16863123.2 Extended European Search Report dated Apr. 25, 2019.

(56) References Cited

OTHER PUBLICATIONS

Erdogan, T., Optical filters for wavelength selection in fluorescence instrumentation. Current Protocols in Cytometry, Apr. 1, 2011; pp. 2.4.1-2.4.25.
Grintech. High-NA Endomicroscopic Imaging Objective now available as achromatic version. Rev. Dec. 2013. 1 page.
International Search Report and Written Opinion dated Jan. 13, 2017 for International PCT Patent Application No. PCT/US2016/050277.
International Search Report and Written Opinion dated Jan. 19, 2017 for International PCT Patent Application No. PCT/US2016/060717.
Leigh, et al. Multi-color miniature dual-axis confocal microscope for point-of-care pathology. Opt Lett. Jun. 15, 2012;37(12):2430-2. doi: 10.1364/OL.37.002430.
Liu Riu et al., Extendable, miniaturized multi-modal optical imaging system: cortical hemodynamic observation in freely moving animals. Optics Express, Jan. 28, 2013, vol. 21, No. 2, pp. 1911-1924.
Martin, Paul R. Rheinberg Illumination: A Fresh Approach to High Magnification Color Contrast. Aug. 26, 2014. Available at https://www.mccrone.com/mm/rheinberg-illumination-afresh-approach-to-high-magnification-color-contrast.
Murari, et al., An integrated imaging microscope for untethered cortical imaging in freelymoving animals. EIEE in medicine and biology, 201 O; 5795-5798.
Murari, et al., Design and characterization of a miniaturized Epi-illuminated microscope. EIEE in medicine and biology, 2009; 5369-5372.
Pellett, et al. Two-color STED microscopy in living cells. Biomed Opt Express. Aug. 1, 2011 ;2(8):2364-71. doi: 10.1364/BOE.2.002364. Epub Jul. 22, 2011.
U.S. Appl. No. 16/851,678 Notice of Allowance dated Aug. 12, 2021.
U.S. Appl. No. 15/256,296 Notice of Allowance dated Oct. 6, 2020.
U.S. Appl. No. 15/256,296 Office Action dated Apr. 3, 2020.
U.S. Appl. No. 15/256,296 Office Action dated Feb. 15, 2019.
U.S. Appl. No. 15/256,296 Office Action dated Nov. 18, 2019.
U.S. Appl. No. 15/964,832 Office Action dated Feb. 27, 2020.
U.S. Appl. No. 15/964,832 Office Action dated Sep. 9, 2019.
U.S. Appl. No. 16/851,678 Office Action dated May 4, 2021.

* cited by examiner

EX-LED = LED for excitation of calcium indicator
OG-LED = LED for activation of opsin

SYSTEMS AND METHODS FOR OPTOGENETIC IMAGING USING SEMI-KINEMATIC COUPLING

CROSS-REFERENCE

This application is a continuation-in-part of U.S. application Ser. No. 17/484,791, filed Sep. 24, 2021, which is a continuation of U.S. application Ser. No. 16/851,678, filed Apr. 17, 2020, which is a continuation of U.S. application Ser. No. 15/964,832, filed Apr. 27, 2018, which is a continuation of International Application No. PCT/US2016/060717, filed Nov. 4, 2016, which claims the benefit of U.S. Provisional Application No. 62/251,501, filed on Nov. 5, 2015, and U.S. Provisional Application No. 62/383,122, filed on Sep. 2, 2016, each of which is entirely incorporated herein by reference.

BACKGROUND

Biological samples can be stimulated by light energy. Stimulation can initiate, enhance, and/or inhibit one or more activities performed by a portion of the biological sample stimulated by the light energy. In some cases, nerve cells can be activated or deactivated by light energy. One or more populations of nerve cells can communicate signals based on activation by light energy. Biological samples can have small spatial scales such that they may comprise one or more features, such as cells, that are not visible to a human eye. Microscopes can be employed to visualize the small features of biological samples.

SUMMARY

Recognized herein is the need for small, lightweight, customizable and easily assembled imaging devices and systems.

An aspect of the invention relates to an imaging device, comprising: a baseplate; a device body; and a removeable and replaceable cable assembly, wherein the device body is connected and separated with the baseplate in a tools-free, reproducible manner. In some embodiments, an imaging device may be provided, comprising: a baseplate configured to be attached to a subject having a target region to be imaged; a removeable and replaceable cable assembly; and a device body having a sensor cap assembly comprising an image sensor configured to image the target region when the device body is connected to the baseplate, wherein the device body is configured to be connected to and separated from the baseplate in a reproducible manner. The removeable and replaceable cable assembly comprises cables and a cable PCBA and can connect to the sensor cap assembly. In an exemplary embodiment, the cable assembly comprises cable wires surrounded by heat shrink and having a threaded collar, O-ring, cable cap and cable PCBA with a header that plugs into a socket on the sensor cap assembly. The sensor cap assembly comprises a sensor cap made of a crystalline material (e.g., machined PEEK), which protects and covers sensitive electronics. To attach the cable assembly, the header on the cable assembly plugs into a socket on the sensor cap. The header can have a keyed profile, which helps guide its orientation, and a thumb nut on the cable assembly threads onto the sensor cap to lock the connection.

In some embodiments, the baseplate can comprise one or more subject attachment mechanism configured to attach the baseplate to the subject so that the base plate does not move relative to the target region. The baseplate and device body may comprise mating surfaces that can mechanically prevent at least one of rotational movement or axial movement between the base plate and the device body when the device body is connected to the baseplate. Optionally, the device body comprises one or more grooves complementary to one or more bumps in the baseplate, such that the device body is configured to be connected to and separated from the baseplate via kinematic coupling of the device body and the baseplate. The one or more grooves may be positioned to cause the device body to snap to a particular alignment with the baseplate.

In some embodiments, the one or more bumps are evenly spaced. For example, the baseplate may have four bumps, which are spaced 90 degrees apart. The baseplate may have three bumps, which are spaced 120 degrees apart. The one or more bumps may comprise partial-cylinder bumps. The one or more bumps may also comprise partial-sphere bumps.

In some embodiments of the miniature imaging device, the device body comprises outer spring clips, such that the device body is secured to the baseplate through compression and release of the spring clips. In some cases, the spring clips comprise bent sheet metal clips. In some cases, the spring clips comprise molded plastic clips.

In some embodiments of the present disclosure, the cable assembly comprises: a cable PCBA, a cap covering cable wires soldered to the cable PCBA, and a threaded collar. In such an embodiment, the threaded collar has an O-ring located inside of it, and the threaded collar slides down such that the O ring compresses against the cap to connect the cable assembly and the sensor cap assembly.

In some embodiment, the baseplate comprises shelf-like features (also referred to, interchangeably, as shelf features or ledges). In some cases, the shelf-like features protrude from a plurality of edges of the baseplate. In some cases, the shelf-like features protrude from at least two edges of the baseplate. In some cases, the shelf-like features protrude from four edges of the baseplate. In some cases, the imaging device further comprises a sensor cap assembly having an image sensor and a socket, wherein a header on the cable assembly plugs into the socket.

In some embodiments, the device body has a volume of 10 cubic centimeters or less. The base plate may have a maximum dimension of 3 cm or less. In some instances the device body weighs less than 3 grams. In some instances the device body weighs less than 2 grams.

The device body may have a housing containing one or more optical elements along an image collection pathway from the target region to the sensor cap assembly. In some embodiments, the base plate may have a hole and the device body may have an objective lens configured fit at least partially through the hole to capture light from the target region when the device body is connected to the baseplate.

Further provided herein is an imaging device, comprising: a device body having a volume of 10 cubic centimeters or less, said device body comprising an image sensor configured to image a target region of a subject; a sensor cap assembly comprising one or more objective lenses disposed along an image collection pathway from the target region to the image sensor, wherein the sensor cap assembly is configured to be connected and separated with the device body in a reproducible manner.

In some embodiments, the device body is connected to and separated from a baseplate using spring clips. In some cases, the spring clips comprise upper tabs and lower tabs. The upper tabs and the lower tabs may be connected such that compressing the upper tabs will cause the lower tabs to move apart. Likewise, the upper tabs and the lower tabs may be connected such that releasing the upper tabs will cause the lower tabs to move together.

In some cases, the spring clips connect the device body to a baseplate which has shelf-like features that extend outward from edges of the baseplate. In such embodiments, the spring clips experience interference with the edges of the baseplate when the sensor assembly and the device body are in a docked position. In some embodiments of the present disclosure, the baseplate comprises a central tapered bore. In some cases, partial cylinder bumps located on the inside walls of the central tapered bore couple to V-grooves in the device body.

An additional aspect of the invention relates to an imaging device, comprising: one or more objectives; and a device body, wherein the one or more objectives are configured to be connected and separated with the device body in a reproducible manner. Aspects of the invention may include an imaging device, comprising: a device body having a volume of 10 cubic centimeters or less, said device body comprising a sensor assembly comprising an image sensor configured to image a target region of a subject; and one or more objective lenses disposed along an image collection pathway from the target region to the image sensor, wherein the one or more objective lenses are configured to be connected and separated with the device body in a reproducible manner using spring clips. In such an embodiment, the spring clips may comprise upper tabs and lower tabs. In some cases, the upper tabs and the lower tabs are connected such that compressing the upper tabs will cause the lower tabs to move apart. In some cases, the upper tabs and the lower tabs are connected such that releasing the upper tabs will cause the lower tabs to move together. In some embodiments, the spring clips connect the device body to a baseplate which has shelf-like features that extend outward from edges of the baseplate. In embodiments of the present invention, the spring clips experience interference with the edges of the baseplate when the sensor cap assembly and the device body are in a docked position. In some cases, the imaging device has a baseplate having partial cylinder bumps which couple to V-grooves in the device body.

In some cases, the imaging device further comprises one or more objective mounts for holding and mounting said one or more objective lenses to the device body in a predetermined orientation with respect to the device body. The one or more objective mounts aid in attachment and alignment of the one or more objective lenses to the device body. In some cases, the imaging device is configured to accept a plurality of objective lenses having different field of view or resolution characteristics with aid of the one or more objective mounts.

In some embodiments of the present disclosure, the device body of the imaging device has a housing containing an illumination source within the housing, configured to provide illumination to the target region via an illumination pathway. The one or more objective lenses may be configured to be positioned less than 5 mm away from the target region and provide a focused image to be captured by the image sensor.

In any of the above embodiments of the imaging device described herein, the greatest dimension of the device body may be, for example, less than 20 mm. In some cases, the imaging device weighs less than 2 grams.

In any of the above embodiments, the sensor cap assembly may comprise a sensor cap comprising machined PEEK housing. The sensor cap assembly may further comprise a sensor printed circuit board assembly (PCBA) with a molded elastomeric Z-connector. In some embodiments, the sensor cap assembly further comprises a carrier PCBA gasket.

The imaging devices disclosed herein may have a sensor cap assembly that comprises a sensor Printed Circuit Board Assembly (PCBA) with a molded elastomeric Z-connector; a carrier PCBA; foam tape; a carrier PCBA gasket, and a sensor cap. The foam tape may be, for example, very high bond (VHB) foam tape. The sensor cap may comprise semicrystalline material, such as machined PEEK. In some cases, this sensor cap is configured to connect to a cable assembly. For example, in some embodiment, the sensor cap is connected to the cable assembly via a thumb-nut located on a cable assembly.

Additionally, one or more objective mounts may be provided for holding and mounting said one or more objective lenses to the device body in a predetermined orientation with respect to the device body. The one or more objective mounts may aid in attachment and alignment of the one or more objective lenses to the device body. The imaging device may be configured to accept a plurality of objective lenses having different field of view or resolution characteristics with aid of the one or more objective mounts.

The device body may have a housing containing an illumination source within the housing, configured to provide illumination to the target region via an illumination pathway. The objective lens may be configured to be positioned less than 5 mm away from the target region and provide a focused image to be captured by the image sensor. In some embodiments, a greatest dimension of the device body may be less than 20 mm. Optionally, the imaging device may weigh less than 2 grams.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

Further provided herein are systems and methods for simultaneously imaging a magnified sample and stimulating at least a fraction of the sample using a microscope comprising a sensor cap assembly and a removable cable assembly. The imaging and stimulation can be performed with a microscope system having a microscope which kinematically couples to a baseplate. Upon kinematic coupling, microscope registration is performed. The microscope system can include a small microscope with a total volume of less than one cubic inch. The microscope can comprise a stimulation light source and an imaging light source. The stimulation light source can be incident on a smaller area than an area on which the imaging light is incident. The microscope system can deliver imaging light at a relatively lower intensity compared to the stimulation light. The wave properties (e.g., wavelength, frequency, intensity, and power) of the imaging light and the stimulation light can be modulated to reduce cross talk between the imaging and stimulation light.

Thus, in one aspect, a microscope system for simultaneous imaging and stimulation is provided. The system comprises: an imaging light directing arrangement that directs imaging light from an imaging light source to a sample in a field-of-view of the microscope system; a stimulation light directing arrangement that directs stimulation light from a stimulation light source to at least a portion of the sample for stimulation of the portion of the sample while the sample is illuminated by the imaging light from the imaging directing arrangement; an optical path that directs the imaging light and the stimulation light to the sample, wherein the imaging light and the stimulation light are transmitted through at least one shared optical element in the optical path and wherein the stimulation light overlaps the imaging light at the sample; and an image sensor that receives emitted light from the sample to generate an image of the sample while stimulation light is directed to the portion of the sample for stimulation of the portion of the sample.

In some embodiments, the stimulation light source comprises (1) a single stimulation light source that is patterned by a spatial light modulator, or (2) a plurality of stimulation light sources. In some embodiments, (1) the patterned stimulation light is spatially or temporally modulated, or (2) wherein at least a fraction of the plurality of stimulation light sources are turned on when the stimulation light directing arrangement directs stimulation light to the portion of the sample. In some embodiments, (1) the patterned stimulation light is spatially or temporally modulated based on a command to direct stimulation light to a specified portion of the sample, or (2) wherein the fraction of the plurality of stimulation light sources that are turned on is based on a command to direct stimulation light to a specified portion of the sample. In some embodiments, the patterned stimulation light or the plurality of stimulation light sources are controlled by a computer system that performs image analysis on an image generated by the image sensor. In some embodiments, image analysis determines a location of one or more objects of interest in the sample. In some embodiments, the imaging light and the stimulation light are delivered to the sample through a same optical path. In some embodiments, the same optical path that directs the imaging light and the stimulation light to the sample comprises an optical probe that (1) facilitates delivery of the imaging light and the stimulation light to the sample, and (2) facilitates relay of the sample's image to the image sensor. In some embodiments, the computer system controls an illumination pattern of the stimulation light source with the aid of one or more processors based on the image analysis on the image generated by the image sensor. In some embodiments, the microscope has a volume of about 1 cubic inch. In some embodiments, the microscope is mounted on a freely moving organism. In some embodiments, the sample comprises brain tissue. In some embodiments, a power density of the stimulation light is at least 10× a power density of the imaging light. In some embodiments, a wavelength range of the stimulation light is spectrally separated from a wavelength range of the imaging light by at least 10 nm. In some embodiments, the image sensor that receives emitted light from the sample generates an image of the sample with a spatial resolution of at least 50 µm or better. In some embodiments, the imaging light directing arrangement is in optical communication with a light source that is off board the microscope system. In some embodiments, the stimulation light directing arrangement is in optical communication with a light source that is off board the microscope system.

In another aspect, a method for simultaneous imaging and stimulating a sample with a microscope is provided. The method comprises: directing imaging light with aid of an imaging light directing arrangement that directs imaging light from an imaging light source to at a least a portion of the sample in a field-of-view of the microscope, wherein the imaging light has a wavelength within an ultraviolet, visible, or near infrared wavelength spectrum; generating an image of the sample with aid of an image sensor of the microscope that receives emitted light from the sample to generate the image of the sample; and directing stimulation light with aid of a stimulation light directing arrangement that directs stimulation light from a stimulation light source to the portion of the sample for stimulation of the portion of the sample while the sample is illuminated by the imaging light from the imaging directing arrangement.

In some embodiments, the stimulation light source comprises a single light source that is patterned by a spatial light modulator or wherein the stimulation light source comprises a plurality of spatially distinct stimulation light sources. In some embodiments, the method further comprises (1) temporally or spatially modulating the patterned stimulation light source, or (2) turning on at least a fraction of the plurality of stimulation light sources to direct the stimulation light to the portion of the sample. In some embodiments, the patterned stimulation light source is spatially or temporally modulated based on a command to direct stimulation light to a specified portion of the sample, or wherein the fraction of the plurality of stimulation light sources that are turned on is based on a command to direct stimulation light to a specified portion of the sample. In some embodiments, the method further comprises analyzing the image of the sample by one or more processors of a computer system and controlling the patterned stimulation light source or the plurality of stimulation light sources based on analysis of the image of the sample. In some embodiments, the analysis of the image includes determining a location of one or more objects of interest in the sample. In some embodiments, the imaging light and the stimulation light are delivered to the sample through a same optical path. In some embodiments, the same optical path that simultaneously directs the imaging light and the stimulation light to the sample comprises an optical probe that (1) facilitates delivery of the imaging light and the stimulation light to the sample, and (2) facilitates relay of the object's image to the image sensor. In some embodiments, the microscope has a volume of about 1 cubic inch. In some embodiments, the microscope is mounted on a freely moving organism. In some embodiments, the sample comprises brain tissue. In some embodiments, a power density of the stimulation light is at least 10× a power density of the imaging light. In some embodiments, a wavelength range of the stimulation light is spectrally separated from a wavelength range of the imaging light by at least 10 nm. In some embodiments, the image sensor that receives emitted light from the sample generates an image of the sample with a spatial resolution of at least 20 µm.

In another aspect, a microscope system for simultaneous imaging and stimulation is provided. The system comprises: an imaging light directing arrangement that directs imaging light from an imaging light source to a sample in a field-of-view of the microscope system; a stimulation light directing arrangement that directs stimulation light from a stimulation light source to a different portion of the sample outside of the field-of-view for stimulation of the different portion of the sample while the sample is illuminated by the imaging light from the imaging directing arrangement; and an image sensor that receives emitted light from the sample to generate an image of the sample while stimulation light is directed to the different portion of the sample for stimulation of the different portion of the sample.

In some embodiments, the stimulation light source comprises (1) a single stimulation light source that is patterned by a spatial light modulator, or (2) a plurality of stimulation light sources. In some embodiments, (1) the patterned stimulation light is spatially or temporally modulated, or (2) wherein at least a fraction of the plurality of stimulation light sources are turned on when the stimulation light directing arrangement directs stimulation light to the different portion of the sample. In some embodiments, (1) the patterned stimulation light is spatially or temporally modulated based on a command to direct stimulation light to a specified portion of the sample, or (2) wherein the fraction of the plurality of stimulation light sources that are turned on is based on a command to direct stimulation light to a specified portion of the sample. In some embodiments, the patterned stimulation light or the plurality of stimulation light sources are controlled by a computer system that performs image analysis on an image generated by the image sensor. In some embodiments, image analysis determines a location of one or more objects of interest in the sample. In some embodiments, the imaging light and the stimulation light are delivered to the sample through different optical paths. In some embodiments, at least one of the optical paths comprises an optical probe that (1) facilitates delivery of the imaging light or the stimulation light to the sample, and (2) facilitates relay of the sample's image to the image sensor. In some embodiments, the computer system controls an illumination pattern of the stimulation light source with the aid of one or more processors based on the image analysis on the image generated by the image sensor. In some embodiments, the microscope has a volume of about 1 cubic inch. In some embodiments, the microscope is mounted on a freely moving organism. In some embodiments, the sample comprises brain tissue. In some embodiments, a power density of the stimulation light is at least 10× a power density of the imaging light. In some embodiments, a wavelength range of the stimulation light is spectrally separated from a wavelength range of the imaging light by at least 10 nm. In some embodiments, wherein the image sensor that receives emitted light from the sample generates an image of the sample with a spatial resolution of at least 50 µm or better. In some embodiments, the imaging light directing arrangement is in optical communication with a light source that is off board the microscope system. In some embodiments, the stimulation light directing arrangement is in optical communication with a light source that is off board the microscope system. In some embodiments, the field-of-view is an imaging field-of-view. In some embodiments, the stimulation light does not overlap the imaging light at the sample.

Disclosed herein are optical systems for simultaneous imaging and stimulation of tissue within a subject, the system comprising: a) an optical assembly comprising: i) an imaging light source comprising one or more light-emitting elements and configured to direct imaging light to tissue within a specified field-of-view; ii) a stimulation light source comprising one or more light-emitting elements and configured to direct stimulation light to tissue within at least a portion of said field-of-view; iii) at least a portion of an imaging optical path that directs the imaging light and the stimulation light to the tissue, wherein the imaging light and the stimulation light are transmitted to the tissue through at least one shared deformable lens; and iv) an image sensor configured to receive light that is reflected, scattered, or emitted by the tissue to generate an image of the tissue within said field-of-view, wherein the optical assembly connects to the sensor cap to form the device body; and b) a baseplate comprising shelf-like external features, wherein the baseplate is configured to be mounted on the subject in a fixed position and to receive the optical assembly in a fixed position, thereby aligning the optical assembly relative to the tissue of the subject upon attachment to the baseplate, wherein the sensor cap and the optical assembly are connected to form the device body, and wherein the device body is removable from the baseplate.

In some embodiments, the illumination optical path and the optical path are packaged in the housing. In some embodiment, the baseplate and the housing connect via a spring-clip mechanism. the field-of-view is about 1 mm×1 mm. In some embodiments, the focal plane of said image is adjustable over a range of about 300 µm without loss of spatial resolution. In some embodiments, the optical assembly is capable of generating images over a tissue volume of about 1 mm×1 mm×300 µm. In some embodiments, the optical assembly is capable of generating images with a spatial resolution of better than 2 µm at the center of the field-of-view. In some embodiments, the optical assembly further comprises one or more corrective optical elements and is capable of generating images with a spatial resolution of better than 2 µm over the entire field-of-view. In some embodiments, the optical assembly further comprises at least a second deformable lens. In some embodiments, the focal plane of said image is the same as the focal plane for stimulation light generated by said stimulation light source. In some embodiments, the focal plane of said image is different from the focal plane for stimulation light generated by said stimulation light source. In some embodiments, the at least one deformable lens is selected from the group consisting of liquid lenses, liquid crystal lenses, and piezo-actuated tunable lenses, or any combination thereof. In some embodiments, the at least one shared deformable lens is positioned in close proximity to a gradient index (GRIN) objective lens. In some embodiments, the at least one shared deformable lens is positioned in close proximity to the end of the gradient index (GRIN) objective lens that is farthest from the tissue. In some embodiments, the optical assembly further comprises a probe that may be partially implanted in the tissue. In some embodiments, the tissue-to-image sensor path length is less than about 5 cm. In some embodiments, the tissue-to-imaging light source path length is less than about 5 cm. In some embodiments, the imaging light source comprises two or more light-emitting elements, and is configured to direct imaging light of two or more different wavelengths to the tissue with the specified field-of-view. In some embodiments, the stimulation light source comprises two or more light-emitting elements, and is configured to direct stimulation light of two or more different wavelengths to the tissue within at least a portion of said field-of-view. In some embodiments, the stimulation light source is configured to direct stimulation light to the tissue in a user-defined spatial pattern. In some embodiments, the user-defined spatial pattern has a spatial resolution of better than 5 µm at the focal plane. In some embodiments, the optical system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and the software-encoded instructions comprise instructions for modulating the stimulation light in a time-dependent or spatially-dependent manner to induce a neurological response in said brain tissue. In some embodiments, the total volume of the system is less than about 5 cm³. In some embodiments, the total weight of the system is less than about 4 grams. In some embodiments, the system comprises at least a second optical assembly that may be mounted on the same baseplate. In some embodiments, the one or more light-emitting elements of the imaging light source or the stimulation light source comprise optical fibers that are coupled to one or more external light sources. In some embodiments, the system is mounted by means of said baseplate on a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are optical systems for simultaneous imaging and stimulation of tissue within a subject, the system comprising: an optical imaging probe comprising an imaging light source and an image sensor, and configured to receive light that is reflected, scattered, or emitted by the tissue to generate an image of the tissue within a specified field-of-view; an optical stimulation probe comprising one or more light-emitting elements and configured to direct stimulation light to tissue within said field-of-view, to tissue outside said field-of-view, or to any combination thereof; and a baseplate, wherein the baseplate is configured to be mounted on the subject in a fixed position and to receive the optical imaging and stimulation probes, thereby aligning the optical imaging and stimulation probes relative to the tissue of the subject upon attachment to the baseplate, and wherein the optical imaging and stimulation probes are removable from the baseplate.

In some embodiments, the optical system further comprises at least second optical imaging probe, at least a second optical stimulation probe, or any combination thereof attached to the same baseplate, and wherein the configuration of the baseplate determines the lateral distance between the optical imaging and optical stimulation probes. In some embodiments, the optical imaging probe(s) and optical stimulation probe(s) each comprise at least one deformable lens that permits adjustment of the focal plane over a range of about 300 µm without loss of spatial resolution. In some embodiments, the field-of-view of the optical imaging probe is about 1 mm×1 mm. In some embodiments, the optical imaging probe is capable of generating images over a tissue volume of about 1 mm×1 mm×300 µm. In some embodiments, the optical imaging probe is capable of generating images with a spatial resolution of better than 2 µm at the center of the field-of-view. In some embodiments, the optical imaging probe further comprises one or more corrective optical elements and is capable of generating images with a spatial resolution of better than 2 µm over the entire field-of-view. In some embodiments, the focal plane of said image is the same as the focal plane for stimulation light generated by said optical stimulation probe. In some embodiments, the focal plane of said image is different from the focal plane for stimulation light generated by said optical stimulation probe. In some embodiments, the at least one deformable lens is selected from the group consisting of liquid lenses, liquid crystal lenses, and piezo-actuated tunable lenses, or any combination thereof. In some embodiments, the at least one deformable lens of the optical imaging probe is positioned in close proximity to a gradient index (GRIN) objective lens. In some embodiments, the at least one deformable lens is positioned in close proximity to the end of the gradient index (GRIN) objective lens that is farthest from the tissue. In some embodiments, the optical imaging probe may be partially implanted in the tissue. In some embodiments, the optical stimulation probe may be partially implanted in the tissue. In some embodiments, the tissue-to-image sensor path length of the optical imaging probe is less than about 5 cm. In some embodiments, the tissue-to-imaging light source path length of the optical stimulation probe is less than about 5 cm. In some embodiments, the imaging light source comprises two or more light-emitting elements, and is configured to direct imaging light of two or more different wavelengths to the tissue with the specified field-of-view. In some embodiments, the optical stimulation probe comprises two or more light-emitting elements configured to direct stimulation light of two or more different wavelengths to the tissue within said field-of-view, to tissue outside said field-of-view, or to any combination thereof. In some embodiments, the optical stimulation probe is configured to direct stimulation light to the tissue in a user-defined spatial pattern. In some embodiments, the user-defined spatial pattern has a spatial resolution of better than 5 µm at the focal plane. In some embodiments, the optical system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and the software-encoded instructions comprise instructions for modulating the stimulation light in a time-dependent or spatially-dependent manner to induce a neurological response in said brain tissue. In some embodiments, the total volume of the system is less than about 5 cm³. In some embodiments, the total weight of the system is less than about 4 grams. In some embodiments, the imaging light source or the one or more light-emitting elements of the optical stimulation probe comprise optical fibers that are coupled to one or more external light sources. In some embodiments, the system is mounted by means of said baseplate on a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are optical systems for simultaneous imaging and stimulation of tissue within a subject, the system comprising: an optical assembly comprising: an optical imaging probe comprising an imaging light source and an image sensor, and configured to receive light that is reflected, scattered, or emitted by the tissue to generate an image of the tissue within a specified field-of-view; and an optical stimulation probe comprising one or more light-emitting elements and configured to direct stimulation light to tissue within said field-of-view, to tissue outside of said field-of-view, or to any combination thereof and a baseplate, wherein the baseplate is configured to be mounted on the subject in a fixed position and to receive the optical assembly, thereby aligning the optical assembly relative to the tissue of the subject upon attachment to the baseplate, and wherein the optical assembly has a total volume of less than about 5 cm$^3$ and is removable from the baseplate.

Also disclosed herein are optical systems for simultaneous imaging and stimulation of tissue within a subject, the system comprising: an optical assembly comprising: an optical imaging probe comprising an imaging light source, a deformable lens, and an image sensor, and configured to receive light that is reflected, scattered, or emitted by the tissue to generate a series of tomographic images of the tissue within a field-of-view of about 1 mm×1 mm over a depth of about 300 µm; and an optical stimulation probe comprising one or more light-emitting elements and configured to direct stimulation light to tissue within said field-of-view, to tissue outside of said field-of-view, or to any combination thereof; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly has a total volume of less than about 5 cm$^3$ and is removable from the baseplate.

In some embodiments, imaging light produced by the imaging light source and stimulation light are transmitted to the tissue through at least one shared deformable lens that permits adjustment of the focal plane over a range of about 300 µm without loss of spatial resolution. In some embodiments, the field-of-view of the optical imaging probe is about 1 mm×1 mm. In some embodiments, the optical imaging probe is capable of generating images over a tissue volume of about 1 mm×1 mm×300 µm. In some embodiments, the optical imaging probe is capable of generating images with a spatial resolution of better than 2 µm at the center of the field-of-view. In some embodiments, the optical imaging probe further comprises one or more corrective optical elements and is capable of generating images with a spatial resolution of better than 2 µm over the entire field-of-view. In some embodiments, the focal plane of said image is the same as the focal plane for stimulation light generated by said optical stimulation probe. In some embodiments, the focal plane of said image is different from the focal plane for stimulation light generated by said optical stimulation probe. In some embodiments, the at least one deformable lens is selected from the group consisting of liquid lenses, liquid crystal lenses, and piezo-actuated tunable lenses, or any combination thereof. In some embodiments, the at least one deformable lens of the optical imaging probe is positioned in close proximity to a gradient index (GRIN) objective lens. In some embodiments, the at least one deformable lens is positioned in close proximity to the end of the gradient index (GRIN) objective lens that is farthest from the tissue. In some embodiments, the optical imaging probe may be partially implanted in the tissue. In some embodiments, the optical stimulation probe may be partially implanted in the tissue. In some embodiments, the tissue-to-image sensor path length of the optical imaging probe is less than about 5 cm. In some embodiments, the tissue-to-imaging light source path length of the optical stimulation probe is less than about 5 cm. In some embodiments, the imaging light source comprises two or more light-emitting elements, and is configured to direct imaging light of two or more different peak wavelengths to the tissue with the specified field-of-view. In some embodiments, the optical stimulation probe comprises two or more light-emitting elements configured to direct stimulation light of two or more different peak wavelengths to the tissue within said field-of-view, to tissue outside said field-of-view, or to any combination thereof. In some embodiments, the optical stimulation probe is configured to direct stimulation light to the tissue in a user-defined spatial pattern. In some embodiments, the user-defined spatial pattern has a spatial resolution of better than 5 µm at the focal plane. In some embodiments, the optical system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and wherein the software-encoded instructions comprise instructions for modulating the stimulation light in a time-dependent or spatially-dependent manner to induce a neurological response in said brain tissue. In some embodiments, the total volume of the system is less than about 5 cm$^3$. In some embodiments, the total weight of the system is less than about 4 grams. In some embodiments, the imaging light source or the one or more light-emitting elements of the optical stimulation probe comprise optical fibers that are coupled to one or more external light sources. In some embodiments, the system is mounted by means of said baseplate on a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are optical systems for simultaneous imaging and stimulation of tissue within a subject, the system comprising: an optical assembly comprising: an illumination optical path comprising one or more light-emitting elements and configured to direct imaging light to tissue within a specified field-of-view; a stimulation optical path comprising one or more light-emitting elements and configured to direct stimulation light to tissue within said field-of-view, to tissue outside of said field-of-view, or to any combination thereof; an imaging optical path comprising one or more image sensors and configured to receive light reflected, scattered, or emitted by the tissue to generate an image of the tissue within said field-of-view; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly is removable from the baseplate.

Disclosed herein are optical systems for simultaneous imaging and stimulation of tissue within a subject, the system comprising: a) an optical assembly comprising: an illumination optical path comprising one or more light-emitting elements and configured to direct imaging light to tissue within a specified field-of-view; a stimulation optical path comprising one or more light-emitting elements and configured to direct stimulation light to tissue within said field-of-view, to tissue outside of said field-of-view, or to any combination thereof; an imaging optical path comprising one or more image sensors and configured to receive light reflected, scattered, or emitted by the tissue to generate an image of the tissue within said field-of-view; a wireless adapter configured to provide wireless communication of information or power between the optical assembly and an external controller; and a housing configured to enclose the optical assembly and wireless adapter, wherein the housing is hermetically-sealed and comprises a biocompatible outer surface; wherein the optical system is partially- or fully-implantable within the tissue of the subject.

In some embodiments, the specified field-of-view is of about 1 mm×1 mm. In some embodiments, the optical assembly is configured to acquire images with a spatial resolution of better than about 2 μm at the center of the field-of-view. In some embodiments, the optical assembly is configured to acquire images with a spatial resolution of better than about 2 μm over the entire field-of-view by means of adding one or more corrective optical elements to the optical assembly. In some embodiments, the optical assembly further comprises one or more deformable lenses configured to adjust the focal depth of the imaging optical path, the stimulation optical path, or both. In some embodiments, the one or more deformable lenses are configured to adjust the focal depth of the imaging optical path, the stimulation optical path, or both, over a range of about 300 μm without loss of spatial resolution. In some embodiments, the one or more deformable lenses are selected from the group consisting of liquid lenses, liquid crystal lenses, and piezo-actuated tunable lenses, or any combination thereof. In some embodiments, the one or more deformable lenses are configured so that the imaging optical path and the stimulation optical path direct light to the same focal plane. In some embodiments, the optical assembly is configured to acquire images over a tissue volume of about 1 mm×1 mm×300 μm. In some embodiments, the stimulation optical path is further configured to direct the stimulation light to the tissue in a user-defined spatial pattern. In some embodiments, the user-defined spatial pattern has a spatial resolution of better than about 5 μm at the focal plane. In some embodiments, the optical system further comprises a first processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and the software-encoded instructions comprise instructions for modulating the stimulation light in a time-dependent or spatially-dependent manner to induce a neurological response in said brain tissue. In some embodiments, the total volume of the system is less than about 5 cm$^3$. In some embodiments, the total weight of the system is less than about 4 grams. In some embodiments, the system comprises at least a second illumination optical path, at least a second stimulation optical path, at least a second imaging optical path, or any combination thereof. In some embodiments, the one or more light-emitting elements of the illumination optical path or the stimulation optical path comprise optical fibers that are coupled to one or more external light sources. In some embodiments, the baseplate is configured to allow attachment of two or more optical assemblies. In some embodiments, the wireless adapter is configured to provide wireless communication via a radio frequency or optical link. In some embodiments, the wireless adapter is configured to enable wireless read and write operations separately or simultaneously. In some embodiments, the system is mounted on, partially implanted within, or fully-implanted within a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are methods for simultaneous stimulation and imaging of tissue within a subject, the method comprising: providing an optical system according to any one of the embodiments disclosed herein; providing a subject comprising the tissue to be stimulated and imaged; mounting or implanting the optical system of step (a) on or within the subject; and generating one or more images of the tissue before, during, or after directing stimulation light to the tissue of said subject in a time-modulated or spatially-modulated manner.

In some embodiments, the subject is selected from the group consisting of mice, rats, cats, dogs, pigs, cows, horses, monkeys, chimpanzees, orangutans, gorillas, and humans. In some embodiments, the method is performed as part of preclinical research. In some embodiments, the method is performed as part of clinical research. In some embodiments, the method further comprises determining a clinical diagnostic test result. In some embodiments, the method further comprises directing stimulation light to the tissue in a time-modulated or spatially-modulated manner that produces a therapeutic effect.

Disclosed herein are microscope systems for simultaneous imaging and stimulation of tissue within a subject, the microscope system comprising: an optical assembly comprising: an illumination optical path comprising one or more light-emitting elements and configured to direct imaging light to tissue within a specified field-of-view; a stimulation optical path comprising one or more light-emitting elements and configured to direct stimulation light to tissue within said field-of-view, to tissue outside of said field-of-view, or to tissue partially within said field-of-view; an imaging optical path comprising one or more image sensors and configured to receive light reflected, scattered, or emitted by the tissue to generate an image of the tissue within said field-of-view; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly is removable from the baseplate.

1. In some embodiments, the specified field-of-view is about 1 mm×1 mm. In some embodiments, the specified field-of-view is about 2 mm×2 mm. In some embodiments, the specified field-of-view is about 4 mm×4 mm. In some embodiments, the baseplate comprises a central tapered bore with a plurality of partial-cylinder or partial-sphere bumps protruding from the central tapered bore. In some embodiments, the imaging light is fluorescence excitation light. In some embodiments, the fluorescence excitation light is provided within a wavelength range of 400 nm to 500 nm, and the stimulation light is provided within a wavelength range of 500 nm and 800 nm. In some embodiments, the fluorescence excitation light is provided within a wavelength range of 500 nm to 650 nm, and the stimulation light is provided within a wavelength range of 350 nm and 560 nm. In some embodiments, the optical assembly is configured to acquire images with a spatial resolution of better than about 2 µm at the center of the field-of-view. In some embodiments, the optical assembly is configured to acquire images with a spatial resolution of better than about 2 µm over the entire field-of-view by means of adding one or more corrective optical elements to the optical assembly. In some embodiments, the optical assembly further comprises one or more deformable lenses configured to adjust the focal depth of the imaging optical path, the stimulation optical path, or both. In some embodiments, the illumination optical path, stimulation optical path, and imaging optical path share at least one deformable lens. In some embodiments, the one or more deformable lenses are configured to adjust the focal depth of the imaging optical path, the stimulation optical path, or both, over a range of about 300 µm without loss of spatial resolution. In some embodiments, the one or more deformable lenses are selected from the group consisting of liquid lenses, liquid crystal lenses, and piezo-actuated tunable lenses, or any combination thereof. In some embodiments, the one or more deformable lenses are configured so that the imaging optical path and the stimulation optical path direct light to the same focal plane. In some embodiments, the optical assembly is configured to acquire images over a tissue volume of about 1 mm×1 mm×300 µm. In some embodiments, the stimulation optical path is further configured to direct the stimulation light to the tissue in a user-defined spatial pattern. In some embodiments, the user-defined spatial pattern has a spatial resolution of better than about 5 µm at the focal plane. In some embodiments, the microscope system further comprises a first processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and wherein the software-encoded instructions comprise instructions for modulating the stimulation light in a time-dependent or spatially-dependent manner to induce a neurological response in said brain tissue. In some embodiments, the total volume of the system is less than about 5 cm$^3$. In some embodiments, the total weight of the system is less than about 4 grams. In some embodiments, the illumination and imaging optical paths are packaged in a first housing as an optical imaging probe. In some embodiments, the stimulation optical path is packaged in a second housing as an optical stimulation probe. In some embodiments, the system comprises at least a second optical imaging probe, at least a second optical stimulation probe, or any combination thereof, attached to the baseplate. In some embodiments, the one or more light-emitting elements of the illumination optical path or the stimulation optical path comprise optical fibers that are coupled to one or more external light sources. In some embodiments, the system is mounted on or partially implanted within a freely mobile subject. In some embodiments, the illumination optical path, the stimulation optical path, and the imaging optical path further comprise a shared endoscopic probe that is partially implanted in the tissue of the subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used for photostimulation of neuronal tissue of the central nervous system, peripheral nervous system, or both. In some embodiments, the system is used to direct stimulation light to the tissue in a time-modulated or spatially-modulated manner that produces a therapeutic effect.

Disclosed herein are methods for simultaneous stimulation and imaging of tissue within a subject, the method comprising: providing a microscope system described in the embodiments above wherein the system is used to direct stimulation light to the tissue in a time-modulated or spatially-modulated manner that produces a therapeutic effect; providing a subject comprising the tissue to be stimulated and imaged; mounting or implanting the microscope system of step (a) on or within the subject; and generating one or more images of the tissue before, during, or after directing stimulation light to the tissue of said subject in a time-modulated or spatially-modulated manner.

In some embodiments, the subject is selected from the group consisting of mice, rats, cats, dogs, pigs, cows, horses, monkeys, chimpanzees, orangutans, gorillas, and humans. In some embodiments, the method is performed as part of preclinical research. In some embodiments, the method is performed as part of clinical research. In some embodiments, the method further comprises determining a clinical diagnostic test result. In some embodiments, method further comprises directing stimulation light to the tissue in a time-modulated or spatially-modulated manner that produces a therapeutic effect.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 15A: 455 nm excitation LED, 590 nm activation LED. FIG. 15B: 560 nm excitation LED, 455 nm activation LED.

DETAILED DESCRIPTION

Figure 1A:
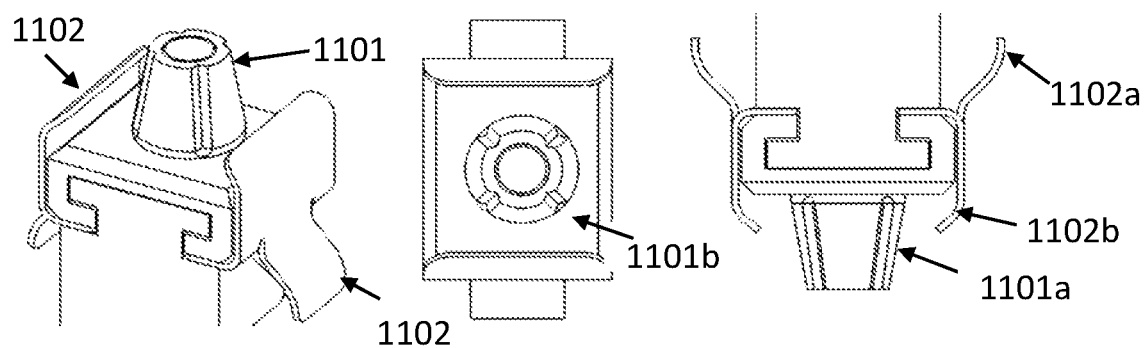
FIG. 1A shows a microscope configured for attachment to a baseplate via semi-kinematic coupling.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Additionally, various aspects of the invention described herein may be applied to any of the particular applications set forth below or in any other type of imaging setting. The invention may be applied as a standalone method or system, or as part of an integrated imaging system. It shall be understood that different aspects of the invention can be appreciated individually, collectively, or in combination with each other. Any description of alignment and assembly of optical and/or mechanical components for the purpose of miniaturized fluorescent imaging herein may also be applied to alignment and assembly of components (e.g., reflective or refractive optical surfaces such as lenses, mirrors, prisms or combinations thereof, wave guides or cavities, thermal elements, electric current or voltage sources, electronic circuit components such as capacitors, inductors and diodes, electromagnetic oscillators or antennae, gas discharge devices, radiation sources and radiation filters) used in other imaging techniques known in the art. For example, ultrasonic, microwave, thermal, radioactive, electron and/or other type of imaging device(s) (also referred to herein as "microscope (s)") may equally benefit from features described herein.

The present disclosure provides miniaturized devices, systems and methods for imaging of biological specimens. In some embodiments, the invention provides devices, systems and methods for in vivo fluorescent brain imaging in freely-behaving rodents. An aspect of the invention relates to an imaging device, comprising: a baseplate; a device body; and a removeable and replaceable cable assembly, wherein the device body is connected and separated with the baseplate in a tools-free, reproducible manner. In some embodiments, an imaging device may be provided, comprising: a baseplate configured to be attached to a subject having a target region to be imaged; a removeable and replaceable cable assembly; and a device body having a sensor cap assembly comprising an image sensor configured to image the target region when the device body is connected to the baseplate, wherein the device body is configured to be connected to and separated from the baseplate in a reproducible manner.

In some embodiments, the baseplate can comprise one or more subject attachment mechanism configured to attach the baseplate to the subject so that the base plate does not move relative to the target region. The baseplate and device body may comprise mating surfaces that can mechanically prevent at least one of rotational movement or axial movement between the base plate and the device body when the device body is connected to the baseplate. Optionally, the device body comprises one or more grooves complementary to one or more bumps in the baseplate, such that the device body is configured to be connected to and separated from the baseplate via kinematic coupling of the device body and the baseplate. The one or more grooves may be positioned to cause the device body to snap to a particular alignment with the baseplate.

In some embodiments, the one or more bumps are evenly spaced. For example, the baseplate may have four bumps, which are spaced 90 degrees apart. The baseplate may have three bumps, which are spaced 120 degrees apart. The one or more bumps may comprise partial-cylinder bumps. The one or more bumps may also comprise partial-sphere bumps.

In some embodiments of the miniature imaging device, the device body comprises outer spring clips, such that the device body is secured to the baseplate through compression and release of the spring clips. In some cases, the spring clips comprise bent sheet metal clips. In some cases, the spring clips comprise molded plastic clips.

The cable assembly provided herein may comprise: a cable PCBA, a cap covering cable wires soldered to the cable PCBA, and a threaded collar. In such an embodiment, the threaded collar has an O-ring located inside of it, and the threaded collar slides down such that the O ring compresses against the cap to connect the cable assembly and the sensor cap assembly.

In some embodiment, the baseplate comprises shelf-like features. In some cases, the shelf-like features protrude from a plurality of edges (e.g., exterior surfaces) of the baseplate. In some cases, the shelf-like features protrude from at least two edges of the baseplate. In some cases, the shelf-like features protrude from at least three edges of the baseplate. In some cases, the shelf-like features protrude from four edges of the baseplate.

In some embodiments, the device body has a volume of 10 cubic centimeters or less. The base plate may have a maximum dimension of 3 cm or less. In some instances the device body weighs less than 3 grams. In some instances the device body weighs less than 2 grams.

The device body may have a housing containing one or more optical elements along an image collection pathway from the target region to the sensor cap assembly. In some embodiments, the base plate may have a hole and the device body may have an objective lens configured fit at least partially through the hole to capture light from the target region when the device body is connected to the baseplate.

The present disclosure further provides an imaging device, comprising: a device body having a volume of 10 cubic centimeters or less, said device body comprising an image sensor configured to image a target region of a subject; a sensor cap assembly comprising one or more objective lenses disposed along an image collection pathway from the target region to the image sensor, wherein the sensor cap assembly is configured to be connected and separated with the device body in a reproducible manner.

In some embodiments, the device body is connected to and separated from a baseplate using spring clips. In some cases, the spring clips comprise upper tabs and lower tabs. The upper tabs and the lower tabs may be connected such that compressing the upper tabs will cause the lower tabs to move apart. Likewise, the upper tabs and the lower tabs may be connected such that releasing the upper tabs will cause the lower tabs to move together.

In some cases, the spring clips connect the device body to a baseplate which has shelf-like features that extend outward from edges of the baseplate.

In such embodiments, the spring clips experience interference with the edges of the baseplate when the sensor assembly and the device body are in a docked position.

In some embodiments of the present disclosure, the baseplate comprises a central tapered bore. In some cases, partial cylinder bumps located on the inside walls of the central tapered bore couple to V-grooves in the device body.

An additional aspect of the invention relates to an imaging device, comprising: one or more objectives; and a device body, wherein the one or more objectives are configured to be connected and separated with the device body in a reproducible manner. Aspects of the invention may include an imaging device, comprising: a device body having a volume of 10 cubic centimeters or less, said device body comprising a sensor assembly comprising an image sensor configured to image a target region of a subject; and one or more objective lenses disposed along an image collection pathway from the target region to the image sensor, wherein the one or more objective lenses are configured to be connected and separated with the device body in a reproducible manner using spring clips. In such an embodiment, the spring clips may comprise upper tabs and lower tabs. In some cases, the upper tabs and the lower tabs are connected such that compressing the upper tabs will cause the lower tabs to move apart. In some cases, the upper tabs and the lower tabs are connected such that releasing the upper tabs will cause the lower tabs to move together.

In some embodiments, the spring clips connect the device body to a baseplate which has shelf-like features that extend outward from edges of the baseplate. In such embodiments of the present invention, the spring clips experience interference with the edges of the baseplate when the sensor cap assembly and the device body are in a docked position. In some cases, the imaging device has a baseplate having partial cylinder bumps which couple to V-grooves in the device body.

In some cases, the imaging device further comprises one or more objective mounts for holding and mounting said one or more objective lenses to the device body in a predetermined orientation with respect to the device body. The one or more objective mounts may aid in attachment and alignment of the one or more objective lenses to the device body. The imaging device may be configured to accept a plurality of objective lenses having different field of view or resolution characteristics with aid of the one or more objective mounts.

In some embodiments of the present disclosure, the device body of the imaging device has a housing containing an illumination source within the housing, configured to provide illumination to the target region via an illumination pathway. The one or more objective lenses may be configured to be positioned less than 5 mm away from the target region and provide a focused image to be captured by the image sensor. In any of the above embodiments of the imaging device described herein, the greatest dimension of the device body may be, for example, less than 20 mm. Optionally, the imaging device weighs less than 2 grams.

In any of the above embodiments, the sensor cap assembly may comprise a sensor cap comprising machined PEEK housing. The sensor cap assembly may further comprise a sensor printed circuit board assembly (PCBA) with a molded elastomeric Z-connector. In some embodiments, the sensor cap assembly further comprises a carrier PCBA gasket.

The imaging devices disclosed herein may have a sensor cap assembly that comprises a sensor Printed Circuit Board Assembly (PCBA) with a molded elastomeric Z-connector;

a carrier PCBA; foam tape; a carrier PCBA gasket, and a sensor cap. The foam tape may be, for example, very high bond (VHB) foam tape. The sensor cap may comprise semicrystalline material, such as machined PEEK. In some cases, this sensor cap is configured to connect to a cable assembly. For example, in some embodiment, the sensor cap is connected to the cable assembly via a thumb-nut located on a cable assembly.

Additionally provided herein are systems and methods for operation of a microscope system, also referred to herein as an optical system and/or an optogenetic microscope system. The microscope system may be configured to provide concurrent manipulation and observation of a sample. The sample can be a biological sample. At least a portion of the sample can comprise one or more objects of interest, for example, cells. In some cases, the sample can comprise neuronal populations. At least a portion of the sample that includes one or more objects of interest can be activated or deactivated by light stimulation from a microscope system. The stimulation light can stimulate light-activated ion channels (e.g., opsins) in a cellular membrane (this process may also be referred to as "optogenetic stimulation" or "optogenetic modulation"). The opsins can occur in the cellular membrane naturally. In some cases, the opsins can be loaded into the cellular membrane by a genetic modification of the cell that causes the cell membrane to incorporate opsins. Opsin generating genes can be introduced into the cell through virus mediated transfection.

The microscope system can simultaneously image the sample (e.g., using fluorescence) while providing stimulation light to the sample. Simultaneous imaging and stimulation can permit a user to observe one or more portions of the sample (e.g., cells, neurons, or neuronal populations) that are stimulated by the stimulation light. The sample can be simultaneously stimulated by stimulation light and imaged by imaging light with a single integrated optogenetic microscope system. The sample can be imaged optically, e.g., by collecting imaging light that is scattered, reflected, or transmitted by the sample, or by exciting fluorescence in the sample using an excitation imaging light source and collecting the emitted fluorescent light to form an image. The sample can be imaged by light provided directly to the sample. The sample can be imaged by light that is not transmitted through one or more boundaries such as skin or bone prior to being incident on the sample. In some embodiments, the disclosed optogenetic microscope systems further comprise a baseplate which may be mounted on or implanted at a fixed position on a freely mobile subject. The baseplate may be configured to receive the optogenetic microscope, thereby aligning the microscope relative to tissue of the subject upon attachment of the microscope to the baseplate, and also allows subsequent removal or replacement of the microscope.

The baseplate may also comprise one or more mounting/alignment members. For example, the baseplate may comprise a central tapered bore, with bumps projecting from the inner walls of the bore. These bumps may be complementary to grooves located in the device body housing. The device body housing and central tapered bore comprise mating features, thus allowing for easier self-alignment of the microscope upon attachment to the baseplate.

The baseplate may be permanently mounted, removably mounted, mounted for a predetermined period of time before self-detaching, or a combination thereof. The baseplate may have shelf-like features which protrude from its edges and assist in mounting of the baseplate to the subject. For example, in some cases, ledges protrude from one or more edges of the baseplate. In some cases, ledges protrude from two or more edges of the baseplate. In some cases, ledges protrude from three or more edges of a baseplate. In some cases, ledges protrude from four or more edges of a baseplate.

Further, the baseplate may be designed to be mounted for long periods of time (e.g., one or more years), intermediate periods of time (e.g., one or more months, one or more weeks), short periods of time (e.g., minutes, hours, days), or a combination thereof (e.g., part of the baseplate may remain for a long period of time while another part may be removed/come off after a short period of time). A more comfortable or better fitting baseplate design may be used for long-term mounting. The baseplate may remain on a subject during a course of a study, such as a preclinical or clinical trial.

The mounting/alignment members may be separately formed and mounted or attached to the housing and/or to one or more of the modules. In some cases, one or more mounting/alignment members may be integrally formed with the housing, or with one or more of the modules. Further, any description of mounting/alignment members located in the device body may also be applied to mounting/alignment members on the baseplate. The mounting/alignment members on the baseplate may be used for attachment of the baseplate to the subject (e.g., support feet, brackets, collars or other features ergonomically shaped to fit the subject) and/or for attachment of the baseplate and the device body. Embodiments of the present disclosure may provide for attachment of the device body to the baseplate via self-aligning mounting/alignment members. Attachment of the device body to the baseplate may be accomplished by providing mounting/alignment members on the device body, on the baseplate, or on both the device body and the baseplate. The mounting/alignment members may include extruded features, as well as receiving indents, grooves, locks, slots, ridges, flanges, snaps, threads, and/or other features. The mounting/alignment members may enable accurate and repeated positioning of modular components within the device body, and of the device body with respect to the baseplate. The mounting/alignment members can allow for self-aligning of the baseplate. In one example, the device body may be repeatedly attached and/or removed from the baseplate with aid of the mounting/alignment members on the device body and/or base plate. The mounting/alignment features may optionally have mating or interlocking features. Portions of the device body may be slid in or out relative to portions of the base plate in order to be mounted to the base plate or removed from the base plate.

Figure 1B:
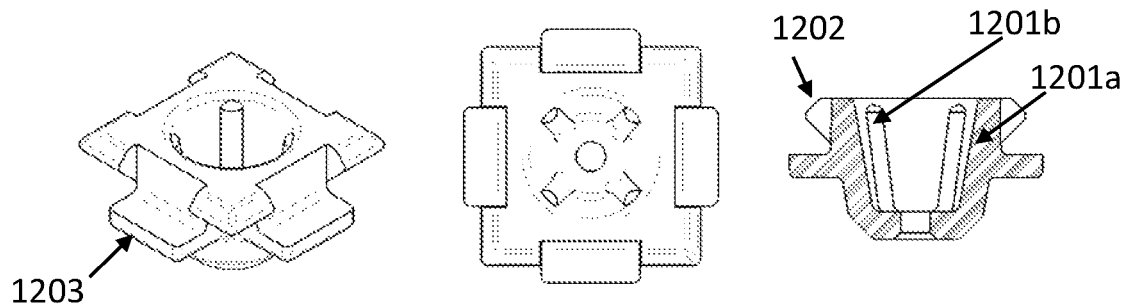
FIG. 1B shows a baseplate having partial-cylinder bumps located within a central tapered bore.

The mounting/alignment members may involve mechanical features that perform semi-kinematic coupling. For example, FIG. 1 and FIG. 2 provide an embodiment with spring-clip based mounting features and kinematic coupling or attachment as mounting/alignment members. This embodiment includes two subsystems: a microscope (FIG. 1A) and a baseplate (FIG. 1B).

FIG. 1A depicts a microscope enclosed in an objective housing 1101, which is connectively coupled to the baseplate using spring clips 1102. The objective housing 1101 is a CNC machined part and has a circular taper 1101a that protrudes from the microscope. The angle of the taper in this example is 20°. Additionally, there are four V-grooves 1101b cut along the surface of the taper at constant depth. The V-grooves in this example have a 120° profile and are equally spaced 90° apart about the central axis of the taper. The microscope has two spring clips 1102 that are mounted in a mirrored configuration about the center of the microscope. The spring clips 1102 are constructed of bent sheet metal. Upper tabs 1102a on one end have bends that create space between the clip and microscope. The opposing end of the clips have lower tabs 1102b that are angled in toward the microscope at 130°, in this example.

Baseplates of the present disclosure may comprise a tapered bore with any number, N, of internally protruding features, such has partial-cylinder (or partial-sphere) bumps. For example, FIG. 1B depicts an exemplary baseplate, which mechanically and/or systematically couples to the microscope of FIG. 1A. The baseplate is an injection molded plastic part with a central tapered bore 1201b and four partial-cylinder bumps 1201b that protrude at constant height from the inside walls of the bore, equally spaced 90° apart. This allows for four positions of alignment, which can be repeatably achieved while providing flexibility in positioning, while is important in an experimental setting. The upper perimeter edge of the baseplate has a triangular profile 1202. Approximately midway down the height of the baseplate are shelf-like features that extend out from the baseplate exterior 1203.

The mechanical features of the microscope and baseplate subsystems have two separate functions, which are 1) secure attachment, as described above, and 2) registration. The combined use of kinematic coupling and a spring-clip mechanism allows for repeatable XYZ registration of a microscope when docked with an associated implantable probe baseplate in such a system. Such systems may provide for a registration repeatability of +/−20 µm or better. Such registration repeatability is particularly beneficial in an experimental setting, as impedes the quality of experimental data by adding an additional variable that cannot be controlled for. Further, docking may be performed in a tools-free manner (semi-kinematic coupling), allowing for greater efficiency than those in the art. For example, manual attachment of the microscope and baseplate may be performed. Such manual attachment may be performed using one hand only. Tools-free attachment may require a minimal degree of force (e.g., less than 100 Newtons, less than 95 Newtons, less than 90 Newtons, less than 85 Newtons, less than 80 Newtons, less than 75 Newtons, less than 70 Newtons, less than 65 Newtons, less than 60 Newtons, less than 55 Newtons, less than 50 Newtons less than 45 Newtons, less than 40 Newtons of force). Likewise, tools-free detachment may require a minimal degree of force (e.g., less than 100 Newtons, less than 95 Newtons, less than 90 Newtons, less than 85 Newtons, less than 80 Newtons, less than 75 Newtons, less than 70 Newtons, less than 65 Newtons, less than 60 Newtons, less than 55 Newtons, less than 50 Newtons less than 45 Newtons, less than 40 Newtons of force).

The commonly employed method for docking and registration for microscopes uses a set screw threaded through the baseplate, which is tightened with a tool after the microscope is placed into the baseplate. A system applying this method is provided in FIG. 2C. Once tightened, the screw tip pushes the microscope body up against the inside of the baseplate. This method relies on planar surface-to-surface contact for registration of the microscope to the baseplate. The limitation of this type of registration is that the repeatability of planar surface contact is limited by manufacturing tolerances, such as flatness and perpendicularity. Additional disadvantages of the set screw method are that a separate tool is required, adding complexity to the docking procedure, and the force applied by the user is not controlled (a torque driver is rarely used) and is only limited by the strength of the screw threads. On top of manufacturing defects, it is possible for varying amounts of material deflection to affect registration. The set screw by design also causes wear on mating surfaces so components often need repair or replacement.

Another method known in the art has clamps on the microscope that are opened with a specially designed tool. A system applying this method is provided in FIG. 2D. The clamps are closed onto the imaging cannula (equivalent to baseplate) either by turning a cap or by springs once the special tool is released. Use of tools reduce efficiency associated with setting up microscope systems.

The microscopes of the present disclosure, in contrast, allow for one-handed, tool-free set up. The registration of the microscope relative to the baseplate is accomplished by inserting the objective housing 1101 into the bore of the baseplate 1201a and bringing into contact the V-groove features on the microscope 1101b with the partial-cylinder bumps 1201b in the baseplate. These complementary features form a kinematic coupling that results in highly repeatable positioning of the microscope relative to the baseplate.

The microscope's spring clips 1102 latch onto the upper edge of the baseplate 1202 to create a secure attachment. Microscopes having these spring clips may be configured for manual use or hands-free attachment. Such attachment may be performed with a single hand. For example, the microscope may engage in self-attachment and self-alignment. Attachment may be performed manually, by user action. Attachment and/or detachment may require 200 Newtons of force. Attachment and/or detachment may require less than 200 Newtons of force (e.g., 190 N, 180 N, 170 N, 160 N, 150 N, 140 N, 130 N, 120 N, 110 N, 100 N, 90 N, 80 N, 70 N, 60 N, 50 N, 40 N). Attachment of the microscope to the baseplate may also be performed with a single-hand. Attachment may require six or less motions, five or less motions, four or less motions, three or less motions, two or less motions, or one or less motion. For example, one embodiment requires four or less motions for attachment and/or detachment of the baseplate and microscope. Another embodiment requires three or less motions for attachment and/or detachment.

Figure 2A:
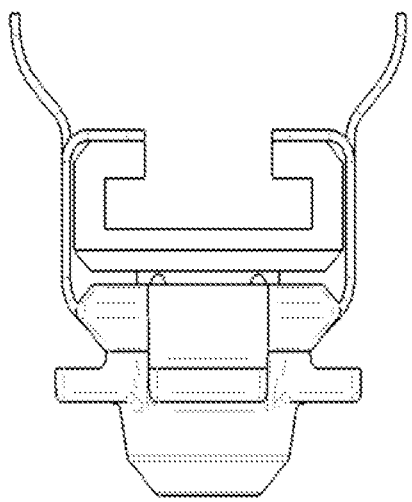
FIG. 2A shows a side view of the baseplate and microscope, connected using a spring clip.
Figure 2B:
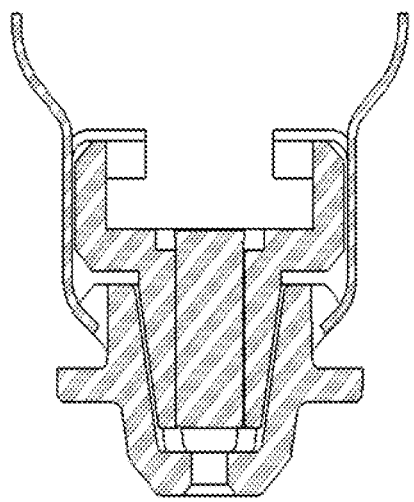
FIG. 2B shows a cross section of the baseplate and microscope, connected using a spring clip.
Figure 2C:
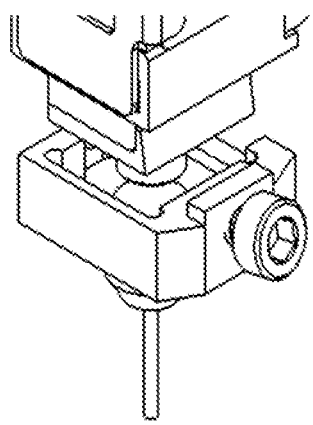
FIG. 2C depicts a screw-based alignment and attachment mechanism for connecting the baseplate to the microscope body.
Figure 2D:
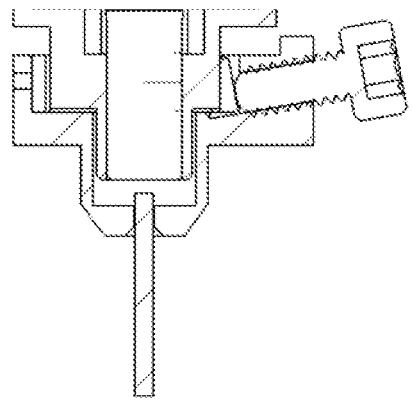
FIG. 2D depicts an exemplary alignment and attachment mechanism that relies on use of a tool for detachment of the baseplate from the microscope body.

Semi-kinematic coupling involves kinematic coupling of the groove and bump features with guidance and reinforcement provided via force exerted by the spring clip. In addition, the shelf feature 1203 on the baseplate acts as a guide and barrier for cement or other adhesive that is used to secure the baseplate during the implant procedure. The shelf shields the microscope interfacing surfaces from cement and provides increased surface area for adhesion. The docked configuration is shown in FIG. 2A and FIG. 2B.

The spring clip feature is designed such that in the docked position there is interference with the baseplate edges. This nominal interference means that the clips will be pushed out and the resulting spring force holds the microscope to the baseplate. To perform the docking, the user will squeeze the upper tabs 1102a together, which will cause the lower tabs 1102b to move apart so that they can slide past the edge of the baseplate. The user will then insert the microscope into the baseplate, and the baseplate and microscope couple and align into one of the four possible 90° positions. Once the microscope is fully seated, the user releases the tabs, pressure from which helps guide the microscope to the desired orientation. The docking is now complete, and the microscope has been registered and securely attached to the baseplate. These four docking positions are reliably, accurately, and repeatably secured by semi-kinematic coupling of the microscope and baseplate.

Systems and methods described herein employ semi-kinematic coupling to achieve repeatability, precision, reliability, and accuracy in assembling the microscope and baseplate. Kinematic mounts (or bumps) in the baseplate or the device body are designed to couple to kinematic grooves (or dips) in the respective component (i.e., the baseplate or the device body), which contain known contact points. By kinematically (or semi-kinematically) coupling the baseplate and the device body, the disclosed system allows for efficiency and reliability in assembly. In such a design, tangential friction at the contact surface and friction at the contact interface are controlled to achieve greater repeatability.

Alternative embodiments of the design may include variations on the kinematic coupling and/or variations on the attachment mechanism. Bumps, grooves, or similarly-functioning features may also be referred to as kinematic features. Any number of grooves and any number of bumps may be used. For example, N number of kinematic features (e.g., mounts, bumps, grooves) may be present on each component (e.g., the microscope and the baseplate). The kinematic features may be located in equidistant positions on each of the device body and baseplate, although this is not required. In some embodiments, the kinematic features are located in equidistant positions. In other embodiments, the kinematic features are not equidistant to each other.

In embodiments of the present disclosure, any number N of kinematic features may be located on each the device body and the baseplate. The number of kinematic features determines the number of attachment positions, each position employing different contact points. If the device body and baseplate, respectively, contain N bumps and N grooves, the device body (e.g., a microscope) would connect to the baseplate in N different positions. For example, the embodiment shown in FIG. 2A and FIG. 2B uses four equidistant V-grooves and four equidistant partial-cylinder bumps, meaning N=4. The number of grooves and bumps (N=4) enables four 90° (360°/4) positions of the microscope relative to the baseplate. However, three grooves and three bumps spaced 120° apart (N=3) would still be functional for achieving registration repeatability. In another embodiment, the partial-cylinder bumps may be replaced with partial-sphere bumps, also mating to V-grooves. A combination of partial-cylinder and partial-sphere bumps may also be used. Other attachment mechanisms may include, but are not limited to, threaded collars, bayonet mounts, magnets, or set screws. Bent sheet metal clips may be replaced with molded plastic clips in any embodiment of the present disclosure.

Figure 3:
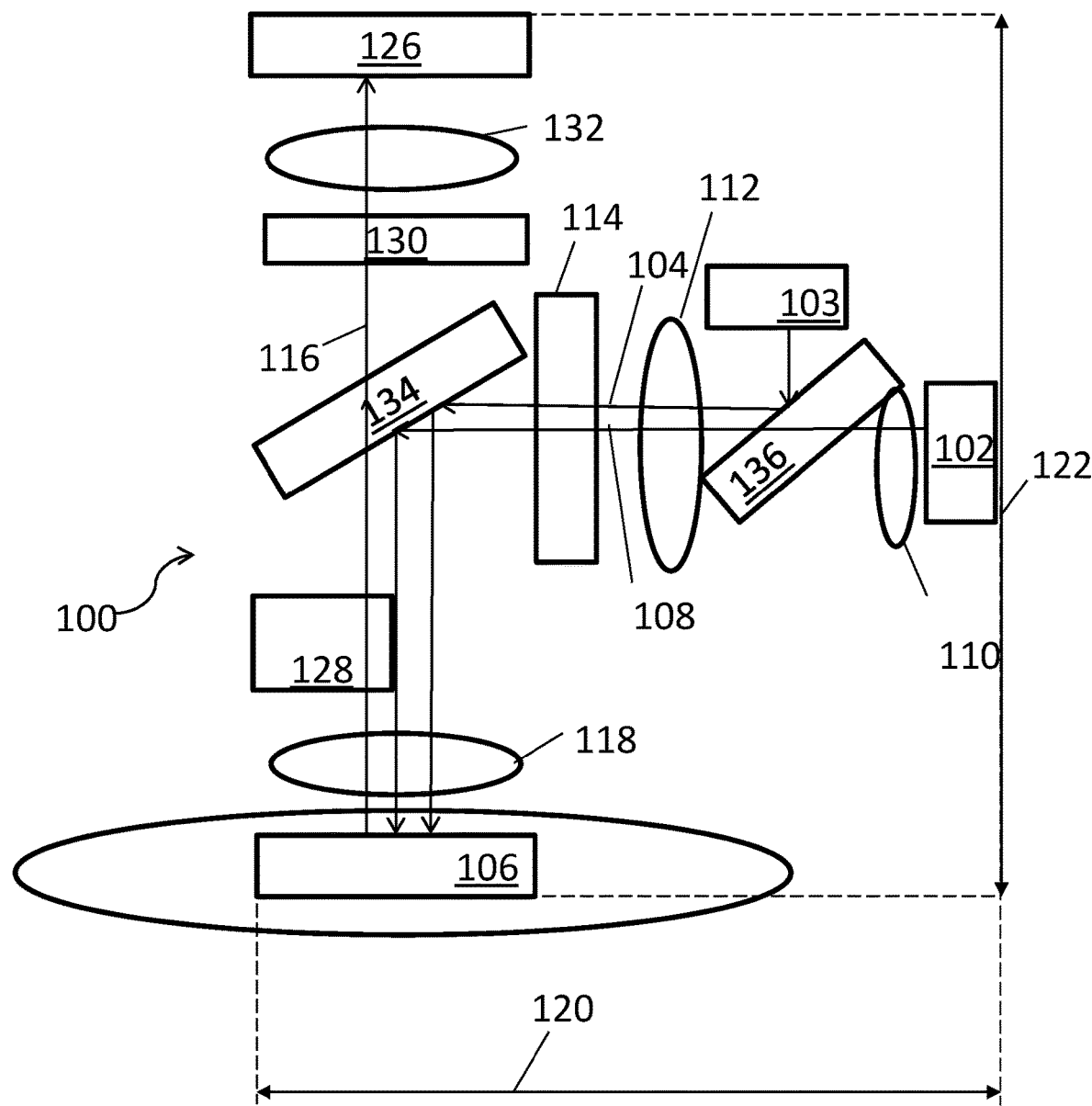
FIG. 3 shows a schematic of a small optogenetic microscope system.

The optogenetic microscope can be any microscope configured to deliver light to a sample from a first light source to generate an image of the sample and alternately or simultaneously deliver light to the sample from a second light source to stimulate at least a portion of the sample. Stimulation of the sample can comprise initiating an electrochemical signal from the sample. FIG. 3 shows a diagram of an optogenetic microscope system 100 configured to deliver imaging light and stimulation light to a sample. The microscope system 100 can deliver the imaging light and the stimulation light to the sample simultaneously. The microscope system can deliver the imaging light and the stimulation light to the sample at separate time periods.

The compact optogenetic microscope disclosed herein is one non-limiting example of an optical system. As used herein, an optical device or optical system may be any device or system that comprises one or more optical components, e.g., lenses, mirrors, optical filters, prisms, diffraction gratings, monochromators, and the like, that are arranged in a manner such that the device or system performs an optical function such as delivering light to a specified field-of-view, collecting light from a specified field-of-view and forming an image at a specified focal plane, providing a magnified image of a specified field-of-view, and the like. The arrangement of optical components in an optical device or optical system thus constitutes an "optical path" which functions to transfer light from one position in space to another. Thus one may refer, for example, to an "illumination optical path" used to deliver imaging light to the sample or tissue within a defined "field-of-view", or to a "stimulation optical path" used to deliver stimulation light to the sample or tissue within a defined field-of-view, or to an "imaging optical path" used to deliver light collected from the sample or tissue within a defined field of view to the image sensor.

As used herein, an "optical assembly" may refer to a grouping of one or more optical components that comprise all or a portion of the optical components of an optical device or system, and may often further comprise electronic components, e.g., light sources or photodetectors, and mechanical components, e.g., mounts or fixtures, that hold the individual optical components in a fixed or adjustable orientation relative to each other and/or a fixed or adjustable distance relative to each other. In some instances, an optical device or system may comprise more than one optical assembly (or optical sub-system). In some instances, an optical device or system may comprise two or more optical assemblies wherein the two or more different optical assemblies are configured to perform the same or different functions. For example, an optical assembly (e.g., an illumination optical assembly, or "optical illumination probe") may comprise the optical and electronic components required to deliver imaging light to the sample within a defined field-of-view. Alternatively, an optical assembly (e.g., a stimulation optical assembly, or "optical stimulation probe") may comprise the optical components required to deliver photostimulation light to the sample within a defined field-of-view.

In another instance, an optical assembly (e.g., an imaging optical assembly, or "optical imaging probe") may comprise the optical and electronic components required to both deliver imaging light to the sample within a defined field-of-view, and collect light that is reflected, scattered, or emitted by the sample to capture an image of the sample with a defined field-of-view. Thus an optical system such as the optogenetic microscope systems disclosed herein may, in some embodiments, comprise one or more optical assemblies or optical probes in any combination to provide a variety of illumination, photostimulation, and imaging functionalities. In some embodiments, the disclosed optogenetic microscope systems may further comprise additional mechanical components, e.g., housings, baseplates, or position adjustment mechanisms, electromechanical components, e.g., manual or motorized translation stages or other micro-positioning devices, or electronic components, e.g., light sources, photodetectors, image sensors, light sources, temperature sensors, temperature control elements, temperature controllers, analogue-to-digital converters, digital-to-analogue converters, amplifiers, processors, memory devices, and the like.

The microscope system can comprise an imaging light directing arrangement 103 and a stimulation light directing arrangement 102. The imaging light directing arrangement and the stimulation light directing arrangement can be contained in a housing that contains at least a fraction of one or more optical components of the microscope system. The light directing arrangement may be optically isolated from ambient light. The imaging light directing arrangement can include an imaging light source. The imaging light source can be on-board the microscope. The imaging light source can generate imaging light. The imaging light directing arrangement can be in optical communication with an imaging light source that is off board the light directing arrangement. The imaging light source can be off board the microscope. The imaging light source may or may not be contained in the housing. The imaging light directing arrangement can be in optical communication with the imaging light source through an optical transmission element, for example a fiber optic element. The stimulation light directing arrangement can be in optical communication with stimulation light source that is off board the light directing arrangement. The stimulation light source can generate stimulation light. The stimulation light source can be on-board the microscope. The stimulation light source can be off board the microscope. The stimulation light source may or may not be contained in the housing. The stimulation light directing arrangement can be in optical communication with the stimulation light source through an optical transmission element, for example a fiber optic element.

The optogenetic microscope can image light from a sample at different wavelengths (e.g., colors) such that a user can study different cellular components and/or interactions. In some cases, different cell populations can be identified by imaging of different color fluorescent tags. The microscope can be configured to magnify one or more features of a sample such that a user can study components and/or interactions outside a size range detectable by a user's eyes. The light imaged from the sample at different wavelengths can correspond to different colors that can be imaged in a multi-color microscope imaging process. The microscope system can be configured to detect light of multiple colors simultaneously.

The optogenetic microscope can be configured to perform single-color or multi-color imaging. The optogenetic microscope can simultaneously stimulate a sample while imaging two or more different color (e.g., wavelength) emissions (e.g., fluorescence) from the sample. In some cases the two or more different colors can be from two more different dyes that have been added to the sample. The dyes can be fluorescent dyes. Cells with different proteins and/or different genetic markers and/or different neurological functions can be identified with different dyes. The two color imaging can aid in identifying an object of interest (e.g. cell population) for targeting of stimulation light from the optogenetic microscope.

Imaging multiple colors simultaneously can permit a user to image different samples, for example, different cellular populations and interactions between the different cellular populations. The different cellular populations can be stained with a color marker that can be detected by the microscope system. Alternatively, the different cellular populations can naturally emit different color markers that can be detected by the microscope system. In some cases, subpopulations within a population can be identified with multi-color microscopy by detecting a protein or genetic marker. Differences in the subpopulation can be studied and/or studied by stimulation by the stimulation light with the multi-color imaging. In some cases, imaging dynamic from one cellular population and hemodynamics can be studied to identify metabolic and/or blood-brain barrier phenomena (e.g., drug delivery).

In some cases, the optogenetic microscope can be configured to perform single-color imaging. The optogenetic microscope can simultaneously stimulate a sample while imaging a single color (e.g., wavelength or wavelength band) emission (e.g., fluorescence) from the sample. The optogenetic microscope can comprise a monochromatic image sensor that detects light from the sample within a visible range of wavelengths. The optogenetic microscope can comprise a monochromatic image sensor that detects light from the sample outside of a visible range of wavelengths. The optogenetic microscope can comprise a monochromatic image sensor that detects light from the sample outside of and within a visible range of wavelengths. In some embodiments, the optogenetic microscope can comprise more than one image sensor, e.g., two, three, four, or more image sensors.

The microscope system provided herein can be configured to provide real-time simultaneous imaging and stimulation of one or more portions of a living sample. Each portion of the living sample can comprise one or more objects of interest such as cells or cell populations. The living sample can be subjected to various stimuli while one or more objects of interest (e.g., cells) of the living sample are simultaneously imaged and stimulated. The living sample can be subjected to effects of a pharmaceutical prior to or during simultaneous imaging and stimulation by the microscope system. In some cases, the living sample can be an organ and/or tissue in an organism. The organism can be subjected to various stimuli while one or more objects of interest (e.g., cells) of the organism are simultaneously imaged and stimulated. In some cases, the stimuli can be chosen to cause stress, tranquility, agitation, and/or another predetermined biological response by the organism.

In some cases, the microscope system described herein can permit observation of interactions between a first group of cells and a second group of cells in a sample. At least one of the first group of cells and the second group of cells can be a population of neurons. In an example, a user can detect a first group of cells and a second group of cells in a sample by directing imaging light to the sample using imaging functionality of the microscope system. The user can then provide stimulation light to at least one of the first group of cells and the second group of cells using stimulation functionality of the microscope system. Stimulation and imaging light can be provided to the sample simultaneously such that the user can continue to observe the first group of cells and the second group of cells while at least one of the first group of cells and the second group of cells is stimulated. The user can observe activity patterns that occur between the first group of cells and the second group of cells when at least one of the first group of cells and the second group of cells is stimulated.

The imaging light source may comprise one or more LEDs, or other types of light emitting elements. The imaging light source can be a light-emitting-diode (LED) or an organic light-emitting-diode (OLED). Light from the imaging light source 104 can be directed to the sample 106 through an optical arrangement comprising one or more optical elements. The imaging light source may provide essentially monochromatic light. Alternatively the imaging light source may provide imaging light at multiple wavelengths. In one example, the imaging light source may comprise two or more LEDs (or other light emitting elements) that emit light at two or more different colors (e.g., wavelengths or wavelength ranges). The imaging light source may provide light for single-color or multi-color imaging that is directed by the illumination optical path to all, or a portion of the sample or tissue within the field-of-view of the disclosed optogenetic microscopes or optical probes. In some embodiments, the one or more light emitting elements of the imaging light source may comprise optical fibers that are optically and/or mechanically coupled to one or more external light sources.

The imaging light can be an excitation light source such that when light from the imaging light is incident on the sample, the sample emits fluorescence from one or more fluorophores contained in the sample. The fluorophores can occur naturally in the sample or they can be added to the sample. In some embodiments, any type of luminescence may be detected for imaging of the sample, including but not limited to photoluminescence (e.g., fluorescence, phosphorescence), chemiluminescence, bioluminescence, or electroluminescence. Multiple colors as a result of reflectance, luminescence, scattering, or other light interactions may be detected. In some cases, light from the imaging light source can be incident on the sample and at least a fraction of the light can be reflected by the sample. The reflected light can be detected to generate an image of the sample.

In some cases, the imaging light can provide imaging light to the sample with a power density of at most about 1000 $\mu W/mm^2$, 900 $\mu W/mm^2$, 800 $\mu W/mm^2$, 700 $\mu W/mm^2$, 600 $\mu W/mm^2$, 500 $\mu W/mm^2$, 550 $\mu W/mm^2$, 500 $\mu W/mm^2$, 450 $\mu W/mm^2$, 400 $\mu W/mm^2$, 350 $\mu W/mm^2$, 300 $\mu W/mm^2$, 250 $\mu W/mm^2$, 200 $\mu W/mm^2$, 150 $\mu W/mm^2$, 100 $\mu W/mm^2$, 75 $\mu W/mm^2$, 50 $\mu W/mm^2$, 25 $\mu W/mm^2$, 15 $\mu W/mm^2$, 10 $\mu W/mm^2$, 5 $\mu W/mm^2$, 1 $\mu W/mm^2$, 0.5 $\mu W/mm^2$, or 0.1 $\mu W/mm^2$. In some cases, the power density can be greater than 1000 $\mu W/mm^2$. The power density provided by the imaging light can fall between any of the values listed. Highest levels of imaging light may refer to the power density of the imaging light incident on the sample. Alternatively, higher levels of imaging light may refer to the power density of the imaging light incident on a surface of an optical element in a light path that direct imaging light to the sample. Highest levels of imaging light may also refer to power consumed by the imaging light source.

The microscope device can additionally comprise a stimulation light source. The stimulation light source can be a single light source or a plurality (e.g. two or more) light sources. The stimulation light source can comprise a plurality of lights sources arranged in rows and/or columns in a matrix of m×n light sources where m can be an integer from 1 to 1000 and n can be an integer from 1 to 1000. The plurality of light sources in the stimulation light source can be arranged in one or more columns. The plurality of light sources in the stimulation light source can be arranged in one or more rows. The plurality of light sources in the stimulation light source can be arranged in an irregular pattern. The plurality of light sources in the stimulation light source can be arranged in an array. The light sources can be light emitting diodes (LEDs). The light sources can be organic light emitting diodes (OLEDs). The light sources can be micro-LEDs. The light sources can be high-power LEDs. The light sources can be laser diodes. The light sources can be vertical-cavity surface-emitting lasers (VCSEL). The light sources can be any other light emitting elements. In some cases, the stimulation light source may comprise two or more light-emitting elements that emit light at two more different colors (e.g., wavelengths or wavelength ranges). In some cases, the high-power LEDs can emit light with a power of at least about 0.1 W, 0.25 W, 0.5 W, 0.75 W, 1 W, 2 W, 3 W, 4 W, 5 W, 10 W, 15 W, 20 W, or 25 W. The high-power LEDs can emit light at a greater power than the light emitted by the imaging light source.

This stimulation light source can generate stimulation light 108. The stimulation light can be directed to the sample 106 by an optical arrangement. The optical arrangement that directs stimulation light to the sample can include at least some of the same optical elements as the optical arrangement that directs imaging light to the sample. One or more optical elements of the optical arrangement that direct imaging light to the sample can be shared with the optical arrangement for directing stimulation light to the sample. Stimulation light and imaging light can be transmitted through the shared optical element simultaneously. In some cases, one or more of the optical elements can be a filter element. The filter can be a spectral filter configured to transmit light in a predetermined range of wavelengths. The same filter and/or different filters may be provided for the imaging and stimulation light. The different filters can be configured to transmit different discrete wavelengths and/or ranges of wavelengths. The different filters can be configured to transmit the same discrete wavelength and/or ranges of wavelengths.

In some cases, the stimulation light can be provided to the sample at a higher power density relative to the imaging light. The low level power density of the imaging light can reduce the probability that the imaging light will inadvertently stimulate a portion of the sample. The power density of the stimulation light can be at least about 1.5×, 2×, 3×, 4×, 5×, 6×, 7×, 8×, 9×, 10×, 20×, 30×, 40×, 50×, 60×, 70×, 80×, 90×, or 100× the power density of the imaging light.

The stimulation light from the stimulation light directing arrangement and the imaging light from the imaging light directing arrangement can be directed through a dichroic mirror 136. The stimulation light can be transmitted through a condenser lens 110 prior to being directed with the imaging light at the dichroic mirror. The condenser lens can be placed close to the stimulation light source. The condenser lens can be almost touching the stimulation light source. The condenser lens can contact the stimulation light source. A distance between the condenser lens and the stimulation light source can be at most about 0.001 mm, 0.005 mm, 0.01 mm, 0.05 mm, 0.1 mm, 0.5 mm, 1 mm, 5 mm, 10 mm, 20 mm, 30 mm, 40 mm, or 50 mm. The condenser lens can condense light from the stimulation light source into a light beam with a flat intensity profile (e.g., spatially uniform intensity). The condenser lens can collimate the stimulation light. The condenser lens can condense light from the stimulation light source into a light beam that has little or no variation in intensity across the beam area. In some cases, the variation of intensity across the beam area of the stimulation light after transmission through the condenser can be at most about 50%. In some cases, the intensity across the beam area of the stimulation light after transmission through the condenser can vary by at most about 25%. In some cases, the variability of intensity across the beam area of the stimulation light after transmission through the condenser can be at most about 10%. In some cases, the variability of intensity across the beam area of the stimulation light after transmission through the condenser can be at most about 5%. In some cases, the variability of intensity across the beam area of the stimulation light after transmission through the condenser can be at most about 1%. Providing a uniform beam of stimulation light can be important for generating uniform stimulation of the sample.

After being transmitted through the dichroic mirror 136 the stimulation light and the imaging light can be transmitted through a second condenser lens 112 and an excitation filter 114. The second condenser lens can increase the attenuation of light from the stimulation light source and/or the imaging light source to the sample. The second condenser lens can collect light from different angles and redirect this light into a collimated beam for delivery to the sample. Without the condenser lens, light traveling at some of these different angles may not remain in the optical path to be delivered to the sample. Without the condenser lens the irradiance of the imaging light source may need to be increased in order to provide sufficient light to the sample for imaging. Increasing the irradiance of the imaging light can increase the probability of undesirable stimulation of the sample with the imaging light.

A second dichroic element 134 can direct the stimulation and/or the imaging light to the sample.

Light from the sample, for example fluorescence emission and/or reflected light from the sample can be directed through an optical path to an image sensor 126 to generate a digital representation of the image of the sample. When light from the sample is emitted and/or reflected in two or more different wavelength ranges (e.g., colors) a chromatic aberration correction element 128 can be provided in the optical path between the sample and the image sensor. The chromatic aberration correction element can adjust the focal length of the light in one or more of the different wavelength ranges such that the focal points are substantially the same. The chromatic aberration correction element can adjust the focal length in one or more of the different wavelength ranges such that light in each of the different wavelength ranges is focused onto a light detector in the image sensor.

The optical path from the sample to the image sensor can also include an emission filter 130 and/or a tube lens 132. The emission filter can prevent light in one or more wavelength ranges from being transmitted to the image sensor. The emission filter can select light in one or more wavelength ranges to be transmitted to the image sensor. The tube lens can focus light from the sample on to the image sensor. The tube lens can correct spherical and chromatic aberrations.

The microscope system can be sized and shaped such that a living organism can wear the microscope system while the microscope system is performing imaging and stimulation of at least a portion of one or more tissues or organs of the organism. The microscope system can be sized and shaped such that typical motions and/or activities of the living organism are not impeded and/or altered by the microscope system when the microscope system is worn by or attached to the living organism. For example, the living organism may be freely moving while the microscope system is imaging and stimulating a tissue of the living organism. The living organism may be walking about while the microscope system is imaging and/or stimulating a tissue of the organism such as brain tissue.

In some cases the disclosed microscopes and optical systems (e.g., optical probes) can be a relatively small. The microscope or system can have a maximum dimension less than about 5 inches, 4 inches, 3 inches, 2 inches, 1 inch, or 0.5 inches. The microscope or system can have a maximum dimension less than about 12.7 cm, 10.2 cm, 7.6 cm, 5.1 cm, 2.5 cm, or 1.3 cm. A maximum dimension of the microscope or system may be any dimension of the microscope or system (e.g., length, width, height, diameter) that is greater than the other dimensions of the microscope. The microscope or system may have a volume of less than or equal to about 10 cubic inches, 7 cubic inches, 6 cubic inches, 5 cubic inches, 4 cubic inches, 3 cubic inches, 2.5 cubic inches, 2 cubic inches, 1.5 cubic inches, 1 cubic inch, 0.7 cubic inches, 0.5 cubic inches, 0.3 cubic inches, 0.1 cubic inch, 0.05 cubic inch, 0.01 cubic inch, 0.005 cubic inch, or 0.001 cubic inch. The microscope or system may have a volume of less than or equal to about 170 $cm^3$, 115 $cm^3$, 100 $cm^3$, 82 $cm^3$, 66 $cm^3$, 50 $cm^3$, 40 $cm^3$, 33 $cm^3$, 25 $cm^3$, 16 $cm^3$, 11 $cm^3$, 8 $cm^3$, 5 $cm^3$, 1.6 $cm^3$, 0.8 $cm^3$, 0.2 $cm^3$, or 0.02 $cm^3$. The microscope or system may have a lateral cross section (e.g., footprint) or less than or equal to about 5 square inches, 4 square inches, 3 square inches, 2 square inches, 1.5 square inches, 1.2 square inches, 1 square inch, 0.9 square inches, 0.8 square inches, 0.7 square inches, 0.6 square inches, 0.5 square inches, 0.3 square inches, 0.1 square inches, 0.05 square inches, 0.01 square inches, 0.005 square inches, or 0.001 square inches. The microscope or system may have a mass of less than or equal to about 10 grams, 7 grams, 5 grams, 4 grams, 3.5 grams, 3 grams, 2.5 grams, 2 grams, 1.5 grams, 1 gram, 0.5 grams, or 0.1 grams. The small dimensions may be useful for applications where a subject may be small, to provide reduced interference with activities of the subject by the microscope. A small lateral cross-section is useful when the subject is small and/or there is a limited space or area where the microscope or system may be mounted. A small lateral cross-section can permit many microscopes or optical probes to be mounted in a space with limited area. The small microscope or optical system may be capable of simultaneous stimulation and imaging as described herein. The small microscope or optical system may be advantageously configured to provide simultaneous stimulation and imaging within the limited dimensions, as described elsewhere herein.

As shown in FIG. 3 the microscope system 100 can include a plurality of components (e.g., optical elements) within the dimensions 120 and 122. Not shown is a further dimension, which extends perpendicular to the dimensions 120 and 122. Although not necessarily limited thereto, each of these dimensions can be less than an inch. In some cases, dimension 120 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches. In some cases, dimension 122 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches. In some cases the dimension extending perpendicular to the dimensions 120 and 122 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches.

The microscope can be configured to magnify one or more portions of a sample such that a user can study the one or more portions of the sample that are outside a size range detectable by a user's eyes. The microscope system can be configured to magnify a portion of the sample that contains one or more objects of interest that a user can stimulate using the stimulation light. In some cases the microscope can be a relatively small microscope. The microscope may be mounted onto or attached to a living organism or a non-living organism. In some instances, the microscope may be mounted to an exterior of an organism (e.g., over skin of the organism). The microscope may be used to image a sample on or within the organism. For example, the microscope may be mounted to a head of a subject and used to image brain tissue of the organism. The microscope may be mounted to a subject and used to image any other tissue on or within the subject. Examples of samples may include any biological sample or tissue, such as nervous tissue (e.g., brain tissue), muscle tissue, connective tissue, cancerous tissue, organ tissue, cardiac tissue, vascular tissue, or epithelial tissue. A subject may be a human subject or an animal subject. In some embodiments, animal subjects may include rodents (e.g., mice, rats, rabbits, guinea pigs, gerbils, hamsters), simians (e.g., monkeys, chimpanzees, orangutans, gorillas, and humans), equines (e.g. horses), bovines (e.g., cows), canines (e.g., domestic dogs), felines (e.g., domestic cats), avines, insects, or any other types of animals. In some instances, the subjects may weigh less than about 50 kg, 40 kg, 30 kg, 20 kg, 15 kg, 10 kg, 5 kg, 3 kg, 2 kg, 1 kg, 750 grams, 500 grams, 400 grams, 300 grams, 200 grams, 100 grams, 75 grams, 50 grams, 40 grams, 30 grams, 25 grams, 20 grams, 15 grams, 10 grams, 5 grams, 3 grams, or 1 gram. In some embodiments, the microscope can be mounted on or inserted into a living organism or a non-living organism, and used for pre-clinical or clinical research. In some embodiments, the microscope can be used for clinical diagnostics, e.g., to determine a clinical diagnostic test result, or for therapeutic applications, e.g., for photostimulation of neuronal tissue. In some embodiments, the disclosed microscope or related optical systems may be used for imaging and/or photostimulation of neuronal tissue of the central nervous system. In some embodiments, the disclosed microscope or related optical systems may be used for imaging and/or photostimulation of neuronal tissue of the peripheral nervous system. In some embodiments, the disclosed microscope or related optical systems may be used for imaging and/or photostimulation of neuronal tissue of both the central and peripheral nervous systems.

The microscope (or an optical assembly thereof) can be coupled, optically and/or mechanically, to a probe inserted into an organism. The probe may or may not contact a tissue of the organism. The probe may be partially implanted in the tissue of the organism. The probe can deliver imaging light and stimulation light to a sample simultaneously. The probe can deliver imaging light and stimulation light to a sample directly. The probe can deliver imaging light and stimulation light to a sample without transmitting the imaging light and/or the stimulation light through a biological barrier such as skin or bone. The probe can comprise an objective lens. Alternatively, the probe may not include an objective lens.

The microscope can be used in vivo, or in vitro. In some instances, the microscope may be used in vivo for a subject that is conscious. The microscope may be used in vivo for a subject that is not anesthetized. The microscope may be used in vivo for a subject that may be freely moving or mobile. The subject may be able to freely walk around an environment while the microscope is connected to (e.g., mounted on, inserted within) the subject. The subject may be able to freely walk around an environment while the microscope is imaging a sample of the subject. A small microscope, such as those having dimensions as described elsewhere herein, may be advantageous to provide little interference with activities of the subjects, or to be used with smaller subjects, such as those having characteristics described herein.

Systems of the present disclosure may comprise one or more component parts. Such component parts may be removeable and/or replaceable. For example, one aspect of the present disclosure relates to an imaging device, comprising: (i) a baseplate configured to be attached to a subject having a target region to be imaged; (ii) a removeable and replaceable cable assembly; and (iii) a device body having a sensor cap assembly and further comprising an image sensor configured to image the target region when the sensor cap assembly is connected to the device body, wherein the device body is configured to be connected to and separated from the baseplate in a reproducible manner.

Figure 4:
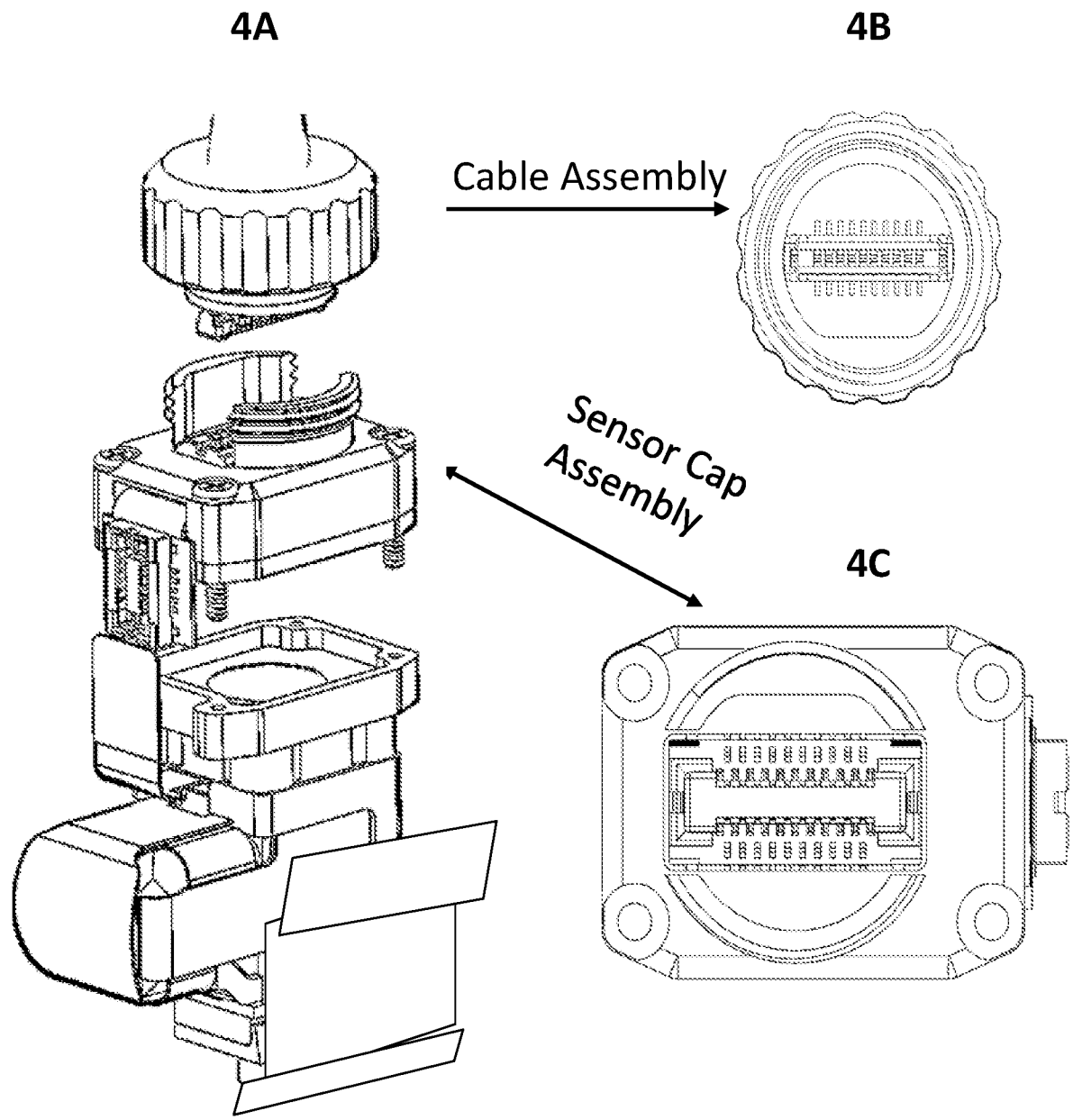
FIG. 4 provides a schematic of a small optogenetic microscope system (FIG. 4A) having a cable assembly (FIG. 4B) and a sensor cap assembly (FIG. 4C).

Removeable components typically involve an attachment mechanism that adds mass and/or volume to the device, such as the threaded collar and O-ring provided in FIG. 4. It might appear counterintuitive to include additional or unnecessary components (e.g., the sensor cap assembly, cable assembly) to a miniature device meant for wear by rodents, who are very sensitive to the weight and size of the device. However, replaceable, removable parts decrease the risk of damage to one component of the imaging system requiring extensive repairs (or replacement) of the entire system. This is particularly important for devices, systems and methods for in vivo fluorescent brain imaging in freely-behaving rodents, as rodents may chew or otherwise damage any malleable portions of the device.

Figure 5:
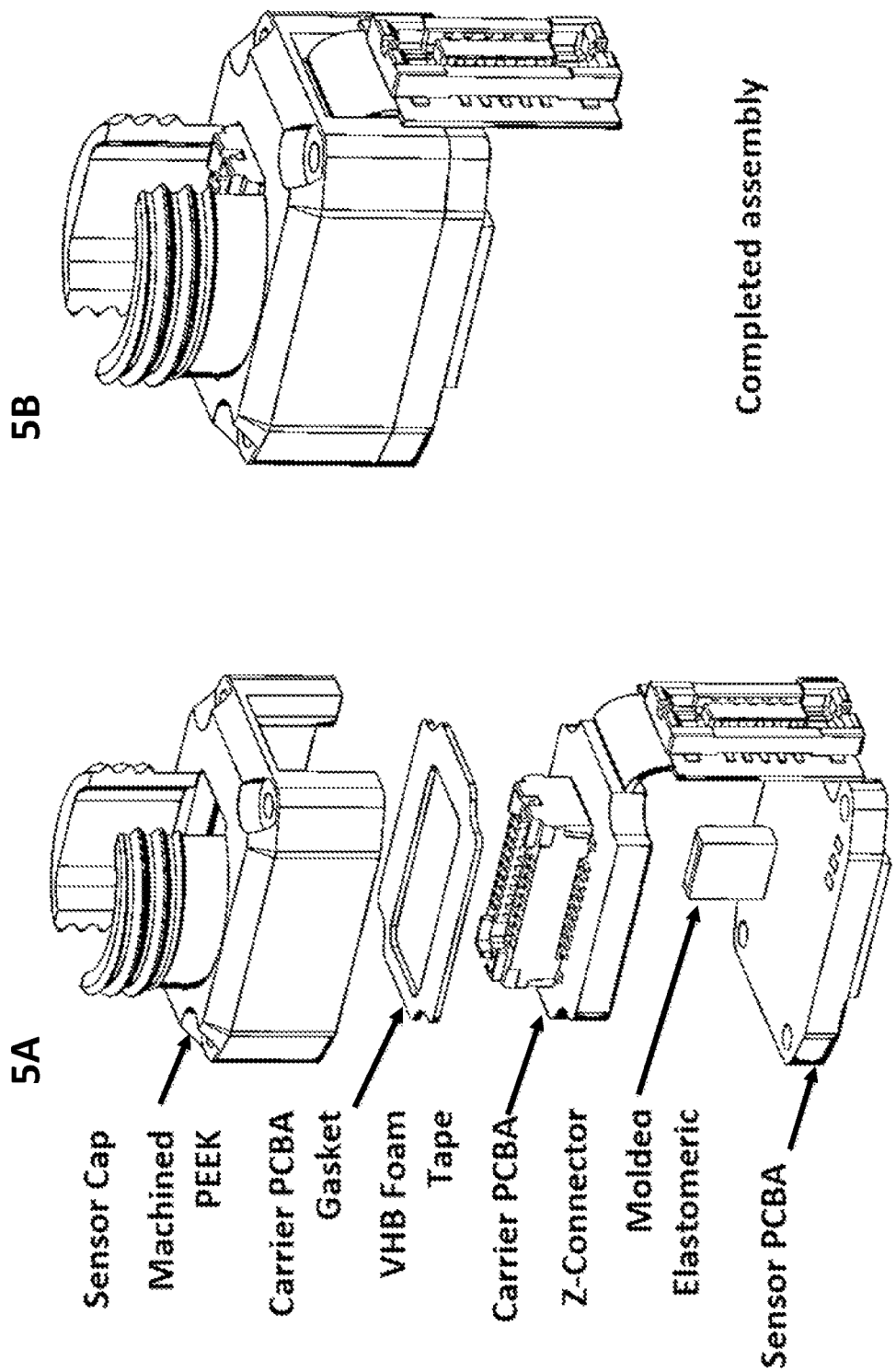
FIG. 5 provides an overview of a sensor cap assembly and its component parts (FIG. 5A).

In an embodiment of one of the miniature microscopes provided herein, the microscope system comprises a cable assembly and a sensor cap assembly, as provided in FIG. 4. A sensor cap assembly comprising a sensor cap in a housing made of a thermoplastic material, such as machined polyether ether ketone (PEEK), is located at the top of the microscope. FIG. 5 (5A, 5B) provides an overview of the sensor cap assembly, which comprises a sensor Printed Circuit Board Assembly (PCBA) with a molded elastomeric Z-connector; a carrier PCBA; foam tape (e.g., very high bond (VHB) foam tape); a carrier PCBA gasket, and a sensor cap comprising a machined PEEK housing. The sensor cap is configured to connect to the cable assembly via a thumbnut located on the cable assembly.

As shown in FIG. 5 (5A, 5B), the sensor cap assembly comprises a sensor cap with a VHB gasket placed inside, and a carrier PCBA adhered to the gasket. A Z-connector is located on top of the carrier PCBA pads and in the corner of the sensor cap. To assemble the sensor cap assembly, RTV is applied around the inner walls of the sensor cap and the z-connector. The sensor PCBA is then placed on top of the sensor cap, and the gap between the side connector and sensor PCBA is filled with RTV. The cable assembly is the user-replaceable component. The cable assembly (FIG. 4C) plugs into a socket on the sensor cap assembly. The keyed profile guides the orientation of the cable assembly and the thumb nut on the cable assembly threads onto the sensor cap to lock the connection. The sensor cap assembly remains on the microscope, and is connected as shown in FIG. 4A.

Figure 6:
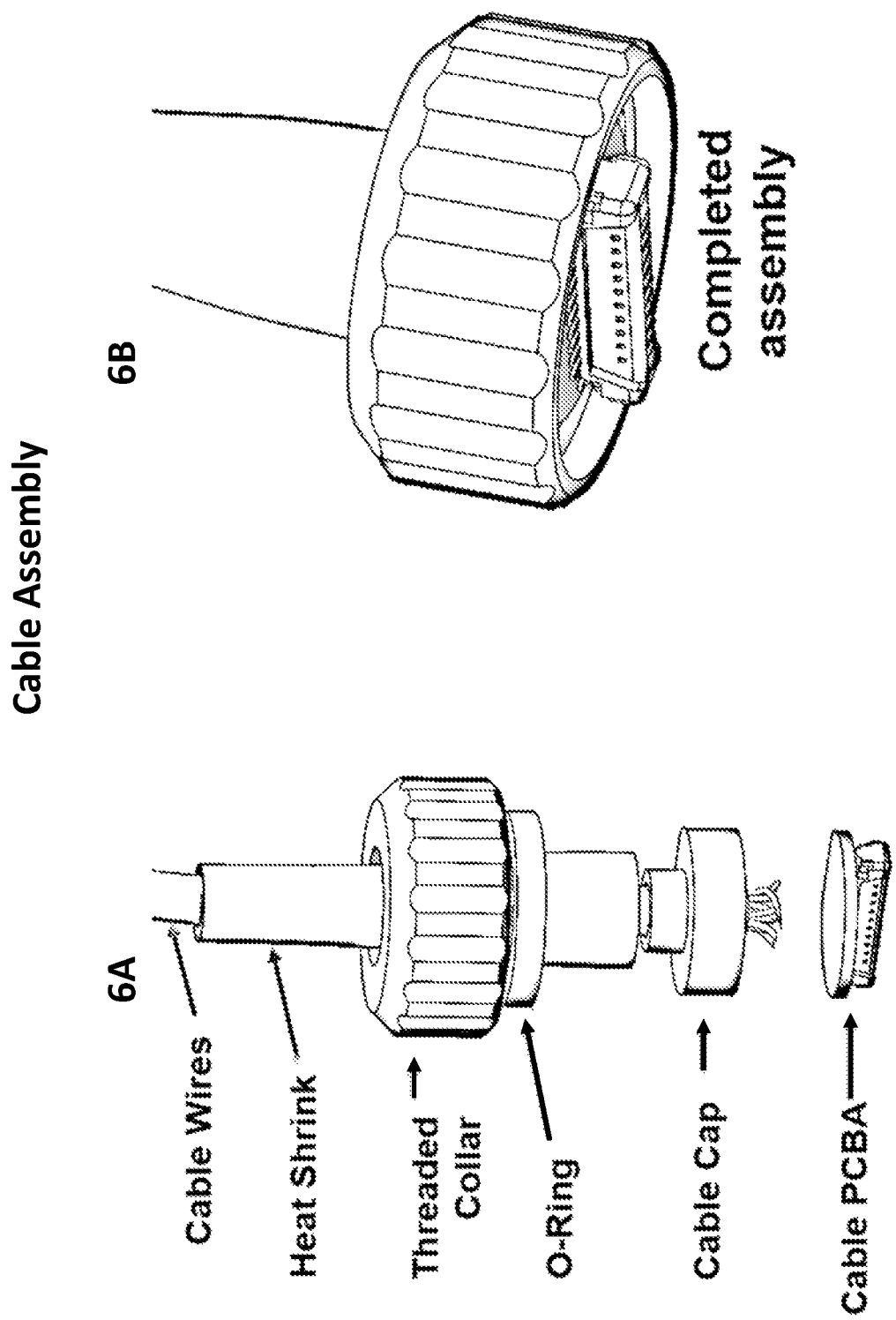
FIG. 6 provides an overview of a cable assembly, including its component parts (FIG. 6A) and a completed assembly (FIG. 6B).

FIG. 6 provides an overview of the cable assembly. FIG. 6 provides an exemplary cable assembly, comprising a cable PCBA, a cap covering cable wires soldered to a PCBA, and a threaded collar with an O-ring located inside of it, wherein the threaded collar slides down such that the O ring connects to and encapsulates the cap. Although adding mass to the device, the sensor cap and cable assembly are particularly advantageous, as they reduce time inefficiencies and cost inefficiencies associated with complex and specialized repairs. The sensor cap covers sensitive electronics and optical components, reducing risk associated with performing repairs involving the cable wires and cable PCBA when such components are exposed. Thus, the cable assembly can be easily removed and attached, making repairs more user-friendly and reducing both time and cost inefficiencies. The removeable and replaceable cable assembly, which has cable wires and the cable PCBA, securely attaches to the sensor cap assembly. In an exemplary embodiment, the cable assembly comprises cable wires surrounded by heat shrink and having a threaded color, O-ring, cable cap and cable PCBA with a header that plugs into a socket on the sensor cap assembly. To attach the cable assembly, the header on the cable assembly plugs into a socket on the sensor cap. As shown in FIG. 4, the header can have a keyed profile, which helps guide its orientation, and a thumb nut on the cable assembly threads onto the sensor cap to lock the connection.

Relative to conventional microscopes with cables or probes, the removeable and replaceable cable assembly makes repairs less risky and more user-friendly. If the cable were not detachable from the sensor cap assembly, damage to the cable would require a user to send the imaging device back to the manufacturer, or a similarly-suited service provider, to perform the repair. However, because the cable assembly is removably connected to the sensor cap assembly, damage to the cable assembly does not impact the sensor cap assembly or image sensor and such costs are spared. Additionally, repairing the cable assembly no longer exposes sensitive parts of the microscope, and replacing damaged cable wires would not require tools or specialized expertise. The sensor cap assembly comprises a sensor cap made of a crystalline material (e.g., machined PEEK), which further protects and covers sensitive electronics. The sensor cap covers and minimizes exposure of components that would be expensive and/or otherwise unnecessary to replace if damaged, such as optical components or sensitive electronics (e.g., carrier PCBA, sensor PCBA, image sensor). See FIG. 5A. Without a sensor cap, repairs would require a service provider with proper expertise and tools (such as the manufacturer) to perform. Repairs also would often require recalibration of the microscope. A user could remove a cable, order a new one, and re-attach the cable without having to disturb the subject or recalibrate the microscope.

Figure 7:
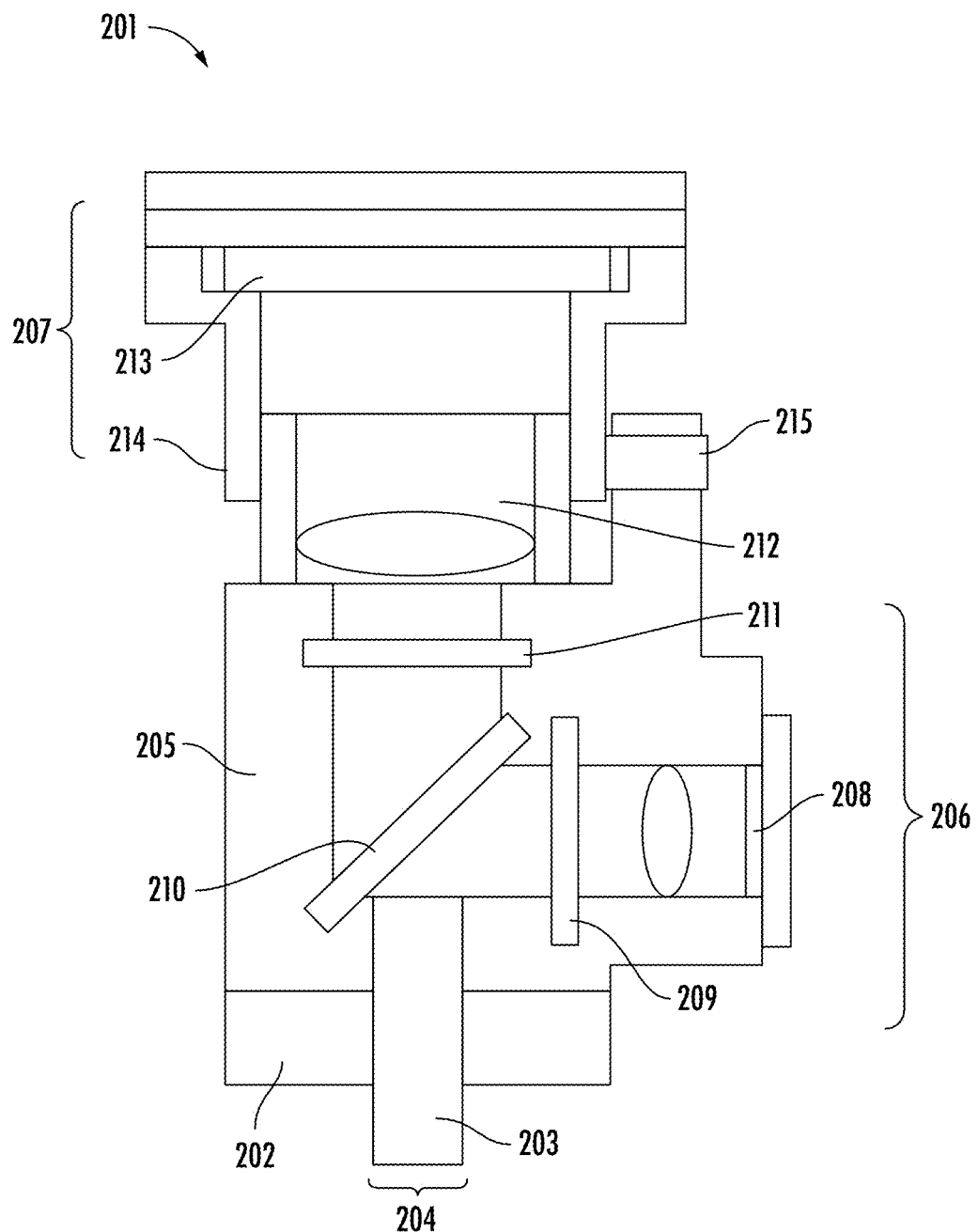
FIG. 7 is a cut-away perspective side view of a miniaturized imaging device.

With reference to FIG. 7, an aspect of the invention relates to a miniaturized fluorescence imaging device, such as, for example, a miniaturized imaging device 201 having a width of less than about 15 mm, a depth of less than about 10 mm and a length of less than about 20 mm. Embodiments of the invention may include devices with smaller and/or larger dimensions, such as, for example, devices having dimensions in the range of 0.1-30 mm in any given spatial direction. The device 201 may comprise a base plate 202, configured to be attached to a subject (not shown). An objective 203 may extend through the base plate toward the subject. The objective may be a lens. The objective 203 may have an imaging field of view (FOV) 204. The FOV may be a region of a target that is imaged by the imaging device. Generally, the device 201 may have a housing 205 which may be formed of one, two, three or more separate pieces. For example, separate housings may be provided for an optical unit 206 and a focusing unit 207, wherein each of these housings may further comprise multiple parts.

A light source 208 (e.g., light emitting diode (LED), organic light emitting diode (OLED), laser diode, laser, gas discharge element, or combination or arrays thereof) may reside in the optical unit 206. The light source may be provided within a housing of the imaging device. Any description herein of an LED may apply to any other light source, including those described above. The LED 208 may emit light in a predetermined frequency range. The frequency range of the light from the LED 208 may be selectively narrowed by passing through an excitation filter 209. The resulting excitation wavelength may range, for example, from 460 nm to 500 nm. Alternative configurations of the light source 208, excitation filter 209 and/or additional optical components can permit one or more excitation wavelength ranges to be provided from the optical unit 206. Furthermore, wide or narrow excitation wavelength ranges may be provided (e.g., less than about 100 nm, 75 nm, 50 nm or 25 nm, less than 15 nm, monochromatic light). The electric power to the light source 208 may be varied in accordance with the selected wavelength range(s), desired resolution, FOV and/or other imaging parameters. For example, the power may be about 0.1 mW, 1 mW, 10 mW, 100 mW, 1000 mW or any intermediate value (e.g., 200 mW, 400 mW, 600 mW) or range (e.g., 400-500 mW, 500-600 mW). In some cases, power may be varied or controlled dynamically in accordance with imaging requirements (e.g., power may be adjusted when the imaging parameters of the objective 203 change, such as when one type of objective 203 is swapped by another type of objective 203). The excitation light may then be directed toward a dichroic 210, wherein the light may be reflected in a predetermined direction. As shown in FIG. 7, the excitation light and the dichroic may be arranged such that the excitation light is reflected in a direction parallel to the axis of the objective 203.

The frequency of the excitation light may be in a predetermined range in order to excite fluorescence emission in a target location on the subject (also referred to herein as "sample" or "specimen"). The sample may be made fluorescent through any technique known in the art. For example, a sample may be fluorescent as a result of expression of a fluorescent protein, or the sample may be labeled with fluorescent stains. The excitation light may be passed through the objective lens 203 (e.g., gradient index (GRIN) lens, linear Fresnel lens, collimating lens, or conventional spherical lens) onto the sample, wherein the fluorescence in the sample may give rise to emitted light which may be collected by the same objective 203. The epifluorescent light received by the objective 203 from the direction of the sample may also include excitation light reflected off of the sample. Therefore, the light received by the objective may be passed through the dichroic 210 and further through an emission filter 211 in order to filter out light frequencies not associated with the fluorescence emission from the sample. The emission wavelength may range, for example, from 510 nm to 560 nm.

An achromatic lens 212 and/or one or more other optical elements (e.g., reflective and/or internally reflective elements, refractive and/or internally refractive elements, or prisms) may further focus the emitted light onto an image sensor 213 (e.g., a complementary metal oxide semiconductor (CMOS) sensor). The distance from the achromatic lens 212 to the image sensor 213 may be adjusted through a focusing mechanism 214, which may be configured as a threaded mechanism. The threaded mechanism may comprise additional guiding equipment, such as for example, bearing sets, optical measurement of focusing distance, and other means. The threaded mechanism may for example be configured as a translation stage, wherein a driving motor may rotate a lead screw in order to slide the focusing portion of the device along a shaft utilizing linear motion bearings. Such translation mechanisms may be made very precise, and may be configured to be computer-controlled. Optionally an imaging device housing or body may come in multiple parts. The multiple parts may be threaded and/or configured to engaged in a manner that adjusts one or more dimension of the device housing or body, or an optical path length. In some embodiments, the focusing mechanism 214 may further include a focus lock 215. The focus lock may prevent the housing from coming apart completely, or may provide limits to the degree that the housing dimension and/or optical path length can be varied. The focus lock may provide limits to the degree of focusing that may occur. Such limits may be provided in a single direction or multiple directions (e.g., reduced optical path length, increased optical path length).

Embodiments of the miniaturized imaging device 201 may have an FOV of, for example, 900 μm×700 μm (at middle of focal range), and may provide an average resolution over FOV of about 1.5 µm, wherein the resolution limit of the image sensor 213 may be, for example, on the order of 1.2 µm. In some embodiments, the FOV may be greater than, less than, or equal to about 0.01 mm$^2$, 0.02 mm$^2$, 0.05 mm$^2$, 0.07 mm$^2$, 0.1 mm$^2$, 0.15 mm$^2$, 0.2 mm$^2$, 0.3 mm$^2$, 0.4 mm$^2$, 0.5 mm$^2$, 0.7 mm$^2$, 1.0 mm$^2$, 1.2 mm$^2$, 1.5 mm$^2$, 2 mm$^2$, 2.5 mm$^2$, 3 mm$^2$, 3.5 mm$^2$, 4 mm$^2$, 5 mm$^2$, 7 mm$^2$, or 10 mm$^2$. The average resolution may be up to about 250 nm, 300 nm, 500 nm, 700 nm, 1 µm, 1.2 µm, 1.5 µm, 2 µm, 2.5 µm, 3 µm, 3.5 µm, 4 µm, 5 µm, 7 µm, 10 µm, 15 µm, 20 µm, 25 µm, 30 µm, 40 µm, 50 µm, 100 µm, 150 µm, 200 µm, 250 µm, 300 µm, 400 µm, 500 µm, or 700 µm. Any combination of FOV and resolution may be provided. The system imaging resolution can be controlled based on image sensor pixel size (e.g., CMOS sensors with 640×480 pixels=0.3 megapixels, less than 0.3 megapixels, up to 1 megapixels, up to 2 megapixels, up to 3 megapixels, more than 3 megapixels), and/or optical system magnification. In some embodiments, a high degree of resolution may be provided without relying too heavily on optical magnification. For example, the resolutions described may be attained while the optical magnification does not one or more of the following: 1x, 1.5×, 2×, 2.5×, 3×, 4×, 5×, 6×, 7×, 8×, or 10×. In some embodiments, the signal-to-noise (SNR) ratio (i.e., with increasing SNR, controlled for example through signal processing techniques known in the art, corresponding to improved resolution) may be controlled. The SNR may affect effective system imaging resolution (e.g., with deconvolution-based image processing techniques used during post-processing). The overall resolution limit of the device may yield, for example, less than 300 nm, 250 nm, 200 nm, 150 nm, 100 nm, 50 nm, 10 nm or less than about 1 nm precision, depending on imaging technique and image sensor resolution. The overall resolution may be provided at a cellular or subcellular level. In some embodiments, at a subcellular level, details of cells, such as dendrites (e.g., dendritic spines) can be visible.

In some embodiments, the high resolution may be achieved with aid of a short optical path. For example, the distance from a target area to the objective 203 may be less than or equal to 10 mm, 5 mm, 3 mm, 2 mm, 1.5 mm, 1 mm, 0.5 mm, 0.1 mm. Optionally a distance of an optical path from a light source 208 to the objective 203 (e.g., illumination pathway) may be less than or equal to 30 mm, 25 mm, 20 mm, 15 mm, 12 mm, 10 mm, 5 mm, 3 mm, 2 mm, 1.5 mm, 1 mm, 0.5 mm, 0.1 mm. A distance of an optical path from an objective 203 to the image sensor 213 may be less than or equal to 30 mm, 25 mm, 20 mm, 15 mm, 12 mm, 10 mm, 5 mm, 3 mm, 2 mm, 1.5 mm, 1 mm, 0.5 mm, 0.1 mm. An image collection pathway from a target to the image sensor may be less than or equal to 30 mm, 25 mm, 20 mm, 15 mm, 12 mm, 10 mm, 5 mm, 3 mm, 2 mm, 1.5 mm, 1 mm, 0.5 mm, 0.1 mm. In some instances, the maximum length of the image collection pathway, even when the image collection pathway is adjusted, may be less than or equal to 30 mm, 25 mm, 20 mm, 15 mm, 12 mm, 10 mm, 5 mm, 3 mm, 2 mm, 1.5 mm, 1 mm, 0.5 mm, 0.1 mm.

Figure 8A:
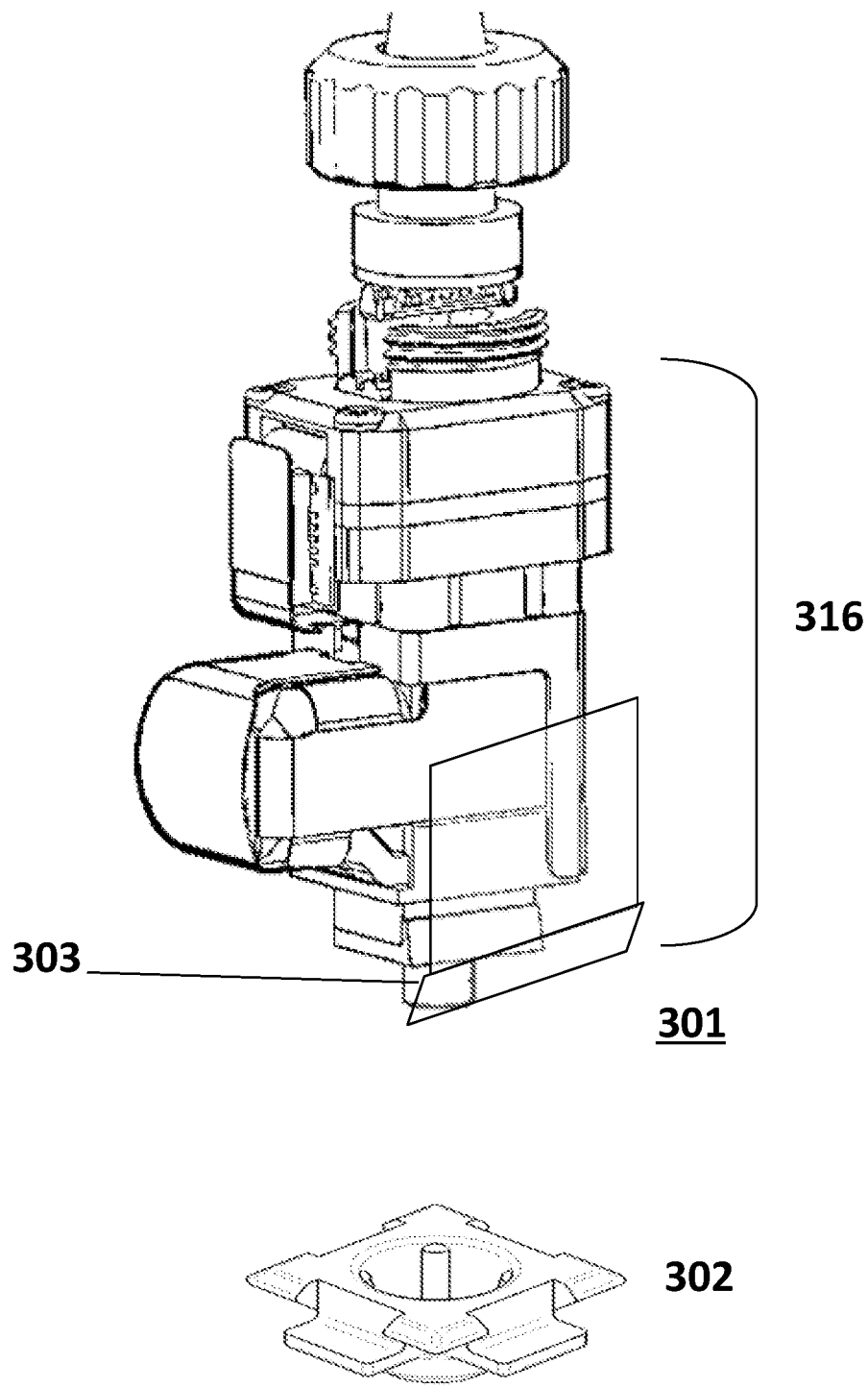
FIG. 8A is an exploded perspective side view of a magnetic quick-release baseplate for microscope attachment.

FIG. 8A is an exploded perspective side view of an embodiment of a miniature microscope 301 with a quick-release baseplate 302 for microscope attachment. An objective 303 may be located on a microscope body 316 and may be configured to protrude from the body into an opening provided on the baseplate 302. In some instances, the body may be attached to the baseplate in limited numbers of configurations based on the alignment of the partial-cylinder bumps. The body may automatically snap to the appropriate alignment with the baseplate in accordance with release of the spring clips. In some embodiments, the attachment mechanisms between the body 316 and the baseplate 302 may permit quick attachment and/or release between the body and the baseplate. In some embodiments, no separate fasteners or components are required to attach the body to the baseplate. The device body may be attached to the baseplate with aid of the magnets alone. Alternatively, the device body may be attached to the baseplate with only the aid of the magnets and/or one or more integral mechanical shape or feature of the baseplate and/or body. The attachment mechanisms may be inherent to the body and the baseplate morphology or magnetic qualities. The quick attachment and/or release may be performed without requiring extra tools. A user may be able to attach or release the body from the baseplate only using the user's hand.

Figure 8B:
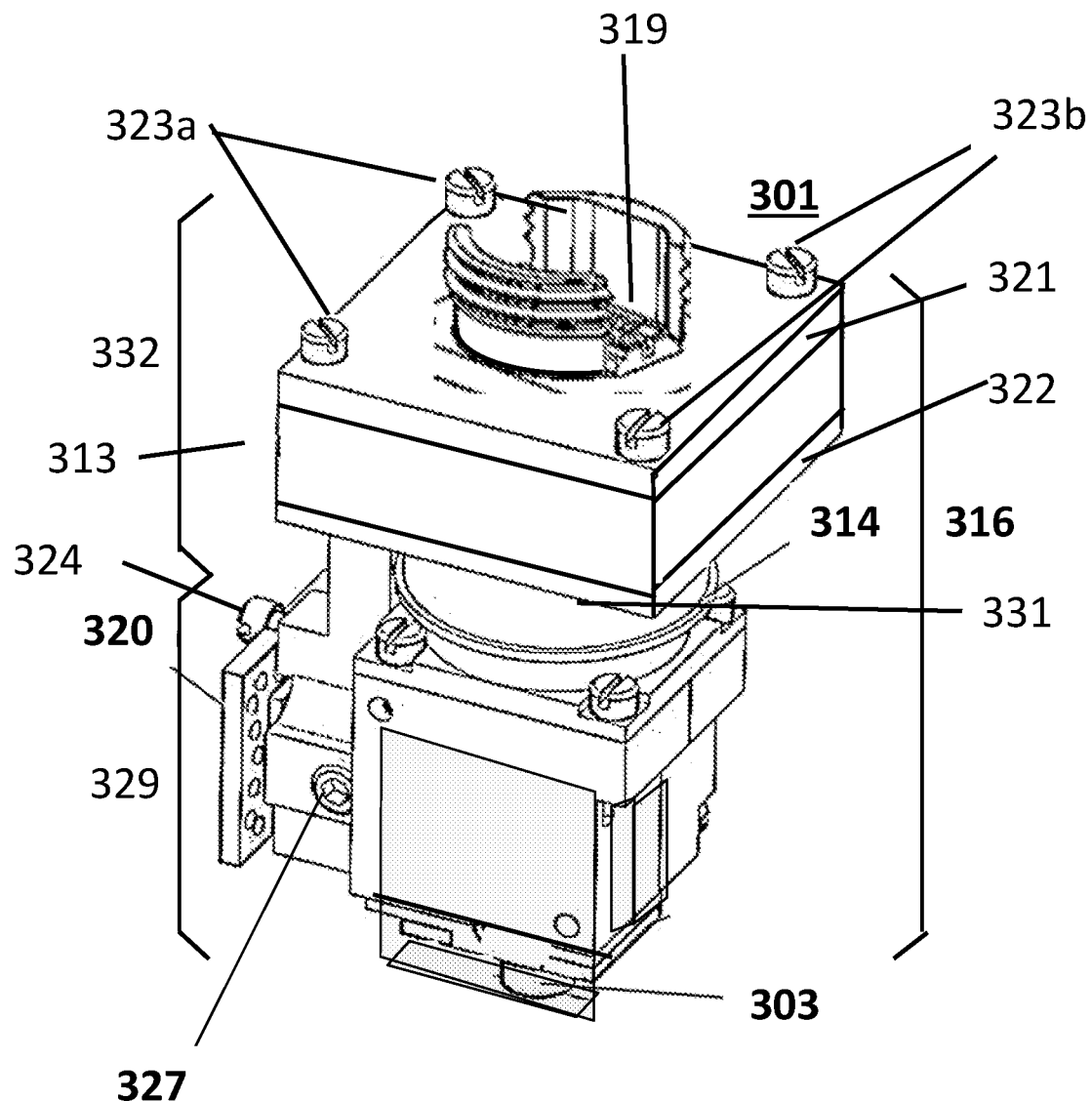
FIG. 8B is a perspective side view of a miniaturized imaging device with a quick-release base plate.
Figure 8B:
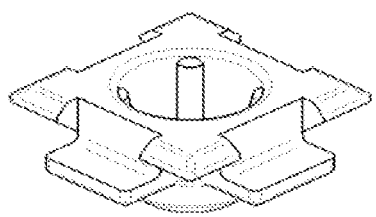

FIG. 8B is a perspective side view of an exemplary miniature microscope 301. A connector or jack 319 may be provided on the microscope body 316 to enable wires, cables and/or other communications means to be connected to an image sensor 313. The connector or jack 319 may be a mechanical reinforcement structure for the cable and attachment point for various components, such as heat shrink tubing, that provides additional mechanical reinforcement. A ventilation grid 320 may be provided on the body 316 adjacent to a light source (not shown). The ventilation grid may be a heat sink. The ventilation grid may be made from a heat conductor material such as, for example, copper in order to ensure adequate heat transfer from the light source to the surrounding air. In some embodiments, the microscope may be outfitted with a fan or other convective mechanism to enhance the heat transfer rate from the light source.

The image sensor may reside between protective housing pieces 321, 322. The housing 322 may have an opening to allow for the wires, cables and/or other communications means to be connected to the image sensor 313. A secure fit of the image sensor may be ensured, for example, through mechanical compression of the pieces 321, 322 by one or more screws 323a, 323b fastener in threaded holes (not shown) provided in the housings 321, 322. The holes may be through holes (e.g., in housing 322). Alternatively, the holes may partially extend though the housing and may not be through holes. In one example, the housing 322 may have through holes while the piece 321 may have through holes or only partially extended (e.g., blind) holes. Additional threaded connections may be employed in the assembly of the microscope body 316, including, for example, one or more screws 324 for holding an illumination source in place, screws for attaching a modular component containing a lens (e.g., tube lens, achromat 212) and/or part of a focusing mechanism and/or other part of a collection pathway, screws 324 for enhancing the mounting and alignment of components within the microscope body. The microscope body, baseplate and/or members/modules thereof may be assembled using one or more other mechanical, magnetic or adhesive attachment means described herein. These attachment means may be used in addition to, or as a replacement of one or more of the threaded attachment means on the microscope 301. In some cases, no threaded attachment means may be used to assemble the miniature microscope.

In one embodiment, the quick-release baseplate 302 may have a width of 7.1 mm, a depth of 7.0 mm and a height of 2.5 mm. In other embodiments, the dimensions of the baseplate may be in the range of 4-10 mm width (e.g., 4 mm, 6 mm, 8 mm, 10 mm width), 4-10 mm depth (e.g., 4 mm, 6 mm, 8 mm, 10 mm depth) and 1-5 mm height (e.g., 1 mm, 3 mm, 5 mm height). In accordance with further miniaturization of the device, the baseplate may be made of a size of less than 1 mm in any direction (e.g., less than 0.5 mm, 0.25 mm or 0.1 mm width and/or depth, and less than 0.05 mm, 0.025 mm or 0.01 mm height). In some embodiments a maximum dimension (e.g., greatest of width, depth, or height) of the baseplate may be less than or equal to 5 cm, 4 cm, 3.5 cm, 3 cm, 2.5 cm, 2 cm, 1.5 cm, 1.2 cm, 1 cm, 9 mm, 8 mm, 7 mm, 6 mm, 5 mm, 4 mm, 3 mm, 2 mm, or 1 mm. The baseplate may weigh 5 grams or less, 4 grams or less, 3 grams or less, 2 grams or less, 1.5 grams or less, 1 gram or less, 0.5 grams or less, 0.3 grams or less, or 0.1 grams or less.

A quick-release baseplate 302, such as spring-clip quick release baseplates, may be particularly advantageous in enabling chronic experiments. The spring-clip baseplate 302 may provide precise, repeatable mounting of the microscope body 316 to a test subject (e.g., the subject's head) for chronic experiments without requiring the use of anesthesia to immobilize the subject. Side walls on the baseplate 302 may restrict lateral linear motion and any rotation of the microscope body so that only force directly opposing the normal force provided by the magnets may separate the microscope body from the baseplate (e.g., directly up or perpendicular from the surface to which the baseplate 302 is mounted). Additionally, fit adjustment features 327 (e.g., set screws, elastomeric components or retaining springs) may ensure a snug fit between the microscope body and the side walls of the baseplate.

The quick-release configuration enables easy removal of the body 316 from the baseplate 302. For example, the body may be simply pulled off from the baseplate, and then instantaneously re-attached using the automatic mounting and alignment enabled by the quick-release mechanism. In some embodiments, re-attachment may require manual adjustment, while removal may involve simply pulling the microscope body off the baseplate. In alternate configurations, the quick-release mechanism may require that a button, spring or other mechanical release feature be pushed or activated in order to release the body from the baseplate. In yet other configurations, the microscope body may automatically release itself from the baseplate (e.g., using remote control of electromagnets to control the magnetic force, using degradable mechanical linkages that break off after being subjected to a predetermined amount of mechanical stress exerted during movement of the test subject).

The quick-release mechanism may also include multi-step/staged release or multi-step/staged attachment. The microscope body may be removed from the baseplate in several steps including, but not limited to, pressing a release feature, followed by twisting or pulling the body 316 off the baseplate 302, releasing multiple attachment means (e.g., pressing multiple release buttons), removing a latch, pin or other fastener prior to pulling off the body, etc. Analogously, attachment may also be performed as a sequence of steps. The release and/or attachment mechanism may also be staged. In one example, the microscope body may be partially released from its position before eventually disconnecting either automatically or through mechanical means. For example, electromagnets may be first turned off, causing the microscope body to twist on a hinge while remaining attached to the baseplate. The next release stage may lead to permanent disconnection of the microscope body from the baseplate, for example through manual release of a connector. In other cases, the quick-release mechanism may involve a procedure wherein the microscope body is pressed toward the baseplate before it can be pulled off. For example, the body may need to be pressed toward the baseplate to twist, unlock and or otherwise release a fastener (e.g., spring-loaded feature) prior to detachment. Further, in some cases, the body may be removed, and one or more features on the body and/or the baseplate may need to be reset (e.g., pulling back a spring-loaded slot or trap feature). The release and/or attachment may also require that additional or replacement parts be supplied. For example, one or more mounting/alignment members may need to be replaced after each removal (e.g., a mechanical member that must break in order for the body to detach).

Benefits of the quick-release configuration include, but are not limited to, enabling the baseplate to remain attached on the body of a subject for long term study, easy removal of the microscope body to provide relief to the subject from carrying load while at the same time enabling processing and/or reconfiguring of the microscope body prior to re-attachment, repeated imaging of the same subject (e.g., live being) without the need anesthesia or sacrifice, and enabling imaging during conscious activity.

The microscope body 316 may comprise a body portion 329 and a focusing unit 332. In some embodiments, a microscope body may comprise an illumination unit which may comprise a housing 330 inside which may reside, for example, one or more optics module, an objective module and one or more mounting/alignment members including, for example, the steel plates 317. A flanged mounting/alignment member 331 may be mounted to the housing 330 using threaded attachment means. The mounting/alignment member 331 may have a male tubular threaded portion. The tubular threaded portion of the mounting/alignment member 331 may receive a female threaded portion of a focusing unit 332. The female threaded portion may constitute a portion of the housing of the focusing unit 332. The female threaded portion may have a flange 321.

At least a fraction of the optical elements (e.g., condenser lens, dichroic mirror, and filter elements) that direct the imaging and/or stimulation light to the sample can be outside of an optical path that directs light emission from the sample to the image sensor. Placing at least a fraction of the optical elements that direct the imaging and/or stimulation light to the sample outside of the optical path between the sample and the image sensor can increase the efficiency of light transfer from the sample to the image sensor. Providing a high efficiency transfer of light from the sample to the image sensor can permit relatively low power density levels of imaging light to be delivered to the sample.

The microscope system described herein can simultaneously image and stimulate at least a portion of a sample without cross talk between the imaging light and the stimulation light. Cross talk can occur when the imaging light accidentally stimulates at least a portion of the sample such that the stimulation is not entirely controlled by the stimulation light only. Similarly cross talk can occur when the stimulation light reflects off the sample and/or causes fluorescence of the sample and causes stray light to be delivered to the image sensor.

The number of photons delivered to the sample per unit area required to generate an image of the sample can be minimized or reduced by optimizing the efficiency of the light collection path between the sample and the image sensor. Reducing the power density of the imaging light directed to the sample can decrease the probability of accidentally stimulating the target object with the imaging light. The low level of imaging light relative to the stimulation light can minimize cross talk between the imaging and stimulation light. Cross talk can occur when imaging light inadvertently stimulates one or more portions of the sample.

The portion of the sample (e.g., opsin) that is stimulated by the stimulation light can be similarly stimulated by the imaging light if the power density of the imaging light exceeds a predetermined threshold. This predetermined threshold hold can be decided by a variety of factors including the type of opsin, the concentration of the opsin in the cell membrane, and the wavelength of the imaging light. A user may want to reduce the probability of unintentionally stimulating one or more portions of the sample by the imaging light while intentionally providing stimulation light to one or more portions of the sample. The systems and methods described herein provide an efficient optical path with few optical elements between the sample and the image sensor that permits use of low levels (e.g., power density) of imaging light. The level of imaging light used in the system described herein can be below a level that stimulates one or more portions of the sample.

In some cases the stimulation light source and the imaging light can be provided at substantially the same power. Cross talk between the stimulation light source and the imaging light source at substantially the same power can be reduced by spectral separation of the stimulation light source and the imaging light source. Alternatively or additionally, cross talk between the imaging light source and the stimulation light source can be reduced with a filter array. Alternatively or additionally, cross talk between the imaging light source and the stimulation light source can be reduced with baffles configured to physically separate the light from the light sources.

Emission from the sample can be collected by one or more light detectors (e.g., pixels) of the image sensor to generate an electronic representation of an image of the sample. In some cases, the emission can be a fluorescence emission stimulated by the imaging light. Stimulation light can reflect off of the sample and/or induce fluorescence emission which can cause cross talk between the imaging light and the stimulation light during imaging. Cross talk from reflection and/or fluorescence from the stimulation light can be reduced or eliminated by providing spectral separation between the imaging light and the stimulation light. In some cases, the imaging light and stimulation light incident on the sample can be spectrally separated by providing the imaging light at a first wavelength and the stimulation light at second wavelength that is substantially higher or lower than the first wavelength. In some cases, the discrete wavelength or range of wavelengths of the imaging light and the discrete wavelength or range of wavelengths of the stimulation light can be spectrally separated by at least about 5 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm. In some cases, the spectral separation between the imaging light and the stimulation light can be less than 5 nm. The spectral separation between the imaging light and the stimulation light can fall between any of the values listed herein.

Figure 13:
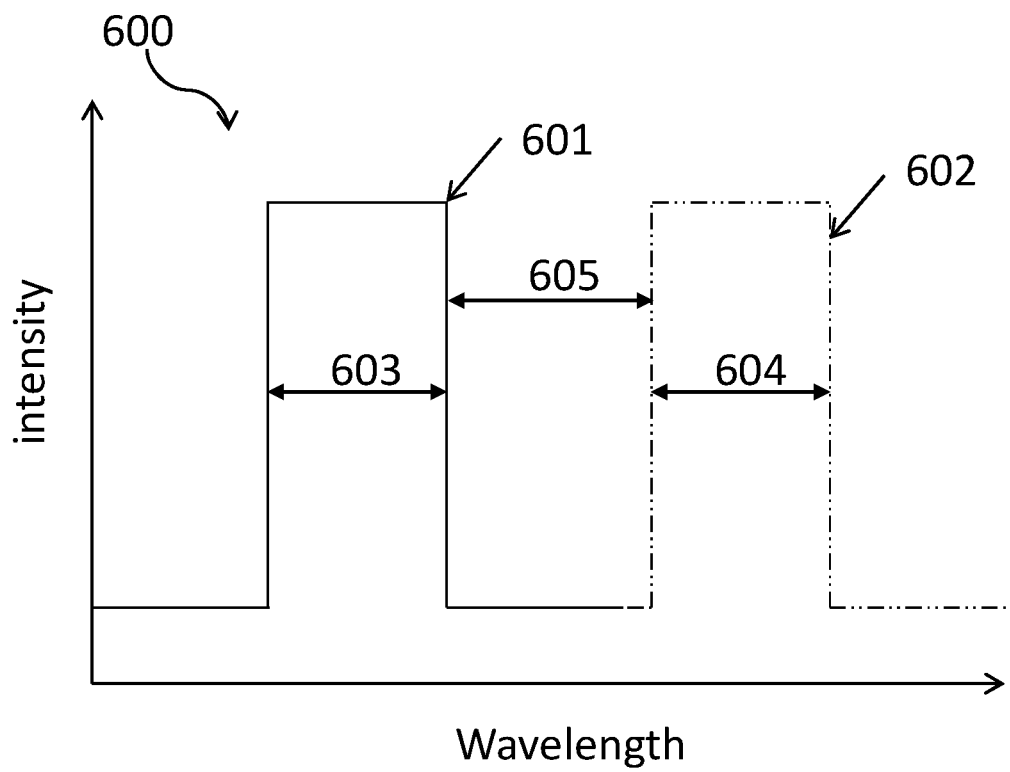
FIG. 13 shows possible emission spectra as a function of wavelength for the imaging and stimulation light source.
Figure 13:
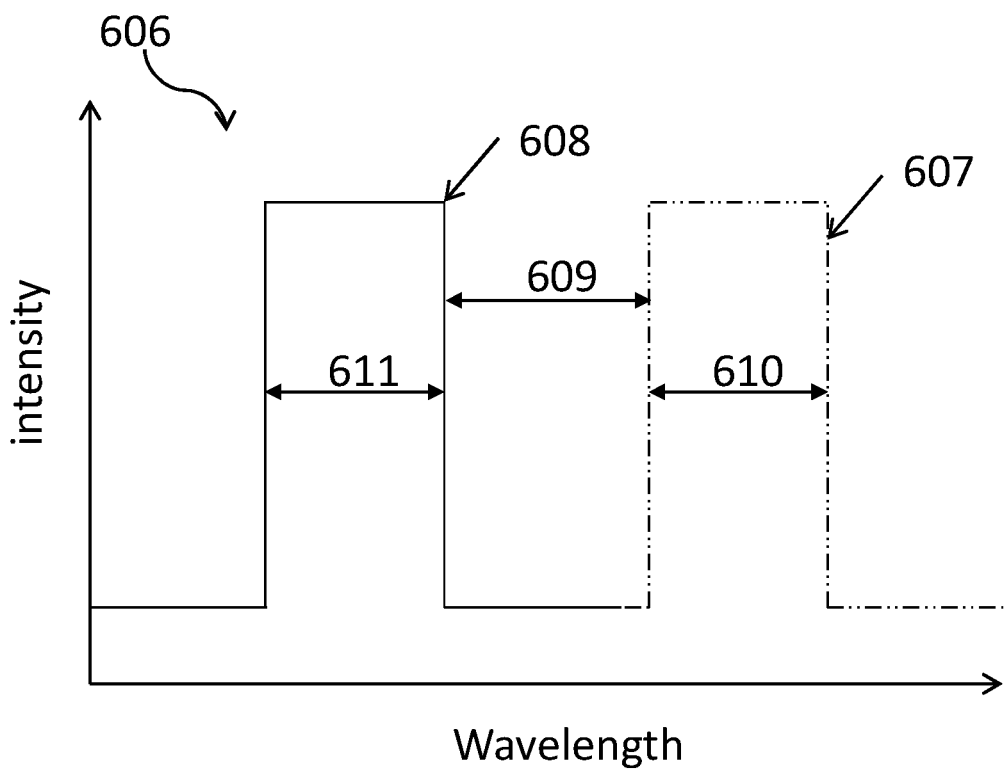

A wavelength of an emission (e.g., fluorescence) emitted by the sample in response to the imaging light can be a function of a known wavelength of the incident imaging light such that a filter can be used to separate light that is not within the expected wavelength range before the light is detected by the image sensor. In some cases, the light that is outside of the expected range can be unwanted emission from the sample caused by the stimulation light. Different filters can be used for different samples or different types of imaging studies such that the discrete wavelength or range of wavelengths of the imaging and/or stimulation light can be varied. In some cases, the imaging light (e.g., fluorescence excitation light) can be provided at a wavelength of about 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, or 2000 nm. The imaging light can be provided at a wavelength greater than the values listed, less than the values listed, or at a value between any of the values listed. In some cases, the stimulation light (e.g., optogenetic stimulation light) can be provided at a wavelength of about 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, or 2000 nm. The stimulation light can be provided at a wavelength greater than the values listed, less than the values listed, or at a value between any of the values listed. The imaging light can be provided over a range of wavelengths. The stimulation light can be provided over a range of wavelengths. The range of wavelengths of the imaging light can be larger compared to the range of wavelengths of the stimulation light. Alternatively, the range of wavelengths of the imaging light can be smaller compared to the range of wavelengths of the stimulation light. In some cases, the range of wavelengths of the imaging light and the range of wavelengths of the stimulation light can have at least a fraction of overlapping range. FIG. 13 shows a graphical example of a spectrally separated imaging light and stimulation light. The graphs 600 and 606 each show intensity as a function of wavelength. In graph 600, the imaging light 601 emits light at a shorter wavelength range than the stimulation light 602. For example, the imaging light can emit in a first range of wavelengths 603. The stimulation light can emit in a second range of wavelengths 604. A gap 605 can be provided between the first range of wavelengths 603 and the second range of wavelengths 604. In graph 606, the imaging light 607 emits light at a longer wavelength than the stimulation light 608. For example, the imaging light can emit in a first range of wavelengths 610. The stimulation light can emit in a second range of wavelengths 611. A gap 609 can be provided between the first range of wavelengths 610 and the second range of wavelengths 611.

In some cases, the power density of the imaging light required for imaging can be further reduced by providing close proximity between an optical source of imaging (e.g., excitation) light and the sample. For epi-fluorescent imaging, the interaction between the imaging light and the sample causes the generation of fluorescence emission from the sample. The imaging light can be directed toward the target object and may have a specific wavelength configured for absorption by fluorophores, fluorescent markers or fluorescent probes. The fluorophores then emit light at different (e.g., longer) wavelengths. Different fluorophores can emit light at different wavelengths (e.g., colors). The amount of absorbed light can be related to the power density of the imaging light delivered to the target object. In this manner, the amount of fluorescence generated is correlated to the power density of the imaging light. Although various light delivery mechanisms can help reduce the attenuation of light as it travels through a medium, the attenuation of light will increase as distance of travel through a medium increases. Also, when using air and other mediums, the composition of the medium and other dispersive attributes can play significant roles in the delivery and/or attenuation of the light. In some instances, the microscope system can be designed to permit the imaging light to be arranged in close proximity to the sample, thereby facilitating the use of a relatively low power imaging light source. In some cases, a linear distance between the optical source of the imaging light and the target object (e.g., the tissue-to-imaging light source path length) can be at most about 5 cm, 2 cm, 1 cm, 5 mm, 1 mm, 0.1 mm, 0.01 mm, 0.001 mm, 0.0005 mm, or 0.0001 mm.

Similarly, image resolution can be dependent on the amount of light transmitted from the sample to the image sensor. In some cases, a linear distance between the sample and the image sensor (e.g. the tissue-to-image sensor path length) can be at most about 5 cm, 2 cm, 1 cm, 5 mm, 1 mm, 0.1 mm, 0.01 mm, 0.001 mm, 0.0005 mm, or 0.0001 mm. A linear distance between an objective lens that focuses light emitted from the sample and the image sensor can be at most about 5 cm, 2 cm, 1 cm, 5 mm, 1 mm, 0.1 mm, 0.01 mm, 0.001 mm, 0.0005 mm, or 0.0001 mm. A linear distance between an objective lens focal plane and the image sensor can be at most about 5 cm, 2 cm, 1 cm, 5 mm, 1 mm, 0.1 mm, 0.01 mm, 0.001 mm, 0.0005 mm, or 0.0001 mm.

Various fluorescence sources can be used consistent with one or more embodiments discussed herein. The mention of a particular source of fluorescence does not necessarily preclude use of other sources of fluorescence (e.g., genetically-encoded fluorescent proteins, such as GFP, GCaMP, mCherry, and variants thereof).

Embodiments of the present disclosure relate to a microscope device and system that captures image data for a relatively large field-of-view, the image data providing high resolution of a sample. The field-of-view can be at least about 0.1 mm$^2$, 0.2 mm$^2$, 0.3 mm$^2$, 0.4 mm$^2$, 0.5 mm$^2$, 1 mm$^2$, or 5 mm$^2$. The entire field-of-view can be imaged at once. Stimulation light can be directed to any portion of the field-of-view or the entire field-of-view. The entire field-of-view can be imaged at once without dividing the field-of-view into subsets and scanning each subset individually to image the entire field-of-view. The entire field-of-view can be simultaneously captured at a high resolution. The entire field-of-view can be simultaneously captured with a resolution of at least about 0.1 µm, 0.5 µm, 1 µm, 2 µm, 3 µm, 4 µm, 5 µm, 10 µm, 20 µm, 30 µm, 40 µm, or 50 µm. The resolution can be sufficient to identify one or more cells in an image captured in the microscope system. The resolution can be sufficient to identify one or more cellular structures in an image captured by the microscope system. The resolution can be sufficient to identify one or more dendrites in an image captured by the microscope system. The resolution can be sufficient to identify one or more nerve cell axons in an image captured by the microscope system. The relatively large field-of-view can permit a user to stimulate two or more cells or cell populations in the same field-of-view to observe an interaction of the stimulated cells or cell populations.

The entire field-of-view can be imaged by processing of light from the sample directed to the image sensor. The image sensor can comprise an array of sensor elements or pixels, which is provided to image the field-of-view. The sensor elements detect light emission from the sample for different portions of the field-of-view. The sensor elements can be monochrome light detectors. The sensor elements can detect light in one or more predetermined wavelength ranges. The sensor elements can be configured with sufficient sensitivity and proximity to the sample to facilitate image capture and generation of at least a portion of the sample.

In some cases, operation of the microscope system described herein can generate heat within the microscope system. Internal resistance from one or more electronic circuit elements and/or one or more light sources can generate heat causing a surface temperature of the one or more optical elements, the microscope housing, or other components in thermal communication with the microscope system to increase. In some cases, the microscope system can be on or near a living tissue. This generated heat can place limits on a duration of time that the microscope can be used. The generated heat can be transferred to the living tissue can cause the living tissue to heat up. The living tissue can be heated to a temperature above which tissue dies, burns, decomposes, oxidizes, or otherwise degrades. In some cases, the generated heat can influence cellular activity and lead to observations that can confuse the results of an optogenetic experiment. Some cells may be more active at elevated temperatures such that the elevated temperatures result in observed cellular activity caused by the generated heat instead of the stimulation light. In some cases, one or more cooling fins, heat sinks or heat pipes can be placed on the microscope to remove the generated heat by radiation, conduction and/or convection. The cooling fins, heat pipes, or heat sinks can prevent and/or reduce heat transfer from the microscope system to the living tissue.

In some cases, the microscope can operate with relatively low optical magnification with high-resolution imaging of a field-of-view for one or more samples of small size. The magnification can be at most about 1000×, 500×, 100×, or 50×, 10×, 8×, 5×, 4×, 3×, 2×, 1.5×, or 1×. The low level of magnification may enable the microscope to attain a high level of resolution for the field-of-view as described elsewhere herein. A high level of resolution can be attained by the microscope system using a relatively low magnification. The maximum magnification capability of the optical magnification required for a particular level of imaging can be lessened through the careful design and application of a microscope device and system consistent with various aspects discussed herein.

The microscope system described herein permits real-time simultaneous imaging and stimulation of one or more portions of a sample using a microscope device and/or system consistent with aspects discussed herein. The microscope system can facilitate in vivo or in vitro real-time simultaneous imaging and stimulation of target objects. For instance, in vivo imaging and stimulation of a live subject can be particularly useful for correlating external stimuli and other factors with the captured images. This correlation can be used, for example, as a diagnostic/research tool by associating properties of the captured images with the external stimuli. Real-time imaging at high frame rates can further provide such correlation as a function of time.

The microscope system can permit a user to direct imaging light to a sample to image the sample and detect one or more portions of a sample that the user would like to stimulate. The user can then provide stimulation light to the one or more portions of the sample detected with the imaging light. The user can continue to observe the sample while the stimulation light is delivered to the one or more portions of the sample in real time. In an example, the user can observe a neural circuit in the sample with the microscope system. The user can direct stimulation light to a portion of the neural circuit and observe a response of one or more other portions of the neural circuit in real time. In some cases, the user can provide stimulation light to inhibit activity in one or more portions of the sample. The user can observe activity using the imaging light from the microscope system. When the user observes the activity the user can provide stimulation light to at least a portion of the sample to inhibit the activity. In an example, the user can observe activity between two or more neuron populations that is indicative of pre/early seizure activity. The user can provide stimulation light to the one or more neuron populations to prevent or ease the seizure.

The microscope device and/or system can have a modular design that facilitates detaching and reattaching various components of the microscope device. The detachment and reattachment can be used to replace the modular components with new and/or different modular components. For instance, a light source can be replaced with a new light source having the same or different optical and/or electrical properties. Either or both of the stimulation light source and the imaging light source can be replaceable. The array of optical sensors and/or the optical direction elements (e.g., mirrors, filters and lenses) can also be removed and replaced. If desired, the optical sensor can also be removed and replaced.

The microscope system can include a synchronization circuit for interfacing to an external optical-data processing (recording and/or configuring) system. The synchronization circuit includes logic circuitry (e.g., a programmable or semi-programmable chip (microcontroller or ASIC) that is configured and arranged to communicate a frame reference/ active signal. The synchronization circuit can include a field programmable gate array (FPGA). The synchronization circuit can include an ARM based microcontroller. In a typical application, a frame active signal would provide synchronization information, e.g., as defined in an IEEE communications standard, for and with the data communicated between the microscope system and the external system. Such an optical-data recording/configuring system can be used to install software, configure set-up parameters for experiments and procedures, provide visual feedback during such experiments and procedures, and record the optical data for manipulation and further study. The external optical-data processing (recording and/or configuring) system can be configured to control the stimulation light source as described elsewhere herein.

Certain of the disclosed devices and systems may include a baseplate acting as a foundational structure which provides support/stability and also allows for microscope or optical probe (re)alignment. For example, FIG. 1 and FIG. 2 provide features of such an embodiment. In yet further embodiments the instant disclosure is directed to methods of using the image devices which are described herein. These methods include the steps of attaching and reattaching the microscope or optical probes to the baseplate for allowing the microscope or optical probe alignment to be precise. Such precision should be sufficient for repeated imaging of a common imaging location, e.g., during chronic experiments. The baseplate can be attached to a living organism. The baseplate can attach to the head of a living organism. The baseplate can attach to the skull of the living organism. In some cases, the baseplate can remain attached to the living organism while the microscope is removed from the baseplate. The baseplate can be attached to the living organism with a helmet, belt, and/or harness.

Microscope systems described herein are useful in experimental settings. In some cases, the microscope provides less disruption to freely-moving subjects (e.g., rodents) than other imaging techniques. Handling of a laboratory subject may cause that subject to experience anxiety. By allowing for one handed secure attachment, the microscope-baseplate kinematic coupling mechanism reduces the amount of time spent handling rodents during experiments. The small size of the microscope described herein similarly reduce disruption experienced by the subjects.

In some cases, the microscope can be configured to simultaneously stimulate a portion of the sample and image (e.g., observe) a portion of the sample. The portion of the sample can comprise an object of interest. The object of interest can be an object that can be stimulated and/or deactivated by light energy. The object of interest can be one or more cells. The object of interest can be one or more nerve cells (e.g., neurons). A chosen one or more cells can be stimulated or deactivated by genetically loading light activated channels (e.g., opsins) into a cellular membrane of the chosen one or more cells. In some cases, the light activated channels can be activated by light of a specified wavelength and/or intensity. The wavelength of the stimulation light source can be modulated to activate different light activated channels.

Figure 9A:
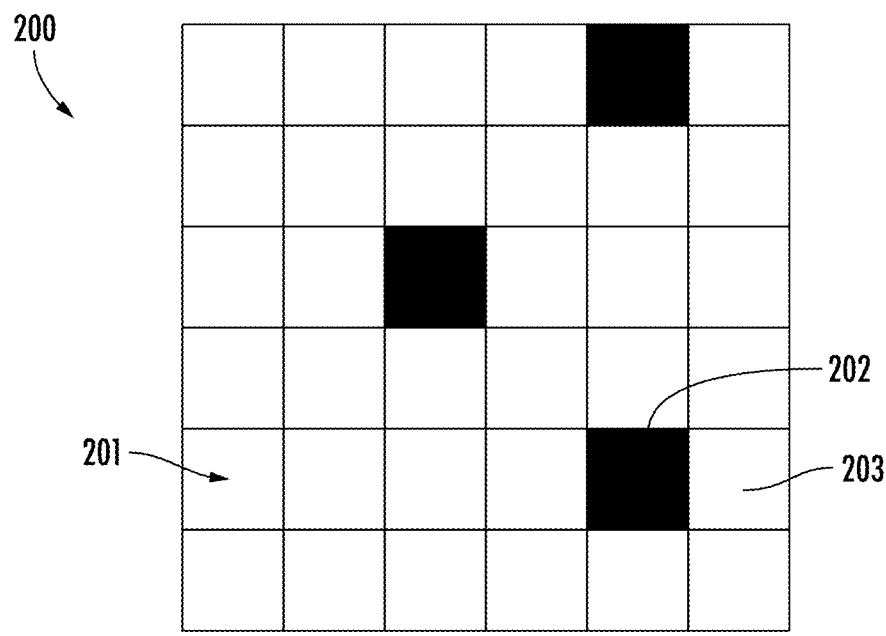
FIG. 9A shows a schematic of a stimulation light source comprising a plurality of light sources.

The stimulation light source can be a single light source. Alternatively, the stimulation light source 200 can comprise an array of light sources 201 as shown in FIG. 9A. The stimulation light source 200 can have an area of at least about 1 square micron, 5 square microns, 10 square microns, 50 square microns, 100 square microns, 0.001 square mm, 0.01 square mm, 0.1 square mm, 1 square mm, 5 square mm, 10 square mm, or 50 square mm. The stimulation light source 200 can comprise an array of 1×n light sources 201 where n can be an integer from 1 to 1000. In some cases the stimulation light source can comprise a matrix of m×n light sources where m can be an integer from 1 to 1000 and n can be an integer from 1 to 1000. In some cases, a matrix of light sources can permit stimulation of an individual cell, portion of a sample, or object. The matrix of light sources can permit stimulation of an individual neuron or an individual population of neurons. The light sources can be light emitting diodes (LEDs). The light sources can be organic light emitting diodes (OLEDs). The light sources can be micro-LEDs. The light sources can be high-power LEDs. The light sources can be directed through a spatial light modulator. The light sources can include light patterned through a coupled fiber bundle. The light sources can include a pattern of laser diodes. In some cases, the high-power LEDs can emit light with a power of at least about 0.1 W, 0.25 W, 0.5 W, 0.75 W, 1 W, 2 W, 3 W, 4 W, 5 W, 10 W, 15 W, 20 W, or 25 W.

The stimulation light source can be in communication with a controller. The stimulation light source can be in communication with a controller through a wired or wireless connection. The controller can be on-board or off board the microscope. The controller can comprise one or more processors programmed to control the stimulation light source. One or more of the stimulation light sources in the matrix or array can be turned on by the controller to provide stimulation light to a specified location on the target object in order to deliver stimulation light to an object of interest (e.g., cell). FIG. 9A shows a stimulation light source 200 with a plurality of turned on light sources 202 and a plurality of turned off light sources 203. Any number of light sources can be turned on in the stimulation light source. For example, zero, one, two, three, four, five, or more light sources can be turned on in the stimulation light source 200. Any number of light sources can be turned off in the stimulation light source. For example, zero, one, two, three, four, five or more light sources can be turned off in the stimulation light source 200. The stimulation light sources can be turned on in a pattern in order to deliver stimulation light to a specified region of the target object, for example to the one or more objects of interest. The one or more processors can be programmed to determine the pattern in which the one or more light sources should be turned on and off in order to deliver stimulation light to a specified region of the target object. The one or more processors can receive an image of the target object from the microscope as an input when determining the pattern. In an example a sample can comprise a plurality of nerve cells. A user can stimulate a single nerve cell in the sample without stimulating adjacent nerve cells by delivering stimulation light only to a fraction of the sample. A user can observe a reaction of the other unstimulated nerve cells to the one stimulated nerve cell.

Figure 9B:
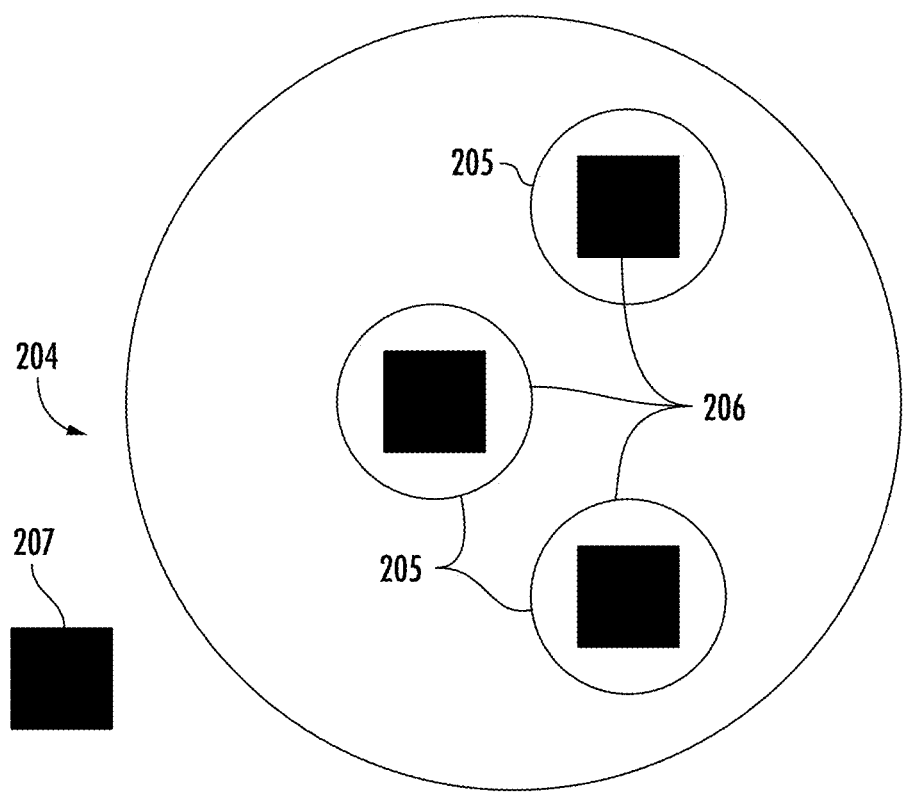
FIG. 9B shows a schematic of a field-of-view imaged by the microscope system, said field-of-view comprising a plurality of objects of interest upon which stimulation light is incident.

FIG. 9B shows a field-of-view 204 comprising the sample that can be imaged by the microscope system. The field-of-view 204 can comprise one or more objects of interest 205. The objects of interest 205 can be objects that respond to the stimulation light source. The objects of interest can be cells. The object of interest can be nerve cells. Stimulation light 206 can be incident on the objects of interest 205. The stimulation light can be incident on two or more objects of interest 205 simultaneously. The stimulation light can be incident on at least a fraction of the field-of-view 204. The stimulation light can be incident on at least about 1%, 5%, 10%, 20%, 30%, 40%, 50%, 60%, or 70% of a sample or a portion of a sample contained in the field-of-view 204. Imaging light can be provided to the field-of-view 204 while the stimulation light is provided to the one or more objects of interest 205 such that the reaction of the one or more objects of interest 205 to the stimulation light can be imaged. While the stimulation light 206 is shown to be smaller than the objects (e.g., cells) 205 that are being stimulated in FIG. 9B, it is to be understand that the stimulation light can be either smaller or larger than the objects of interest.

Alternatively or in addition, the stimulation light 207 may be incident on portions of the sample outside of the field-of-view. For example, the stimulation light may be incident on a different portion of the sample than the imaging light. For example, the field-of-view (e.g., imaging field-of-view) may be displayed (e.g., on a display) for observation by a viewer while stimulation light is incident on a different portion of the sample that is not displayed. In some instances, the stimulation light may stimulate a right side of the brain (e.g., mouse brain) while a field-of-view 204 comprising the objects of interest shows a left side of the brain, or vice versa. In some instances, the stimulation light may either fully or partially overlap with the imaging light (e.g., at the sample). In some instances, the stimulation light may not overlap with the imaging light. For example, the stimulation light may stimulate a right side of the brain (e.g., mouse brain) while an imaging light is incident on a left side of the brain, or vice versa. In some instances, the imaging light and the stimulation light may share at least a part of the same optical path. In some instances, the optical paths of the stimulation light and the imaging light may be independent. In some instances, the optical paths of the stimulation light and the imaging light may be different. The stimulation light and the imaging light may be temporally modulated as previously described herein. For example, the stimulating light may stimulate a portion of the sample while a portion (e.g., a different portion) of the sample is being illuminated by the imaging light.

The stimulation light sources can be turned on in a pattern configured to deliver stimulation light to one or more objects of interest shown in an image generated by the microscope system. The pattern can be a predetermined pattern. In some cases, the pattern can be chosen by a user and provided as an input to a computer system configured to control the stimulation light source. The computer system may generate a pattern. The computer system or a user may analyze an image of the field-of-view and generate a pattern or modification to an existing pattern in response to the analysis. The pattern may change over time or in response to the imaged sample. Feedback may be provided via an image of a response to an earlier stimulation pattern, which may be used to formulate a subsequent stimulation pattern. The computer system will be described in detail herein. The pattern can be a constant pattern. Alternatively the pattern can change over time. The pattern can change with a predetermined frequency. The pattern can change when the field-of-view changes to a different sample or a different region of a current sample.

The stimulation light can be provided to at least a portion of the sample containing one or more objects of interest with a predetermined pattern. The pattern can comprise illuminating one or more of the light sources in the matrix or array in a temporal sequence. The pattern can comprise illuminating one or more of the light sources in the matrix or array with a specific frequency, intensity, power, time duration, and/or wavelength distribution (e.g., discrete wavelength or range of wavelengths).

The stimulation light source and/or illumination light source can be controlled by a computer system. The simulation light source and/or illumination light source can be in communication with the computer system through a wireless or wired connection. The computer system can comprise one or more processors configured to execute a program that generates patterned stimulation of the target object by the stimulation light source. The program can generate the patterned stimulation using an algorithm. The algorithm can take one or more optical properties of the system as inputs when building the stimulation pattern. The optical property inputs can comprise optical components in the microscope, focal length of one or more light sources through the optical components, and/or light transmission of the one or more optical components (e.g., transmission, reflectance, and/or absorbance as a function of wavelength, frequency, and/or intensity). The algorithm can use an image generated by detection of imaging light as an input to identify one or more locations of target object in the field-of-view for stimulation by the stimulation light. The algorithm can perform image analysis to detect one or more objects of interest for delivery of stimulation light. The algorithm can determine which stimulation light sources in an array and/or matrix of stimulation light sources should be illuminated in order to direct stimulation light to the one or more objects of interest detected in the image. The algorithm can determine the power density of stimulation light needed to stimulate the one or more objects of interest detected in the image.

Figure 10:
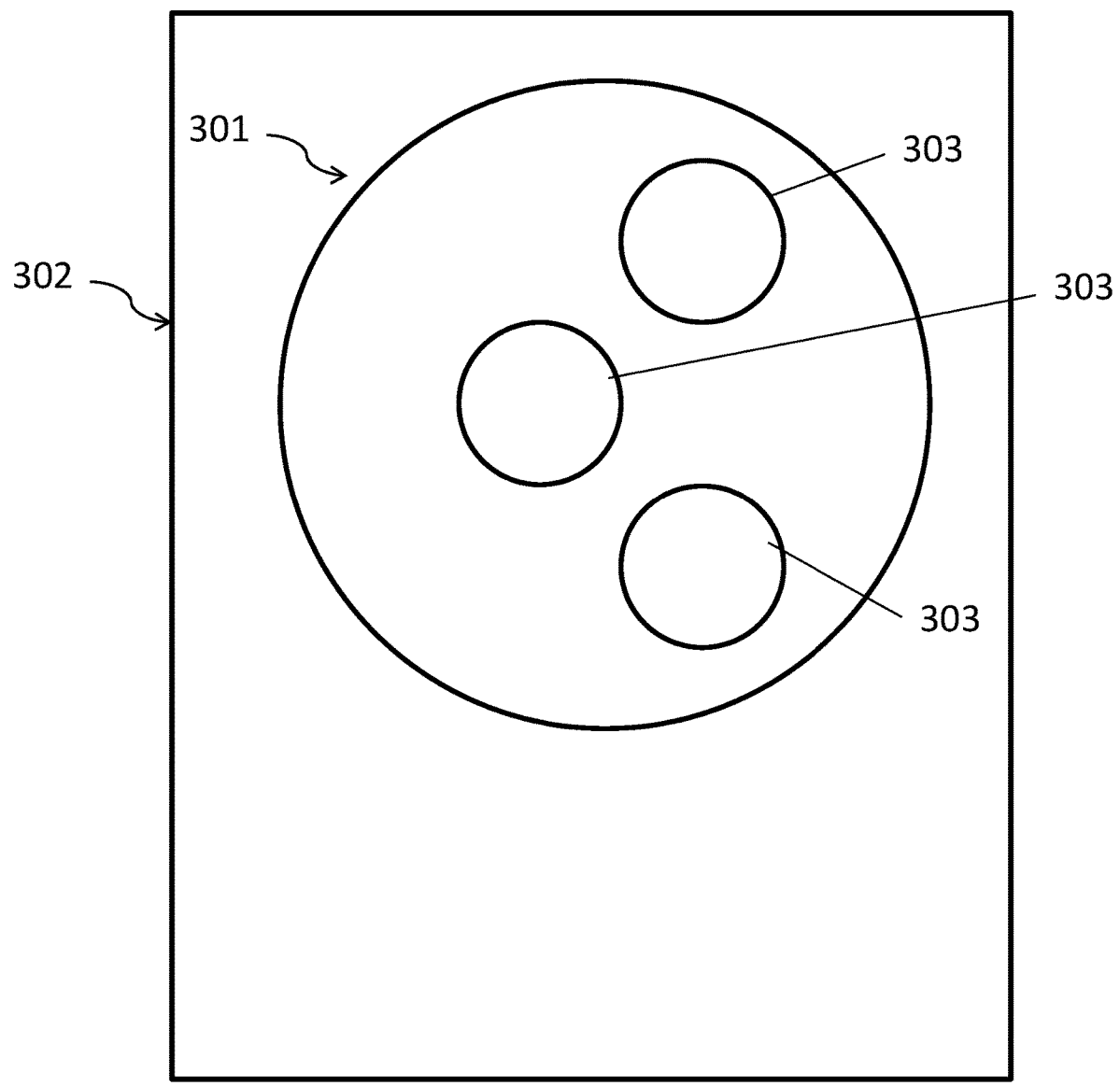
FIG. 10 shows a display that can be provided to a user to show a field-of-view imaged by the microscope system.

Alternatively or in addition to the algorithm a user can directly instruct the computer system to control the stimulation light source. A user can be an operator of the microscope system. The user can view an image of the field-of-view generated by the microscope system on a display device. FIG. 10 shows a schematic example of a field-of-view 301 that can be provided to the user on a display device 302. The field-of-view 301 can comprise one or more objects of interest 303. The user can select a specific stimulation pattern to be followed by the stimulation light source based on the location of the objects of interest shown on the display device 302. In some cases, a user can alter the stimulation light source pattern based on a response of the one or more objects of interest to the stimulation light. Alternatively or additionally, the one or more processors of the computer system can execute image analysis of the field-of-view to automatically detect the one or more objects of interest 303 and suggest or initiate a pattern to be followed by the stimulation light source to deliver stimulation light to the one or more objects of interest 303.

The user can specify a new stimulation pattern or the user can choose a previously used or generic stimulation pattern stored in a memory storage device on the computer system. A user can specify that the stimulation pattern change with time. The user can specify the frequency at which the stimulation pattern changes in time. A user can specify that the stimulation pattern change with each image captured by the microscope. The user can change the stimulation pattern while imaging the sample. In some cases, the user can change the stimulation pattern to target a specific object in or region of the sample based on one or more characteristics detected in an image of the sample in real time. For example a user can detect a population of neurons in the image of the sample and choose a stimulation light pattern to provide stimulation light to the population of neurons.

Figure 11:
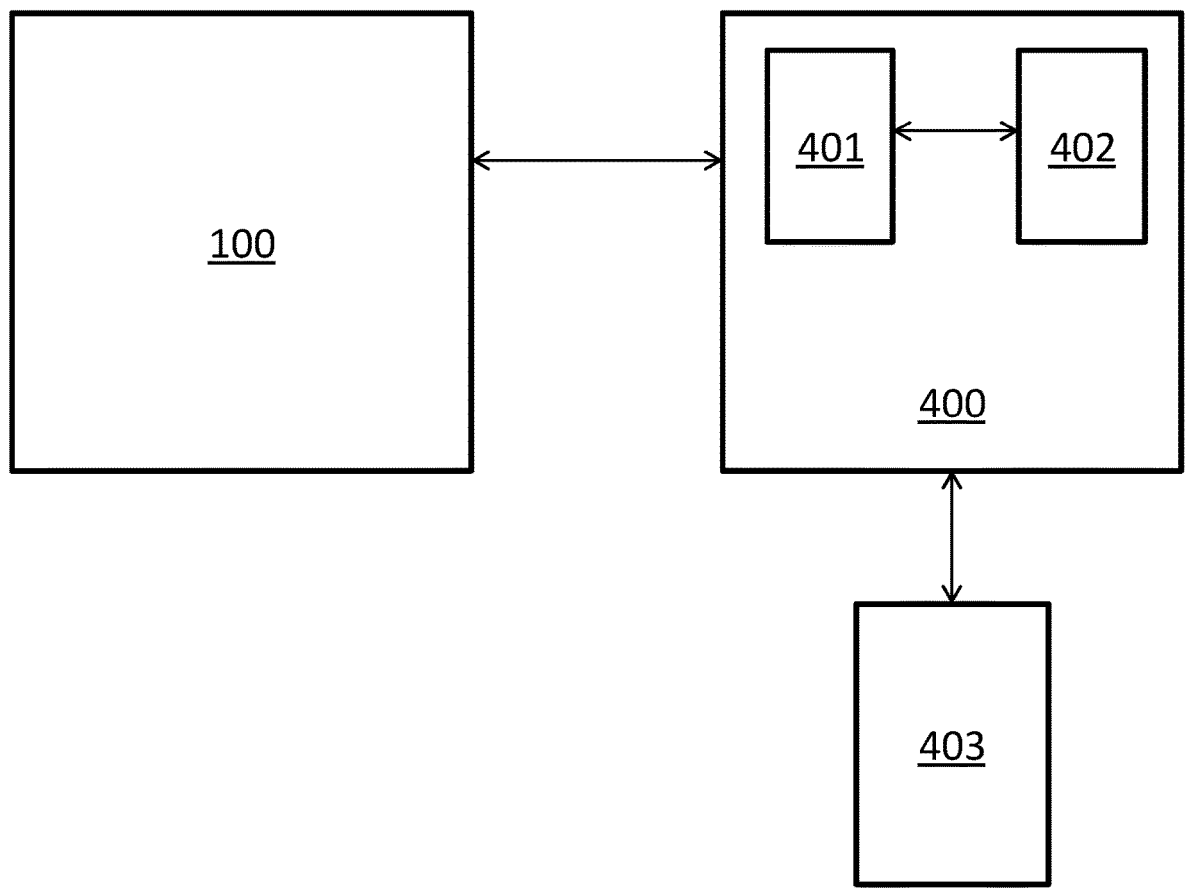
FIG. 11 shows a schematic of a small optogenetic microscope system in communication with a computer control system.

FIG. 11 shows a microscope system 100 in communication with a computer system 400. The microscope system 100 can be in communication with the computer system 400 through a wired or wireless connection. The computer system can comprise one or more processors 401. The one or more processors can be configured to execute one or more programs to control the microscope system. The processors can execute one or more programs to control the stimulation light source and/or the imaging light source of the microscope system. Instructions for the one or more programs can be stored on one or more memory storage devices 402. The one or more storage devices can be in communication with the one or more processors. At least a fraction of the memory storage devices can be part of a server in communication with the computer system.

A user can interact with the computer system through a user interface. The user interface can be provided in a display on a display device 403. The display device can be a monitor, screen, and/or electronic device in communication with the computer system 400. The display device 403 can be in communication with the computer system 400 though a wireless or wired connection. The user interface can be provided on a screen of a display device. The screen can be a liquid crystal display (LCD) screen or a touch screen. The display device can comprise a computer monitor. The display device can comprise and electronic device. The display device can be a hand held electronic device for example, a smartphone or tablet.

The microscope system can be configured to perform real-time simultaneous imaging and stimulation of target objects. The target object can be a living organism. The target objects can be conscious while the microscope system is operated. The microscope may be mounted onto a living organism or a non-living organism. In some instances, the microscope may be mounted to an exterior of an organism (e.g., over skin of the organism). The microscope may be used to image a sample on or within the organism. For example, the microscope may be mounted to a head of a subject and used to image brain tissue of the organism. The microscope may be mounted to a subject and used to image any other tissue on or within the subject.

The optogenetic microscope configured to simultaneously provide imaging and stimulation light described in detail herein can be used for various applications. For example the optogenetic microscope can be used to map regions of the brain of an organism. Connections between different nerve cells can be identified with the optogenetic microscope. The organism can be a living organism. In another example, the optogenetic microscope can be used to perform atrial fibrillation. The optogenetic microscope can be used to stimulate cardiac tissue in a living organism.

In another example, the optogenetic microscope can be used to stimulate light sensitive proteins. The light sensitive proteins can open or close ion channels or actively pump ions when stimulated by light from the optogenetic microscope.

Compact Optogenetic Microscope Systems Comprising an Adjustable Lens

Figure 14:
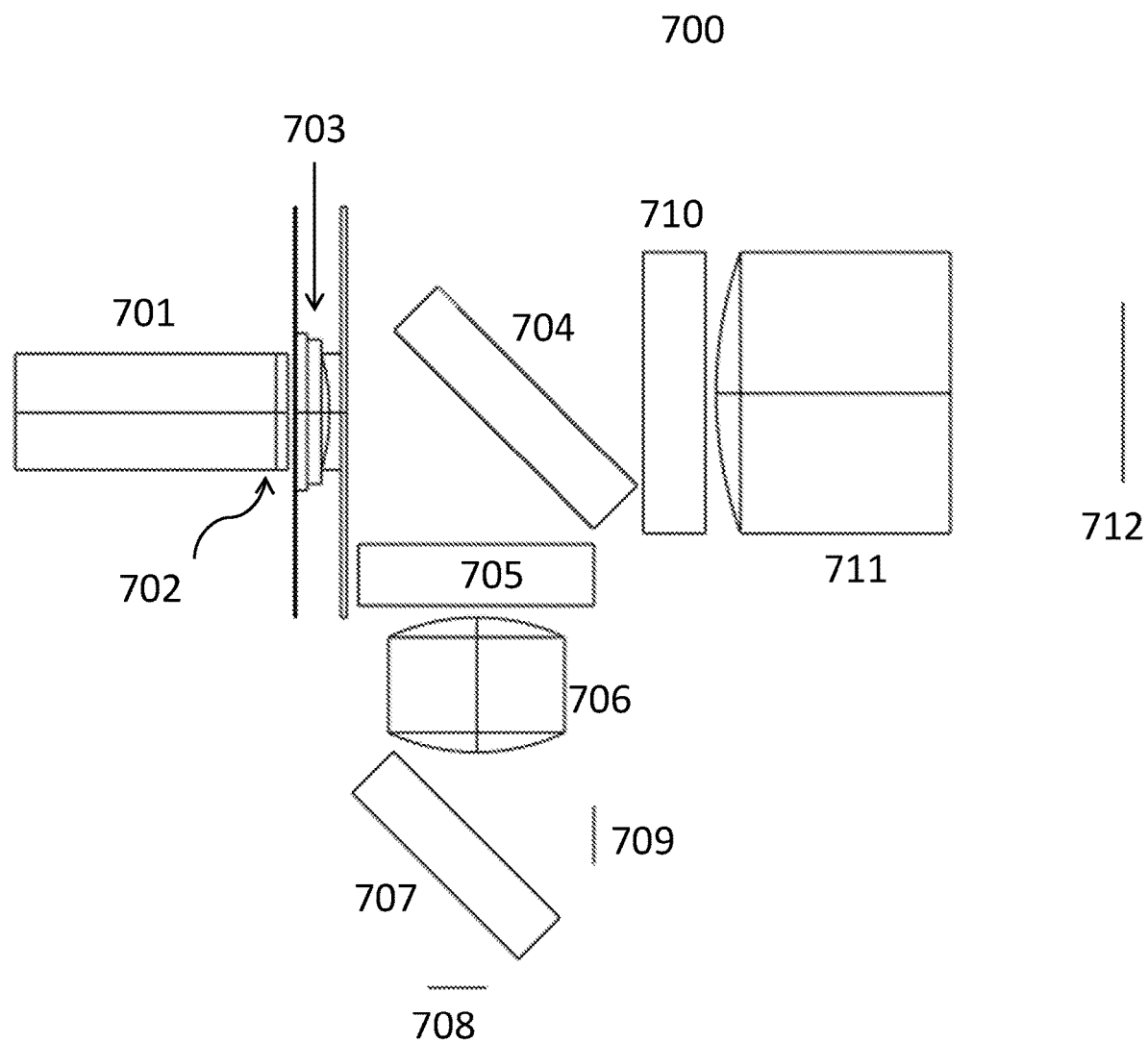
FIG. 14 shows a schematic of one embodiment of a compact optogenetic microscope system.
Figure 15A:
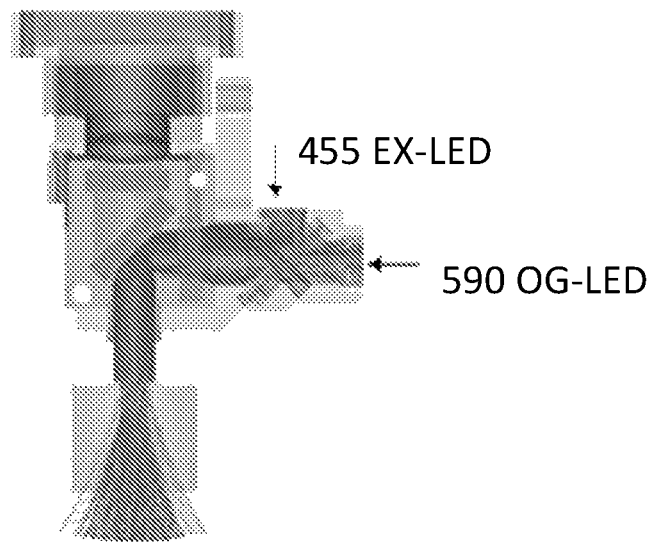
FIGS. 15A-B illustrates two non-limiting examples of configurations for a compact optogenetics microscope.
Figure 15B:
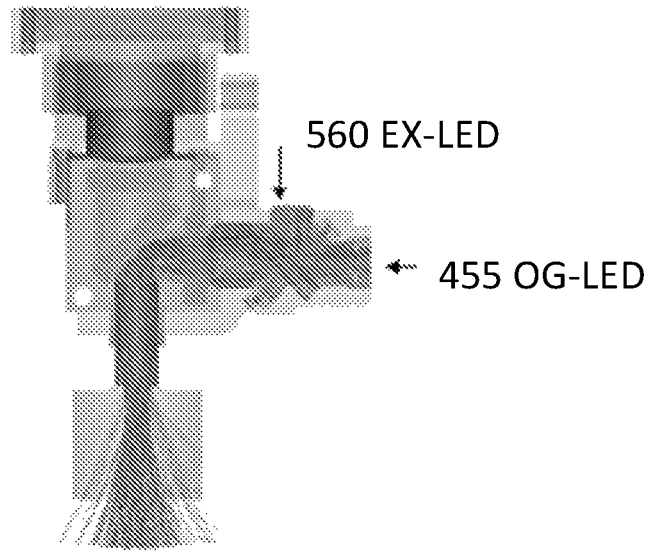

FIG. 14 illustrates one embodiment of a compact optogenetic microscope system 700 that comprises an adjustable lens 703 for adjusting the effective focal length and depth of field of the microscope system, or for correcting for chromatic aberration. Imaging light and stimulation light may be provided by light sources 708 and 709, and directed to the sample or subject by means of the optical path comprising dichroic mirror 707, lens 706, optical (excitation) filter 705, dichroic mirror 704, adjustable lens 703, optional corrective optical element 702, and/or gradient index (GRIN) lens 701. Imaging light reflected or scattered by the sample or subject is collected by GRIN lens 701, and transmitted to image sensor 712 by means of the optical path comprising optional corrective optical element 702, adjustable lens 703, dichroic reflector 704, optical (emission) filter 710, and lens 711. Similarly, fluorescence that is excited in the sample or subject by the stimulation light is collected by GRIN lens 701, and transmitted to image sensor 712 by means of the common optical path comprising optional corrective optical element 702, adjustable lens 703, dichroic reflector 704, optical (emission) filter 710, and lens 711. In combination with the transmittance properties of optical filters 705 and 710, the transmittance and reflectance properties of dichroic mirrors 707 and 704 determine the optical bandwidths of the imaging and stimulation light, as well as that for reflected or scattered imaging light and fluorescence light that reach the image sensor 712.

In some embodiments, GRIN lens 701 and optional corrective optical element 702 comprise the "objective" lens of the microscope system and are operably coupled to other lens elements. In some embodiments, GRIN lens 701 and optional corrective optical element 702 are components of an endoscopic probe attached to or optically coupled to other elements of the microscope system, wherein the endoscopic probe is designed to make contact with or be inserted into (e.g., partially implanted in) the sample or subject. Optionally, the corrective optical element 702 may be integrated with the GRIN lens 701. In some embodiments, the endoscopic probe may further comprise a cannula, e.g., a glass cannula, which is implanted in the sample or subject and into which the endoscopic probe is inserted. In some embodiments, the endoscopic probe may be a shared optical component of the illumination optical path, the stimulation optical path, and the imaging optical path, or any combination thereof. In some embodiments, more than one endoscopic probe may be utilized, wherein a different endoscopic probe is utilized by the illumination optical path, the stimulation optical path, the imaging optical path, or any combination thereof. In some embodiments, corrective optical element 702 compensates for the optical properties of GRIN lens 701 or an endoscopic probe comprising GRIN lens 701 to provide a toroidal object field having improved spatial resolution across the microscope's field-of-view. In those embodiments in which optional corrective optical element 702 is used, it is preferentially placed in contact with, or in close proximity to, the end of GRIN lens 701 that is distal from the sample or subject, although other placements are possible. In some embodiments, the compact optogenetic microscope system may comprise additional apertures, lenses, optical filters, dichroic mirrors, prisms, mirrors, beam splitters, polarizers, etc., to further refine the optical properties (e.g., wavelength, polarization, or intensity) or physical dimensions of the imaging and stimulation light beams delivered to the sample or subject. Similarly, the compact optogenetic microscope system may comprise additional apertures, lenses, optical filters, dichroic mirrors, prisms, mirrors, beam splitters, polarizers, etc., to further refine the optical properties or physical dimensions of the imaging and fluorescence light beams delivered to the image sensor.

Each of the components depicted in FIG. 14 may be contained within a single housing as substantially described elsewhere, e.g., with respect to FIG. 3. In some embodiments, the components depicted in FIG. 7 may be configured in such a way that they are contained in two or more separate housings. Alternatively, some of the components depicted in FIG. 14 may be contained within a single housing, or two or more housing, while other elements are located outside of the single housing, or two or more housings. For example, GRIN lens 701 and optional corrective optical element 702 may be located outside a single housing while the other components are located within the single housing. GRIN lens 701 and/or optional optical corrective element 702 may or may not be in direct contact with other optical elements such as adjustable lens 703. As illustrated in FIG. 14, in some embodiments, GRIN lens 701 and/or optional corrective optical element 702 are placed in direct contact with, or in close proximity to, adjustable lens 703, e.g. in close proximity to the end of the GRIN lens 701 (or optional corrective optical element 702) that is farthest from the sample or subject (or tissue thereof). In some embodiments, the optical components comprising the imaging light delivery optical path and the stimulation light delivery optical path may be separated from those comprising the reflected or scattered imaging and fluorescence light collection optical path, and may be packaged in separate housings (e.g., as optical illumination, stimulation, and imaging probes). In some embodiments, the optical components comprising the imaging light delivery optical path and those comprising the light collection optical path may be packaged separately from the stimulation light delivery path (e.g., as an alternative form of an optical imaging probe). In some embodiments, the optogenetic microscope and optical probe housings may be configured to be removably attached to a common baseplate for mounting on a subject, such that two or more complete microscopes, optical illumination probes, optical stimulation probes, or optical imaging probes, or any combination thereof, may be removably attached to the common baseplate at fixed or adjustable relative positions, and wherein the optical axes for the two or more microscopes, optical illumination probes, optical stimulation probes, or optical imaging probes are substantially parallel to each other. In some embodiments, the common baseplate may be configured such that the optical axes for the two or more microscopes, optical illumination probes, optical stimulation probes, or optical imaging probes are not substantially parallel to each other. In some embodiments, at least 1, 2, 3, 4, 5, 6, 7, 8, or more microscopes or optical probes may be attached to the common baseplate. In some embodiments, the configuration of the common baseplate determines the lateral distance between one or more microscopes, optical imaging probes, and optical stimulation probes. In many embodiments, the baseplate is designed to be mounted on the subject in a fixed position, and therefore provide reproducible alignment to the attached optical assemblies (e.g. microscopes, optical illumination probes, optical stimulation probes, or optical imaging probes) relative to tissue of the subject. In embodiments where separate optical stimulation probes and optical imaging probes are attached to a common baseplate, the area of the sample or subject that is illuminated by the optical stimulation probe may overlap partially, completely, or not at all with the area of the sample or subject (e.g., the field-of-view (FOV)) from which reflected or scattered imaging light and fluorescence are collected and imaged onto the image sensor of the optical imaging probe or microscope.

As disclosed throughout this application, the imaging light source (FIG. 14, 708 or 709) may comprise one or more LEDs, or other types of light emitting elements. The imaging light source may provide essentially monochromatic light. Alternatively the imaging light source may provide imaging light at multiple wavelengths. In one non-limiting example, the imaging light source may comprise two or more LEDs or other light emitting elements that emit light of different colors (e.g., different wavelength ranges). The imaging light source may provide light for single-color or multi-color imaging. In some embodiments, the imaging light source may comprise two or more light-emitting elements, e.g., LEDs, that are configured to emit light in user-defined spatial patterns and/or in user-defined temporal patterns. In these embodiments, the user-defined spatial pattern may have a spatial resolution at the focal plane of at least may be at least 0.1 at least 0.5 at least 1 at least 5 or at least 10 at least 15 at least 20 In some embodiments, the compact optogenetic microscope system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, e.g., wherein the tissue is brain tissue, the software-encoded instructions may comprise instructions for modulating the stimulation light in a time-dependent or spatially-dependent manner to induce a neurological response in said brain tissue, e.g., a therapeutic effect.

In many embodiments, the imaging light source is integrated with the optical elements configured to deliver imaging and/or stimulation light to the sample and is packaged within the same housing. In some embodiments, the imaging light source may be located externally to the housing that encloses the optical elements that deliver imaging and/or stimulation light to the sample, and optically coupled to the latter by means of, e.g., an optical fiber, a liquid light guide, or any other suitable means of guiding light. The imaging light source is configured to deliver imaging light to a sample or subject, or to tissue within a specified field-of-view within the subject, by means of the optical elements comprising a light delivery optical path.

As disclosed throughout this application, the stimulation light source (FIG. 14, 709 or 708) may also comprise one or more LEDs, or other types of light emitting elements. The stimulation light source may provide essentially monochromatic light. Alternatively the stimulation light source may provide stimulation light at multiple wavelengths. In one non-limiting example, the stimulation light source may comprise two or more high-intensity LEDs or other light emitting elements that emit light of different colors (e.g., different wavelength ranges). The stimulation light source may provide light for single-color or multi-color stimulation (excitation). In some embodiments, the stimulation light source may comprise two or more light-emitting elements, e.g., high intensity LEDs, that are configured to emit light in user-defined spatial patterns and/or in user-defined temporal patterns. In many embodiments, the stimulation light source is integrated with the optical elements configured to deliver imaging and/or stimulation light to the sample and is packaged within the same housing. In some embodiments, the stimulation light source may be located externally to the housing that encloses the optical elements that deliver imaging and/or stimulation light to the sample, and optically coupled to the latter by means of, e.g., an optical fiber, a liquid light guide, or any other suitable means of guiding light. The stimulation light source is configured to deliver stimulation light to a sample or subject, or to tissue within a specified illumination area or field-of-view within the subject, by means of the optical elements comprising a light delivery optical path.

As disclosed throughout this application, the image sensor 712 may comprise a monochromatic image sensor or a color image sensor. In some embodiments, the compact optogenetic microscope system may comprise two or more image sensors. Examples of suitable image sensors include, but are not limited to, CCD sensor chips and CMOS image sensors. In some embodiments, the image sensor captures a single image or a series of images, which may be greyscale or RGB images. The single image or series of images may be captured before, during, or after delivery of stimulation light to the sample or subject using predefined or user-adjustable exposure times. In some embodiments, the timing of image capture by the image sensor may be synchronized with the timing for spatial and/or temporal modulation of the delivery of stimulation light to the subject or sample. In some embodiments, the timing of image capture by the image sensor maybe offset (out of phase) with the timing for spatial and/or temporal modulation of the delivery of stimulation light to the sample or subject. Light that is reflected, scattered, or emitted (e.g., upon excitation by stimulation light) by the sample or subject, or by tissue within a subject, is collected and delivered to the image sensor by means of the optical elements comprising a light collection optical path.

The adjustable lens 703 in FIG. 14 may comprise a deformable lens. Alternatively or in addition, the adjustable lens may comprise movable components, e.g. movable optical elements. The adjustable lens may be adjusted by electro-optical means, mechanical means, electromechanical means, thermo-optical means, and/or acousto-mechanical means. For example, by applying voltage to the lens and/or components associated with the adjustable lens, a focal length of the lens may be adjusted. For example, by applying voltage to the lens and/or components associated with the adjustable lens, the lens may be tilted. An adjustable lens adjustable by any electrically-related means may herein also be referred to as an electronic lens or "e-lens". In many embodiments, at least one adjustable or deformable lens may constitute an optical element that is shared by the optical paths by which imaging light and stimulation light are transmitted to the sample. In these embodiments, the at least one shared adjustable or deformable lens may be positioned in close proximity to the end of the GRIN lens (or optional corrective optical element) that is farthest from the sample or tissue. In some embodiments, the compact optogenetic microscope system may comprise two or more adjustable lenses configured, for example, to separately adjust the effective focal length of the stimulation and image collection light paths, thereby ensuring that stimulation light is focused on the same focal plane that is used as the field-of-view by the image collection optics. In some embodiments, the effective focal length of the stimulation and image collection light paths may be adjusted to ensure that stimulation light is focused on a different focal plane than that used as the field-of-view by the image collection optics. In some embodiments, the effective focal length is adjustable such that the focal plane for the stimulation light and/or that for the image collection optics is adjustable over a range of about 50 µm, about 100 µm, about 200 µm, about 300 µm, about 400 µm, or about 500 µm, without loss of spatial resolution.

In some instances, the adjustable lens may comprise a piezoelectric component or a mechanical component. For example, a lens fluid may be pumped into or out of a lens enclosure which expands or retracts the lens membrane to achieve varying focus and/or zoom. For example, an actuator may push or release a deformable wall to change a volume of liquid in a chamber to adjust a curvature of a lens, e.g. liquid lens. In some instances, voltage applied to a piezoelectric component may deform a thin membrane, e.g. a thin glass membrane that is in contact with a liquid or polymer layer coated on a substrate, thereby deforming the liquid or polymer layer and changing its optical properties. As non-limiting examples, the adjustable lens may comprise a liquid lens, a liquid-crystal lens, and/or a piezoelectric tunable lens, or any combination thereof.

The adjustable lens may comprise a size amenable for integration with the small microscope system described throughout. In some instances, the adjustable lens may comprise a radius equal to or less than about 1 mm, 2 mm, 3 mm, 4 mm, 5 mm, 6 mm, 7 mm, 8 mm, 9 mm, 10 mm, 12 mm, 14 mm, 16 mm, 18 mm, or 20 mm. Optionally, the adjustable lens may comprise variable radii. In some instances, the adjustable lens may comprise a thickness or height equal to or less than about 1 mm, 2 mm, 3 mm, 4 mm, 5 mm, 6 mm, 7 mm, 8 mm, 9 mm, 10 mm, 12 mm, 14 mm, 16 mm, 18 mm, or 20 mm. Optionally, the adjustable lens may comprise variable height.

The adjustable lens may comprise adjustable optical parameters. For example, the adjustable lens may comprise a variable focal length. As another example, the adjustable lens may comprise a variable optical axis. In some instances, the adjustable lens may be tilted and/or dithered. The adjustable lens may or may not be tilted about its optical axis. In some instances, an optical axis of the adjustable lens may be tilted or adjusted. The adjustable lens may be utilized, for example, for bringing images into focus, changing the effective focal depth to enable volumetric imaging, and/or for correcting chromatic aberrations.

In some embodiment, the adjustable lens may comprise a focal length equal to or more than about 10 mm, 15 mm, 20 mm, 25 mm, 30 mm, 40 mm, 50 mm, 60 mm, 70 mm, 80 mm, 90 mm, or 100 mm, or any focal length within this range. In some embodiments, the adjustable lens may be adjusted to have any of the previously referred to focal lengths at any given point in time.

In some embodiments, the adjustable lens may comprise a negative focal length or a focal length of infinity. In some embodiments, the adjustable lens may provide for a refractive power of about −100 to about +100 diopters, where diopter is defined as the reciprocal of the focal length in units of meters. In some embodiments, the adjustable lens may provide for refractive power of at least −100 diopters, at least −90 diopters, at least −80 diopters, at least −70 diopters, at least −60 diopters, at least −50 diopters, at least −40 diopters, at least −30 diopters, at least −20 diopters, at least −10 diopters, at least 0 diopters, at least +10 diopters, at least +20 diopters, at least +30 diopters, at least +40 diopters, at least +50 diopters, at least +60 diopters, at least +70 diopters, at least +80 diopters, at least +90 diopters, or at least +100 diopters. In some embodiments, the adjustable lens may provide for a refractive power of at most +100 diopters, at most +90 diopters, at most +80 diopters, at most +70 diopters, at most +60 diopters, at most +50 diopters, at most +40 diopters, at most +30 diopters, at most +20 diopters, at most +10 diopters, at most +0 diopters, at most −10 diopters, at most −20 diopters, at most −30 diopters, at most −40 diopters, at most −50 diopters, at most −60 diopters, at most −70 diopters, at most −80 diopters, at most −90 diopters, or at most −100 diopters. Any of the lower and upper values described in this paragraph may be combined to form a range included within the disclosure, such as the adjustable lens may provide a refractive power that ranges from about +20 diopters to about +70 diopters. Those of skill in the art will recognize that the adjustable lens may provide a refractive power having any value within this range, e.g., about +25 diopters.

Tilting an adjustable lens as referred herein may refer to tilting the adjustable lens itself. Alternatively or in addition, tilting the adjustable lens may refer to adjusting the adjustable lens (e.g. deforming the lens, adjusting a curvature of the liquid lens) such that an optical axis of the adjustable lens is tilted or varied. The tilt angle may or may not be about the optical axis of the adjustable lens. Optionally, the adjustable lens may be configured to be tilted at a tilt angle equal to or more than about 0.1°, 0.2°, 0.3°, 0.4°, 0.6°, 0.8°, 1°, 1.2°, 1.5°, 2°, 2.5°, 3°, 4°, or 5°.

In some embodiments, the disclosed optogenetic microscopes, or component optical probes, may comprise at least 1 adjustable or deformable lens, at least 2 adjustable or deformable lenses, at least 3 adjustable or deformable lenses, at least 4 adjustable or deformable lenses, or more. In those embodiments utilizing one or more adjustable or deformable lenses, the effective focal depth of the compact optogenetic microscope system or optical imaging probes may be varied to enable volumetric imaging, as referenced above. In such embodiments, the optogenetic microscope or optical imaging probes may be capable of collecting light and generating images over a sample or tissue volume of about 1 mm×1 mm×50 µm deep, or about 1 mm×1 mm×100 µm deep, or about 1 mm×1 mm×200 µm deep, or about 1 mm×1 mm×300 µm deep, or about 1 mm×1 mm×400 µm deep, or about 1 mm×1 mm×300 µm deep.

In some embodiments, the illumination area, stimulation area, and/or field-of-view (FOV) for the microscope system or optical probes may range from about 100 µm×100 µm to about 5 mm×5 mm. In some embodiments, the FOV is at least 100 µm×100 µm, at least 200 µm×200 µm, at least 300 µm×300 µm, at least 400 µm×400 µm, at least 500 µm×500 µm, at least 600 µm×600 µm, at least 700 µm×700 µm, at least 800 µm×800 µm, at least 900 µm×900 µm, at least 1 mm×1 mm, at least 1.1 mm×1.1 mm, at least 1.2 mm×1.2 mm, at least 1.3 mm×1.3 mm, at least 1.4 mm×1.4 mm, at least 1.5 mm×1.5 mm, at least 1.6 mm×1.6 mm, at least 1.7 mm×1.7 mm, at least 1.8 mm×1.8 mm, at least 1.9 mm×1.9 mm, at least 2 mm×2 mm, at least 2.5 mm×2.5 mm, at least 3 mm×3 mm, at least 3.5 mm×3.5 mm, at least 4 mm×4 mm, at least 4.5 mm×4.5 mm, or at least 5 mm×5 mm. In some embodiments, the FOV is at most 5 mm×5 mm, at most 4.5 mm×4.5 mm, at most 4 mm×4 mm, at most 3.5 mm×3.5 mm, at most 3 mm×3 mm, at most 2.5 mm×2.5 mm, at most 2 mm×2 mm, at most 1.9 mm×1.9 mm, at most 1.8 mm×1.8 mm, at most 1.7 mm×1.7 mm, at most 1.6 mm×1.6 mm, at most 1.5 mm×1.5 mm, at most 1.4 mm×1.4 mm, at most 1.3 mm×1.3 mm, at most 1.2 mm×1.2 mm, at most 1.1 mm×1.1 mm, at most 1 mm×1 mm, at most 900 µm×900 µm, at most 800 µm×800 µm, at most 700 µm×700 µm, at most 600 µm×600 µm, at most 500 µm×500 µm, at most 400 µm×400 µm, at most 300 µm×300 µm, at most 200 µm×200 µm, or at most 100 µm×100 µm. Any of the lower and upper values described in this paragraph may be combined to form a range included within the disclosure, such as the illumination/stimulation area and FOV may range from about 800 µm×800 µm to about 1.2 mm×1.2 mm. Those of skill in the art will recognize that the illumination/stimulation and FOV may have any value within this range, e.g., about 1.15 mm×1.15 mm.

In some embodiments, the effective focal depth of the microscope system may range from about 10 µm to about 1 mm. In some embodiments, the effective focal depth may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, or at least 1 mm. In some embodiment, the effective focal depth may be at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the disclosure, such as the effective focal depth may range from about 200 µm to about 500 µm. Those of skill in the art will recognize that the effective focal depth may have any value within this range, e.g., about 275 µm. In some embodiments, the effective focal depth of the microscope system is varied as a series of one or more images are captured at each effective focal depth setting.

In some embodiments, the spatial resolution of the images provided by the compact optogenetic microscope system may range from about 0.1 µm to about 5 µm at the center of the field-of-view. In some embodiments, the spatial resolution may be at least 0.1 µm, at least 0.25 µm, at least 0.5 µm, at least 0.75 µm, at least 1 µm, at least 1.5 µm, at least 2 µm, at least 3 µm, at least 4 µm, or at least 5 µm at the center of the field-of-view. In some embodiments, the spatial resolution may be at most 5 µm, at most 4 µm, at most 3 µm, at most 2 µm, at most 1.5 µm, at most 1 µm, at most 0.75 µm, at most 0.5 µm, at most 0.25 µm, or at most 0.1 µm at the center of the field-of-view. Any of the lower and upper values described in this paragraph may be combined to form a range included within the disclosure, such as the spatial resolution may range from about 0.75 µm to about 2 µm at the center of the field-of-view. Those of skill in the art will recognize that spatial resolution may have any value within this range, e.g., about 1.6 µm, at the center of the field-of-view.

In some embodiments, the spatial resolution of the images provided by the compact optogenetic microscope system may vary across the field-of-view, and may range from about 0.1 µm to about 30 µm. In some embodiments, the minimum spatial resolution across the field-of-view may be at least 0.1 µm, at least 0.5 µm, at least 1 µm, at least 5 µm, at least 10 µm, at least 15 µm, at least 20 µm, at least 25 µm, or at least 30 µm. In some embodiments, the minimum spatial resolution may be at most 30 µm, at most 25 µm, at most 20 µm, at most 15 µm, at most 10 µm, at most 5 µm, at most 1 µm, at most 0.5 µm, or at most 0.1 µm. Any of the lower and upper values described in this paragraph may be combined to form a range included within the disclosure, such as the minimum spatial resolution may range from about 1 µm to about 20 µm. Those of skill in the art will recognize that minimum spatial resolution may have any value within this range, e.g., about 20 µm.

In some embodiments, one or more corrective optical elements (702 in FIG. 14) may be used to improve the spatial resolution of the images provided by the compact optogenetic microscope system across the entire field-of-view. In these embodiments, the minimum spatial resolution across the entire field-of-view may range from about 0.1 µm to about 5 µm. In some embodiments, the minimum spatial resolution across the entire field-of-view may be at least 0.1 µm, at least 0.25 µm, at least 0.5 µm, at least 0.75 µm, at least 1 µm, at least 1.5 µm, at least 2 µm, at least 3 µm, at least 4 µm, or at least 5 µm. In some embodiments, the minimum spatial resolution across the entire field-of-view may be at most 5 µm, at most 4 µm, at most 3 µm, at most 2 µm, at most 1.5 µm, at most 1 µm, at most 0.75 µm, at most 0.5 µm, at most 0.25 µm, or at most 0.1 µm. Any of the lower and upper values described in this paragraph may be combined to form a range included within the disclosure, such as the minimum spatial resolution across the entire field-of-view may range from about 0.75 µm to about 2 µm. Those of skill in the art will recognize that minimum spatial resolution may have any value within this range, e.g., about 1.6 µm.

In some embodiments, one or more adjustable lenses may be used to actively correct for chromatic aberrations. In some instances, the adjustable lens may be utilized to axially correct chromatic aberrations. For example, the chromatic aberration may be corrected or mitigated by changing a focal length of the adjustable lens as appropriate. For example, multi-color stimulation or imaging systems may experience chromatic aberration as different colors (e.g. different wavelengths) of light may be focused differently by an optical element such as a lens. Accordingly, for different wavelengths of light (or different wavelength ranges), it may be necessary to adjust a focal length of the adjustable lens in order to bring an image into focus or to focus stimulation light on the same sample plane as that used to image the sample or subject. In some embodiments, adjustments to the effective focal distance using an adjustable lens may be synchronized with capture of images by the image sensor.

Alternatively or in addition, the adjustable lens may be utilized in some embodiments to correct chromatic aberration in a lateral plane. For example, chromatic aberration in the lateral plane may be corrected or mitigated by tilting the adjustable lens to an appropriate tilt angle. In some instances, the adjustable lens may be tilted in a radial (i.e., where the lens is tilted from an angle of 0 degrees (aligned with the optical axis) in one direction to a specified angle (e.g., along the x-axis)) or circular pattern (i.e., where the lens is tilted to a fixed angle and then rotated around the optical axis a full 360 degrees) while a plurality of images is captured by the image sensor (e.g. using an image capture circuit that synchronizes the image capture process with tilting of the adjustable lens). Subsequently, the plurality of images captured in conjunction with the tilting and/or rotation of the lens may be processed to provide images that have been corrected for chromatic aberration. The plurality of captured images may comprise images captured at differing tilt angles. The differing tilt angles may refer to tilt angles that differ in magnitude, or that differ in a tilt direction about the optical axis. In some instances, the plurality of images may be captured at tilt angles having the same or similar magnitudes. Alternatively, the plurality of images may be captured at tilt angles having differing magnitudes. In some embodiments, dithering the tilt angle and direction of the adjustable lens (i.e., inducing random variations in tilt angle and direction) may be used to correct for chromatic aberration within a single image if the dithering is done at a sufficiently high frequency to provide coverage of the full field-of-view within the exposure time required to capture an image. In some embodiments, the tilt angle of the adjustable lens is dithered while a plurality of images is captured in a synchronized fashion.

In some embodiments, one or more processors may also be provided (e.g., integrated within the microscope housing, or as part of an external controller that communicates with the compact microscope system) to aid in correcting images for chromatic aberration. For example, the one or more processors may individually or collectively utilize a plurality of captured images to correct for or minimize chromatic aberration. The plurality of images may be the images captured with the adjustable lens tilted (e.g., in a circular or radial pattern) as described above. In some instances, the plurality of captured images may be combined, e.g., in post processing of the images, to produce a processed image. Combining or processing the plurality of images captured with differing tilt angles of the adjustable lens may reduce or eliminate chromatic aberration, e.g. in the lateral plane. The differing tilt angles may refer to tilt angles that differ in magnitude or in direction about the optical axis. In some instances, the plurality of captured images used to correct for chromatic aberration may be equal to or more than about 5 images, 10 images, 15 images, 20 images, 25 images, 30 images, 40 images, 50 images, 60 images, 80 images, 100 images, 150 images, 200 images, 250 images, 300 images, 400 images, or 500 images.

As mentioned, in some embodiments the capture of images by the image sensor may be synchronized with the tilting or dithering of the adjustable lens. For example, the adjustable lens may be tilted or dithered according to an image capture rate of the image sensor. Alternatively, the adjustable lens may be tilted or dithered at a rate greater than an image capture rate of the image sensor. Alternatively, the adjustable lens may dither or tilt at a rate lesser than an image capture rate of the sensor. The image capture circuit may capture images at a rate equal to about or more than 10 fps, 15 fps, 20 fps, 25 fps, 30 fps, 40 fps, 50 fps, 60 fps, 80 fps, 100 fps, 120 fps, 140 fps, 160 fps, 180 fps, 200 fps, 220 fps, 240 fps, 280 fps, 320 fps, 360 fps, 400 fps, or more. The adjustable lens may be adjusted (e.g., tilted, dither, etc.) at a rate equal to or more than about 10 adjustments per second, 15 adjustments per second, 20 adjustments per second, 25 adjustments per second, 30 adjustments per second, 40 adjustments per second, 50 adjustments per second, 60 adjustments per second, 80 adjustments per second, 100 adjustments per second, 120 adjustments per second, 140 adjustments per second, 160 adjustments per second, 180 adjustments per second, 200 adjustments per second, 220 adjustments per second, 240 adjustments per second, 280 adjustments per second, 320 adjustments per second, 360 adjustments per second, 400 adjustments per second, or more.

In some instances, an adjustable lens may be especially useful for multi-color stimulation or multi-color imaging applications. As previously described herein, multi-color imaging may experience chromatic aberration or may capture out of focus images as different colors (e.g., wavelengths) of light can have different focal lengths when focused through an optical element such as a lens. Accordingly, for different wavelengths (e.g., different ranges of wavelengths), utilizing differing focal lengths may be appropriate or necessary to bring an image into focus. In some instances, the adjustable lens may be adjusted such that the focal length is appropriate to bring an image into focus for the different wavelengths of light. Optionally, one or more processors may be provided to vary a focal length of the imaging system (e.g., using an adjustable lens) such that captured images are always in focus for differing wavelengths of light.

In some instances, different optical arrangements or light sources emitting differing ranges of wavelengths of lights may be temporally multiplexed. In conjunction with the temporal multiplexing of the optical arrangements or light sources, an adjustable lens may be adjusted such that stimulation light is focused on the same sample or subject plane as that comprising the field-of view to be imaged. Also, in conjunction with the temporal multiplexing of the optical arrangements or light sources, an adjustable lens may be adjusted such that the imaging system is able to capture in-focus images for differing wavelengths of reflected, scattered, or emitted light. In some instances, the adjustable lens' focal length may be adjusted substantially simultaneously with the temporal multiplexing of the optical arrangements or light sources in order to bring captured images into focus. Alternatively, the adjustable lens' focal length may be adjusted substantially sequentially with the temporal multiplexing of the optical arrangements or light sources in order to bring captured images into focus. In some instances, one or more processors may be provided to ensure that the focal length of the imaging system or adjustable lens is adjusted appropriately according to light (e.g., excitation light) produced by the optical arrangements or light sources to bring captured images into focus. Alternatively or in addition, the one or more processors may be provided to ensure that the focal length of the imaging system or adjustable lens is adjusted appropriately according to light (e.g., emission light) produced by the samples to bring captured images into focus. Additionally, the adjustable lens may be tilted and/or dithered to mitigate or correct for chromatic aberrations as referred to above.

As discussed above, the compact optogenetic microscope may be used to study both human subjects and animal subjects. In those embodiments comprising one or more adjustable lenses, the adjustable lenses may be used, for example, to bring the imaging light and stimulation light into the same or different focal planes and/or fields-of-view, or for example, to correct for chromatic aberration within the field-of-view. A non-limiting example of a method for using the compact optogenetic microscope to simultaneously stimulate and image tissue within a subject may comprise: a) providing an optical system according to any of the embodiments disclosed herein; b) providing a subject comprising the tissue to be stimulated and imaged; c) mounting or implanting the optical system of step (a) on or within the subject; and d) generating one or more images of the tissue before, during, or after directing stimulation light to the tissue of said subject in a time-modulated or spatially-modulated manner. The compact optogenetic microscopes disclosed herein may be used, for example, for modulating presynaptic inputs of neural tissue while imaging postsynaptic cells, imaging and modulating the same population of cells, or imaging and modulating different populations within the same field-of-view. In some embodiments, animal subjects may include rodents (e.g., mice, rats, rabbits, guinea pigs, gerbils, hamsters), simians, canines, felines, avines, insects, or any other type of animal. In some embodiments, the microscope may be mounted on, or inserted into, a living subject (or a non-living subject) and used for pre-clinical or clinical research. In some embodiments, the microscope may be used for clinical diagnostic or therapeutic applications. In some embodiments, the compact optogenetic microscope may be used in conjunction with light-activated ion channels to deliver a spatio-temporal pattern of optical stimulation that, when processed by the neural tissue of the brain, triggers a specific effect in the subject. Examples of specific effects that may be triggered in the subject by delivery of a spatio-temporal pattern of optical stimulation include, but are not limited to, changes in appetite/feeding behavior, invoking of fear/avoidance behavior, reward-seeking behavior, enhancement or suppression of motor activity in general, and alteration of sleep patterns.

Implantable Microscope Systems

In some embodiments of the compact optogenetic microscope system disclosed herein, the system may be configured as a partially or fully-implantable device (i.e., one in which the device does not break the skin barrier). In these embodiments, the microscope system, or components thereof (e.g., one or more individual optical illumination probes, optical stimulation probes, optical imaging probes, or any combination thereof) may be enclosed in a hermetically-sealed, biocompatible housing, e.g., a housing having an outer surface fabricated from a biocompatible material. Non-limiting examples of suitable materials for fabricating the biocompatible housing (or outer surface thereof) may include various metals (e.g., stainless steels, cobalt-based alloys, titanium, and titanium-based alloys), polymers (e.g., polypropylene, high-density polyethylene, polymethylmethacrylate, and silicone), ceramics (e.g., zirconium dioxide), composite materials, or combinations thereof.

In these implantable embodiments, the microscope system may further comprise a wireless transmitter/receiver (or wireless adapter, e.g., a radio frequency or optical wireless link) that communicates with an external controller and enables wireless data and power transmission between the external controller and the implanted device. In some embodiments, the wireless transmitter/receiver provides for both data read and data write communication (separately and/or simultaneously). Wireless data transmission rates in these embodiments may range from about 1 Mbit/s to about 7 Gbit/s. In some embodiments, the wireless data transmission rate may be at least about 1 Mbit/s, at least about 5 Mbit/s, at least about 10 Mbit/s, at least about 50 Mbit/s, at least about 100 Mbit/s, at least about 200 Mbit/s, at least about 300 Mbit/s, at least about 400 Mbit/s, at least about 500 Mbit/s, at least about 600 Mbit/s, at least about 700 Mbit/s, at least about 800 Mbit/s, at least about 900 Mbit/s, at least about 1 Gbit/s, at least about 2 Gbit/s, at least about 3 Gbit/s, at least about 4 Gbit/s, at least about 5 Gbit/s, at least about 6 Gbit/s, or at least about 7 Gbit/s.

The implantable microscope systems disclosed herein may comprise optical designs, optical performance characteristics, and physical features as described for other embodiments of the compact optogenetic microscope systems disclosed herein. Application of the implantable microscope systems include optical stimulation of genetically-modified tissue in a subject, wherein the tissue has been genetically modified to incorporate light-driven ion channels and/or fluorescent calcium indicators, or other fluorescent ion indicators, and wherein the implanted device is configured to deliver s spatially and/or temporally modulated sequence of stimulation light pulses to neurons within the illumination field and/or field-of-view of the device so as to stimulate a selected neuron or set of neurons that are processed by the subject to trigger a therapeutic response. In some embodiments, e.g., those in which the subject's tissue has been genetically-modified to include fluorescent calcium indicators or other fluorescent ion indicators, the implanted device may be configured to both deliver the spatially and/or temporally modulated sequence of stimulation light pulses, and to image the response induced in the targeted neurons (i.e., the neurons that are stimulated by the stimulation light pulses). In some embodiments, the imaged response in the targeted neurons, or in neurons adjacent to or in close proximity to the targeted neurons, is used via a feedback loop to modify the spatial and/or temporal pattern of stimulation light pulses. Examples of potential applications for the implanted devices of the present disclosure include optogenetic inducement of atrial fibrillation in test subjects, optogenetic stimulation of cardiac muscle tissue in cardiac patients, optogenetic stimulation of retinal neurons in vision-loss patients, and optogenetic stimulation of the vagus nerve in epilepsy patients. Other examples of potential applications include, but are not limited to, stimulation to induce alterations in sleep, appetite, drug-dependence, gambling, or other habitual behaviors, suppression of tremor in Parkinson's patients, and restoration of normal movement in other movement disorders.

Control Systems

Figure 12:
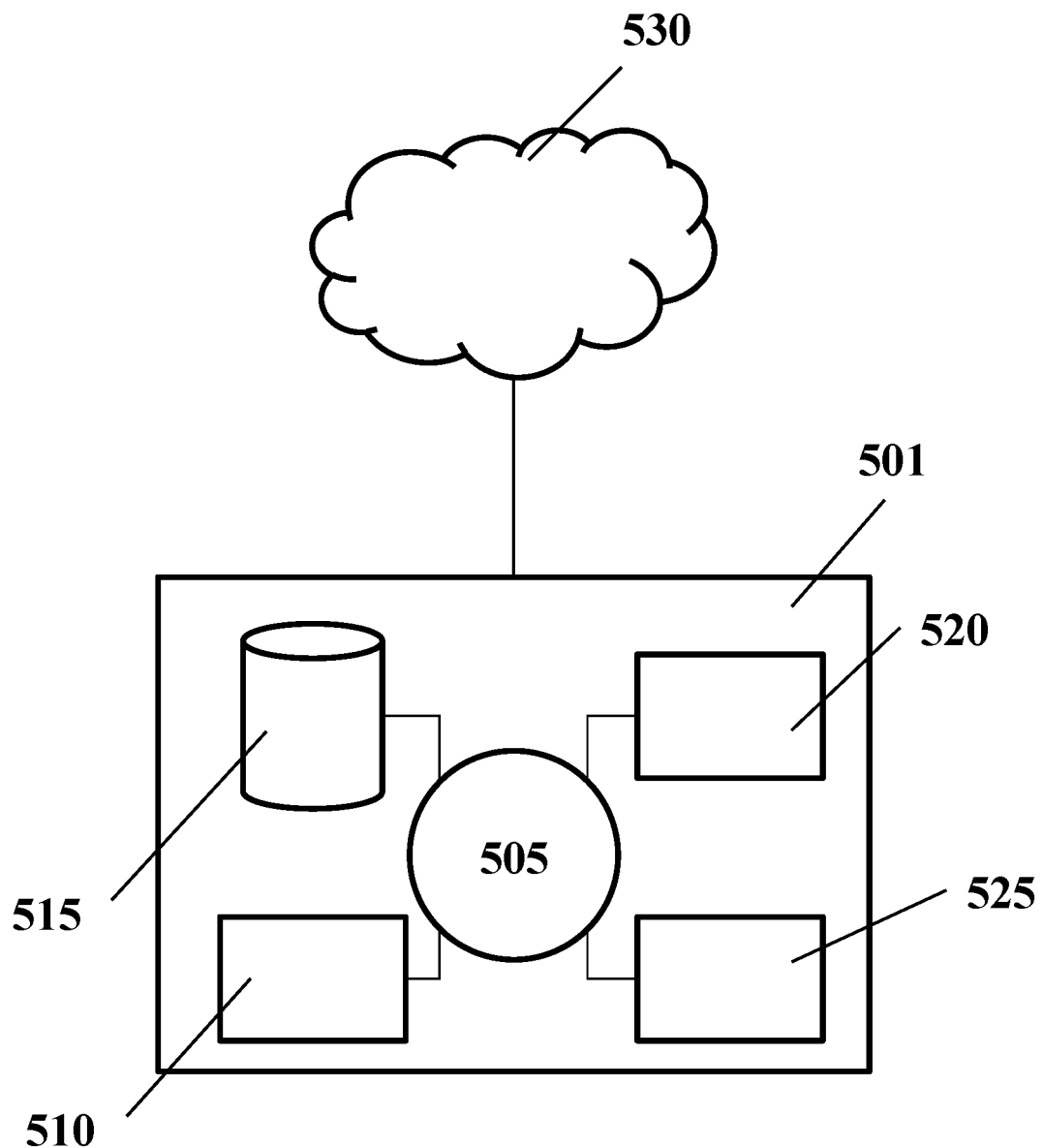
FIG. 12 shows a computer system configured to control the microscope system.

The present disclosure provides computer control systems that are programmed to implement methods of the disclosure. FIG. 12 shows a computer system 501 that is programmed or otherwise configured to control a stimulation light source incident on a sample. The computer system can be configured to identify regions of a sample that comprise one or more objects of interest for stimulation by the stimulation light source. The computer system can regulate various aspects of the stimulation light source, such as, for example, the intensity, location of incident light on the sample in the field-of-view of the microscope system, and/or the duration of the illumination of the sample by the stimulation light source.

The computer system includes a central processing unit (CPU, also "processor" and "computer processor" herein) 505, which can be a single core or multi core processor, or a plurality of processors for parallel processing. The computer system also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory, storage unit, interface and peripheral devices are in communication with the CPU 505 through a communication bus (solid lines), such as a motherboard. The storage unit can be a data storage unit (or data repository) for storing data. The computer system 501 can be operatively coupled to a computer network ("network") 530 with the aid of the communication interface 520. The network can be the Internet, an internet and/or extranet, or an intranet and/or extranet that is in communication with the Internet. The network in some cases is a telecommunication and/or data network. The network 530 can include one or more computer servers, which can enable distributed computing, such as cloud computing. The network 530, in some cases with the aid of the computer system, can implement a peer-to-peer network, which may enable devices coupled to the computer system to behave as a client or a server.

The CPU 505 can execute a sequence of machine-readable instructions, which can be embodied in a program or software. The instructions may be stored in a memory location, such as the memory 510. Examples of operations performed by the CPU can include fetch, decode, execute, and writeback.

The CPU can be part of a circuit, such as an integrated circuit. One or more other components of the system can be included in the circuit. In some cases, the circuit is an Application Specific Integrated Circuit (ASIC).

The storage unit can store files, such as drivers, libraries and saved programs. The storage unit can store user data, e.g., user preferences and user programs. The computer system in some cases can include one or more additional data storage units that are external to the computer system, such as located on a remote server that is in communication with the computer system through an intranet or the Internet.

The computer system can communicate with one or more remote computer systems through the network 530. For instance, the computer system can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system via the network.

Methods as described herein can be implemented by way of machine (e.g., computer processor) executable code stored on an electronic storage location of the computer system, such as, for example, on the memory or electronic storage unit. The machine executable or machine readable code can be provided in the form of software. During use, the code can be executed by the processor 505. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system can include or be in communication with an electronic display that comprises a user interface (UI) for providing, for example, a display of an image captured by the microscope system. The image can be generated by the imaging light. The image can comprise the currently field-of-view of the microscope system. The image can comprise one or more objects of interest for stimulation by the stimulation light source. Examples of UI's include, without limitation, a graphical user interface (GUI) and web-based user interface.

Example—Simultaneous Calcium Imaging and Optogenetic Manipulation in Freely Behaving Mice Optogenetics has revolutionized systems neuroscience by providing a tool to causally link distinct neurocircuit activity behavior. In addition, advances in calcium indicators and imaging techniques have led to important discoveries on how various internal and external stimuli drive the activity of distinct neuronal populations. Here, we describe two non-limiting examples of lightweight integrated microscopes (FIGS. 8A-B, which illustrate compact optogenetic microscopes having different fluorescence excitation and photostimulation wavelengths) that allow for simultaneous and sequential cellular resolution imaging and optical manipulation within the same field-of-view in freely behaving mice.

Figures 16A, 16B, 16C:
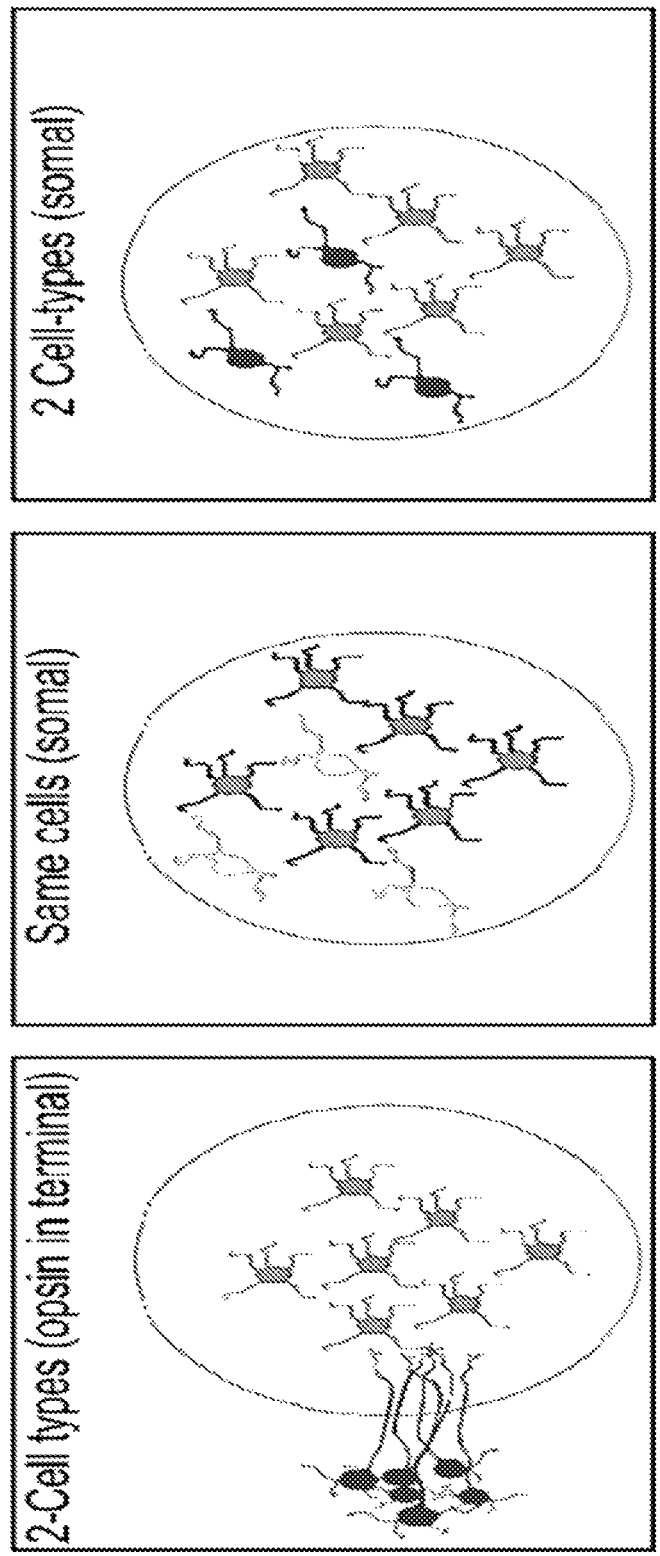
FIGS. 16A-C illustrate non-limiting examples of different imaging applications for a compact optogenetics microscope system.

FIGS. 16A-C illustrates non-limiting examples of different imaging applications for a compact optogenetics microscope system. These integrated microscopes allow for several different imaging and optogenetic applications within the same field-of-view, including modulating presynaptic inputs while imaging postsynaptic cells (FIG. 16A), imaging and modulating the same population of cells (FIG. 16B), and imaging and modulating different populations within the same field-of-view (FIG. 16C).

Figure 17A:
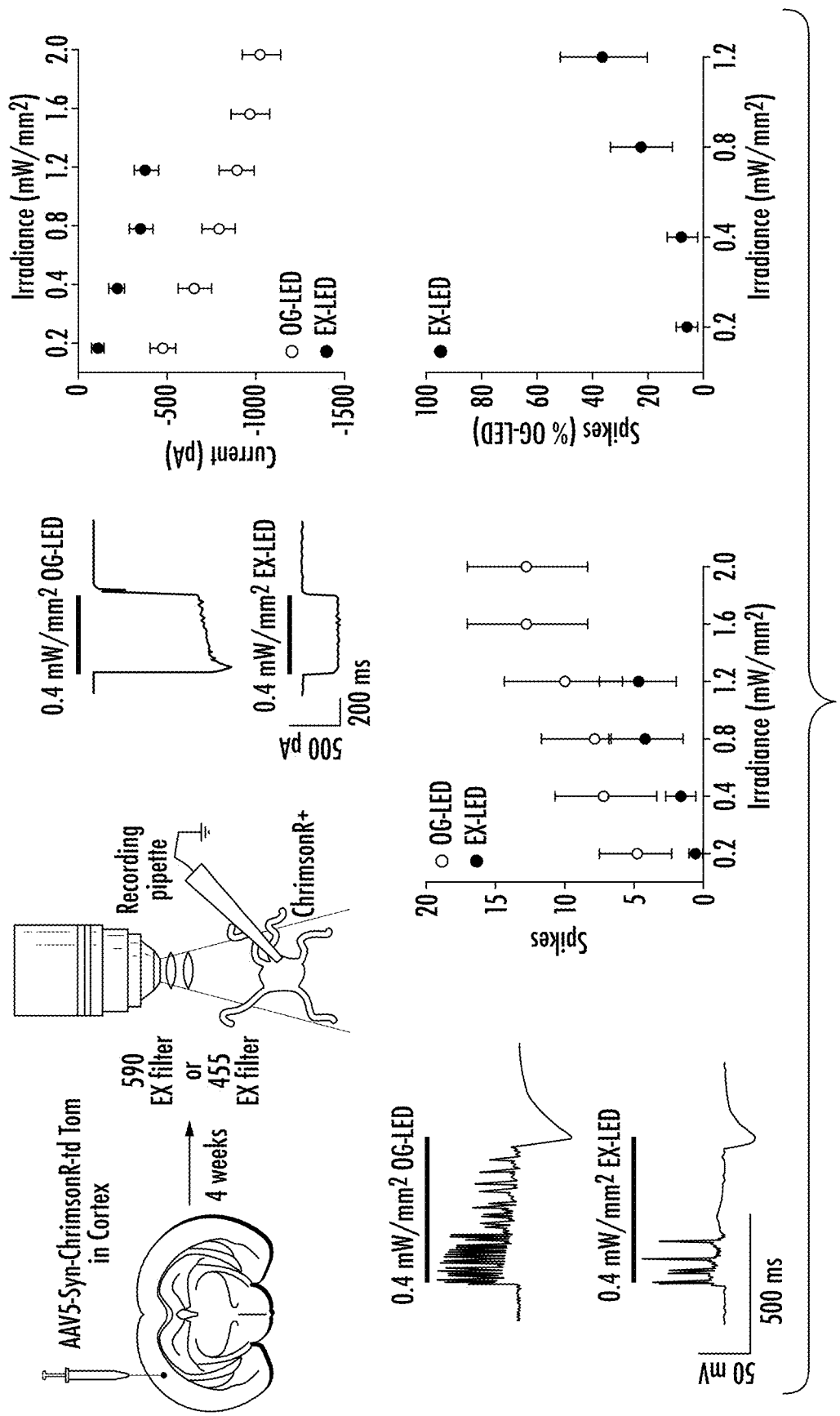
FIG. 17A-D shows examples of data for in vitro characterization of biological crosstalk with excitatory opsins.
Figure 17B:
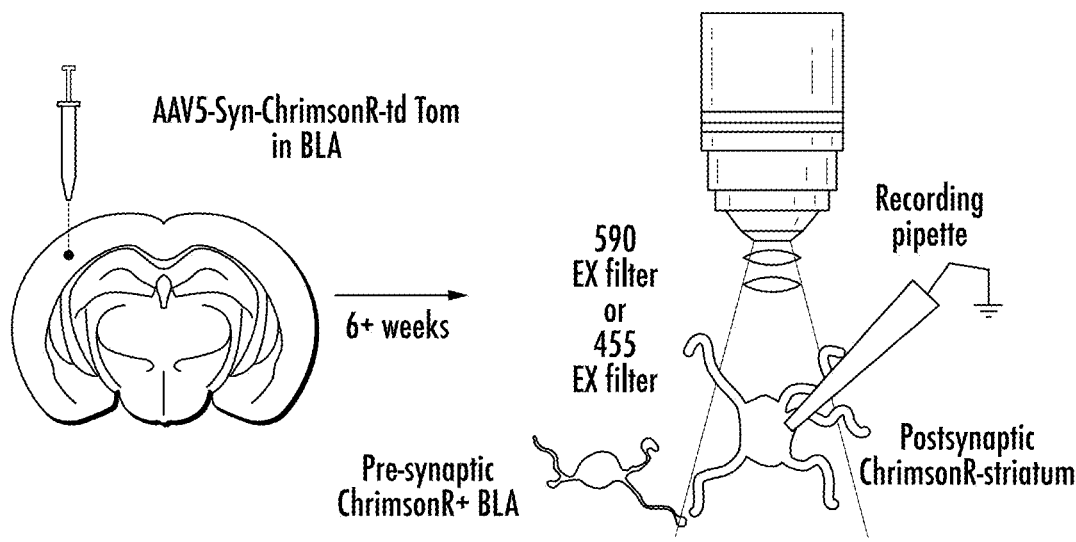
Figure 17B:
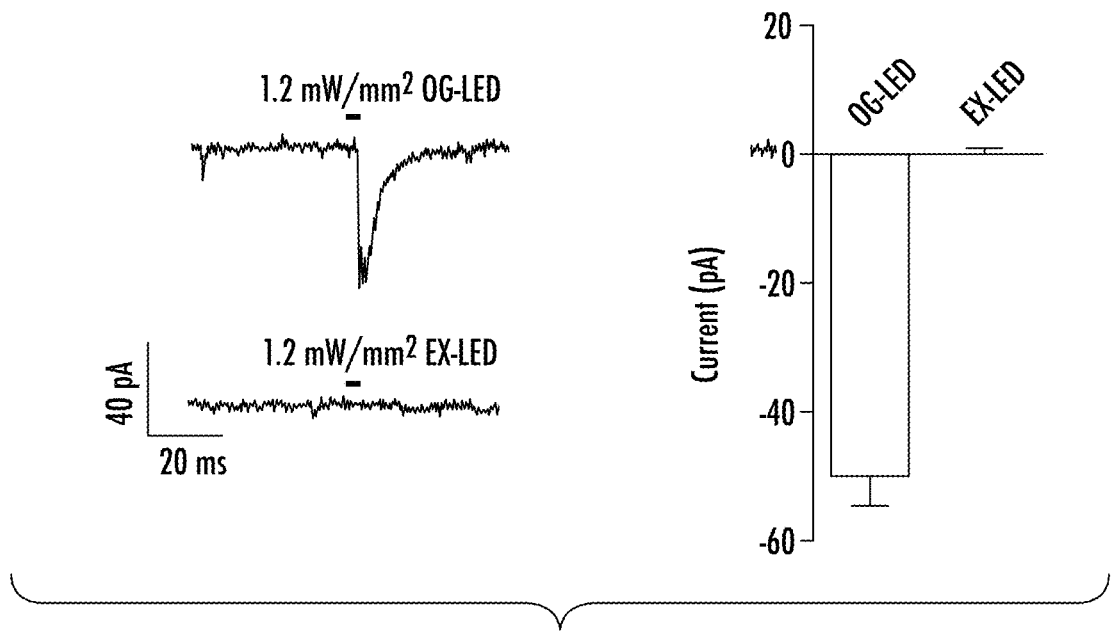
Figure 17C:
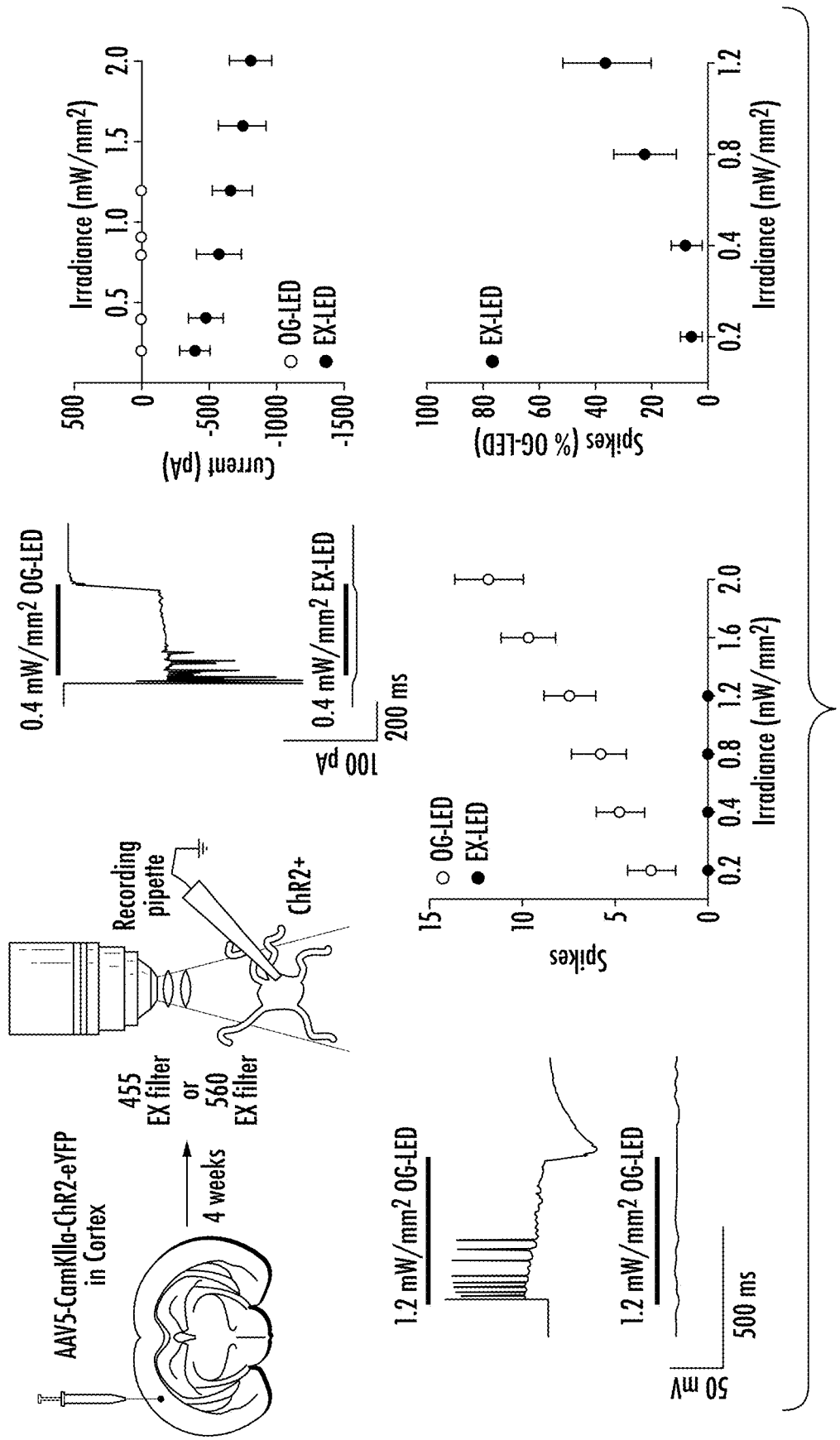
Figure 17D:
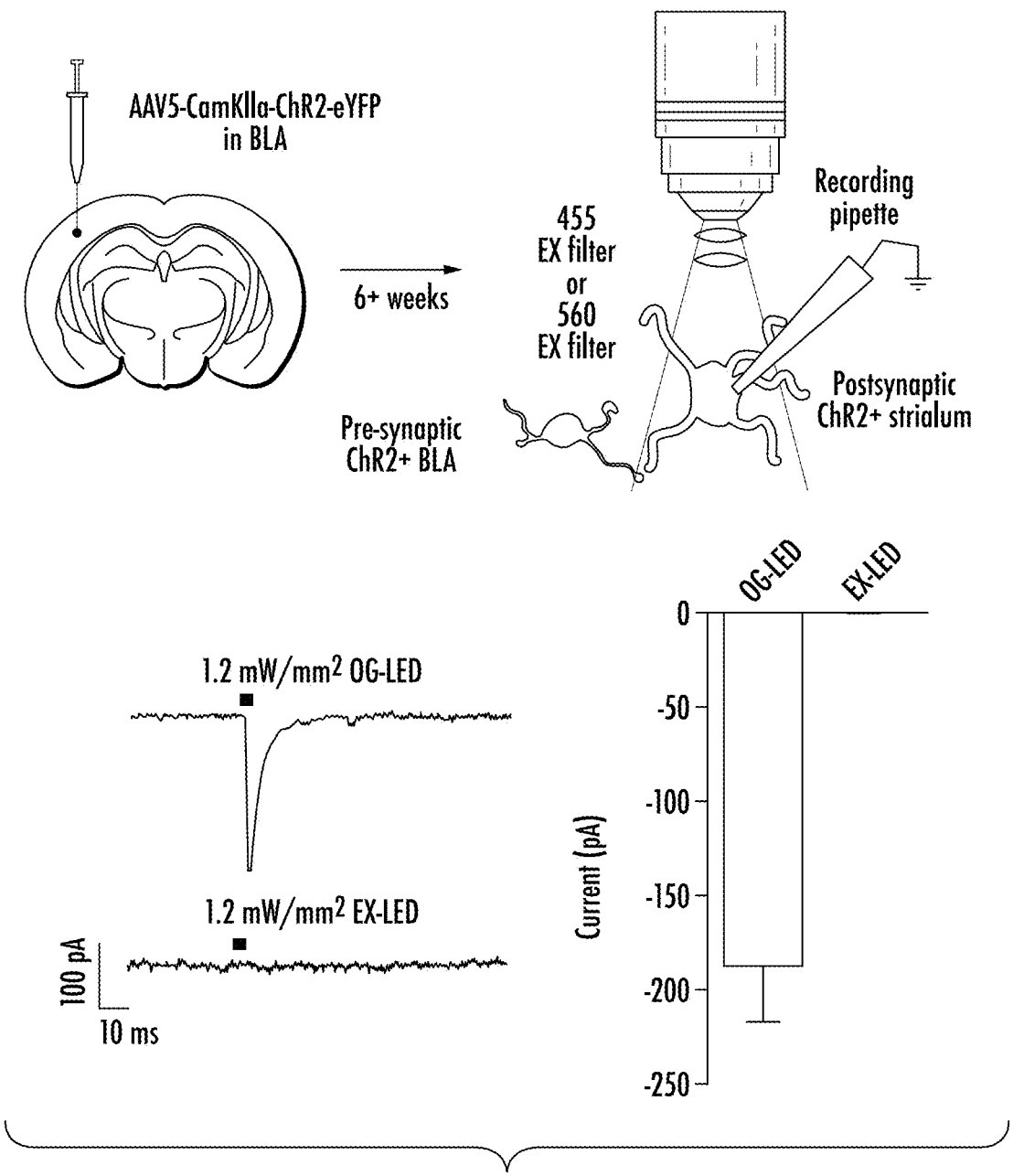

FIG. 17A-D shows examples of data for in vitro characterization of biological crosstalk with excitatory opsins. To determine if the excitation LED light source (EX-LED) activates excitatory opsins, mice were injected with either MVS-Syn-ChrimsonR-tdTom (FIG. 17A, upper left) or MVS-CamKIa-ChR2-eYFP (FIG. 17C, upper left) into the cortex. At 4+ weeks following injection, we performed whole-cell patch-clamp electrophysiology in cortical brain slices (FIGS. 17A and 17C, upper right). We found that blue light filtered with the nVista-OPTO 455EX excitation filter significantly activated ChrimsonR in somas (FIG. 17A, lower left and lower right), but showed no significant activation of ChrimsonR in terminals (FIG. 17B, lower left and lower right) We found that green light filtered with the nVista-OPTO 560EX excitation filter did not significantly activate ChR2 in somas or terminals (FIGS. 17C, lower right, and 17D, lower left and lower right).

Figure 18A:
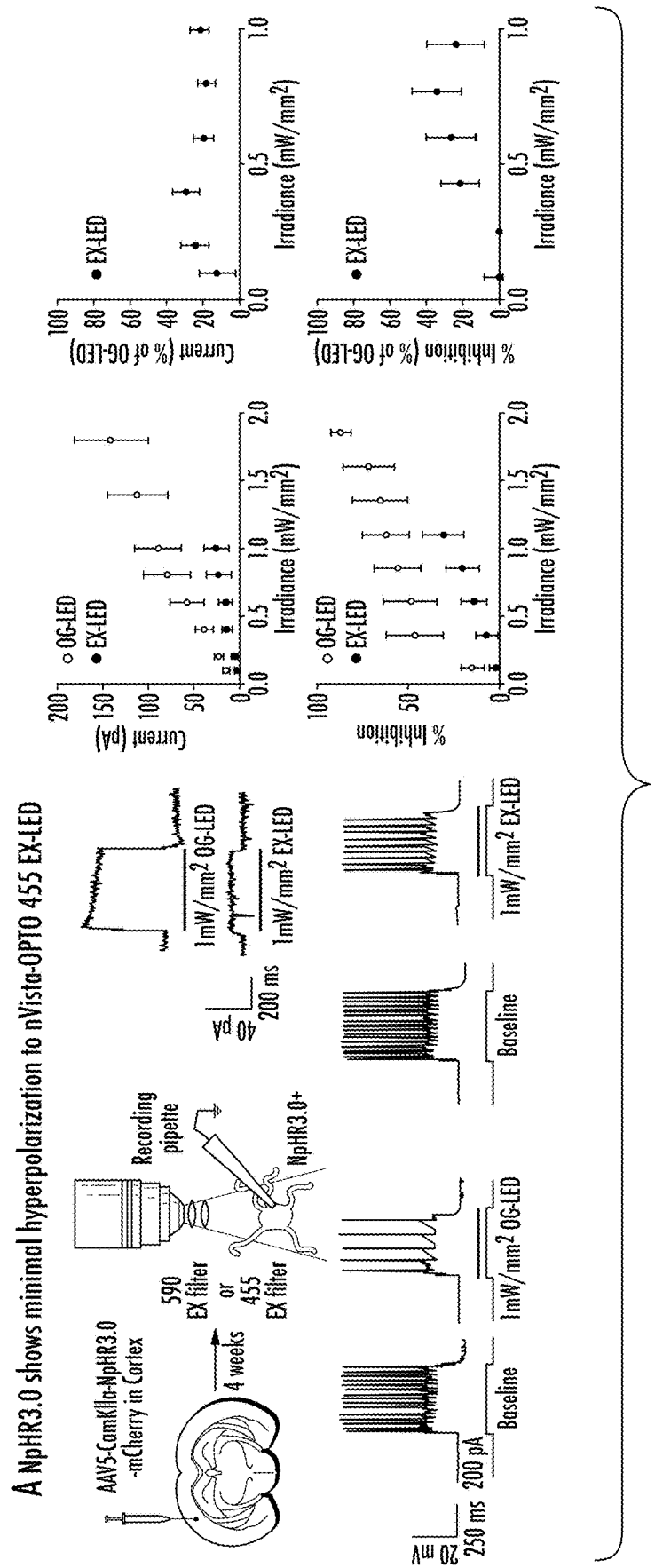
FIG. 18A-B shows examples of data for in vitro characterization of biological crosstalk with inhibitory opsins.
Figure 18B:
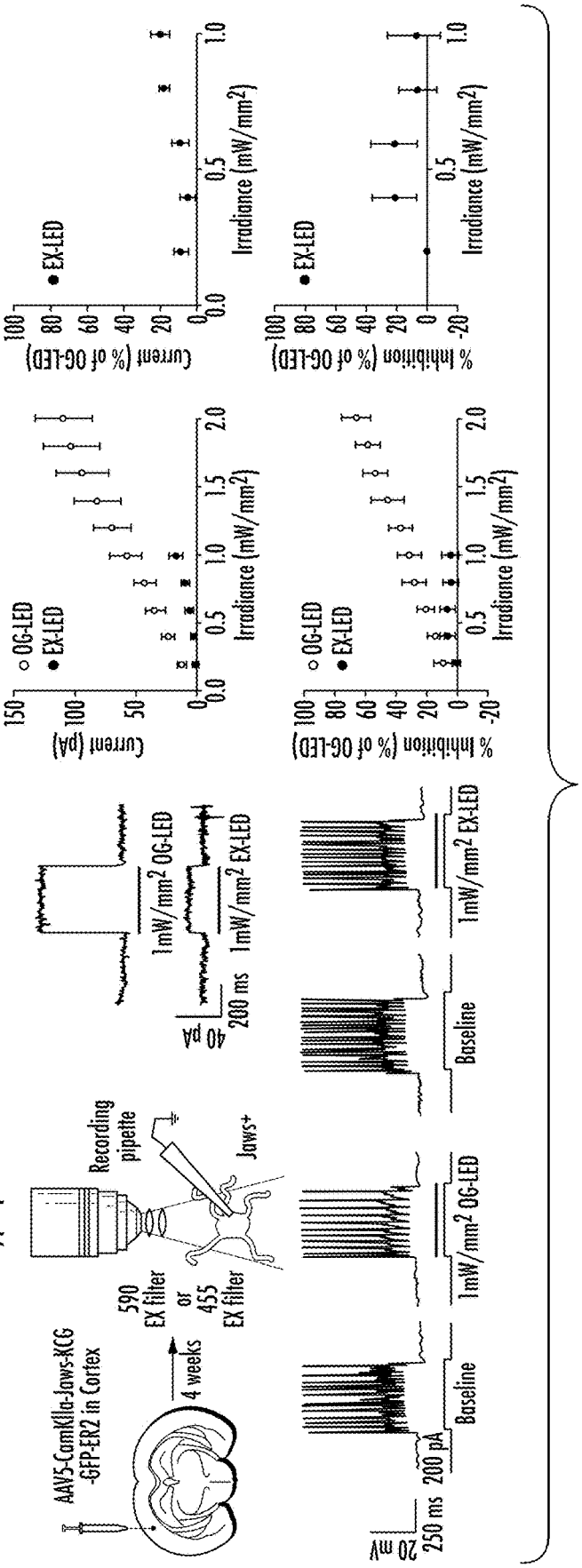

FIG. 18A-B shows examples of data for in vitro characterization of biological crosstalk with inhibitory opsins. To determine if the EX-LED activated inhibitory opsins, mice were injected with either MV5-CamKIIa-NpHR3.0-mCherry (FIG. 18A, upper left) or MV5-CamKII-Jaws-KGC-GFP-ER2 (FIG. 18B, upper left) into the cortex. At 4+ weeks following injection, we performed whole-cell patch-clamp electrophysiology in cortical brain slices. We found that blue light filtered with the nVista-OPTO 455EX excitation filter resulted in some activation of NpHR3.0 (FIG. 18A) and Jaws (FIG. 18B). However, at the lower irradiances used for imaging, this crosstalk was minimal.

Figure 19A:
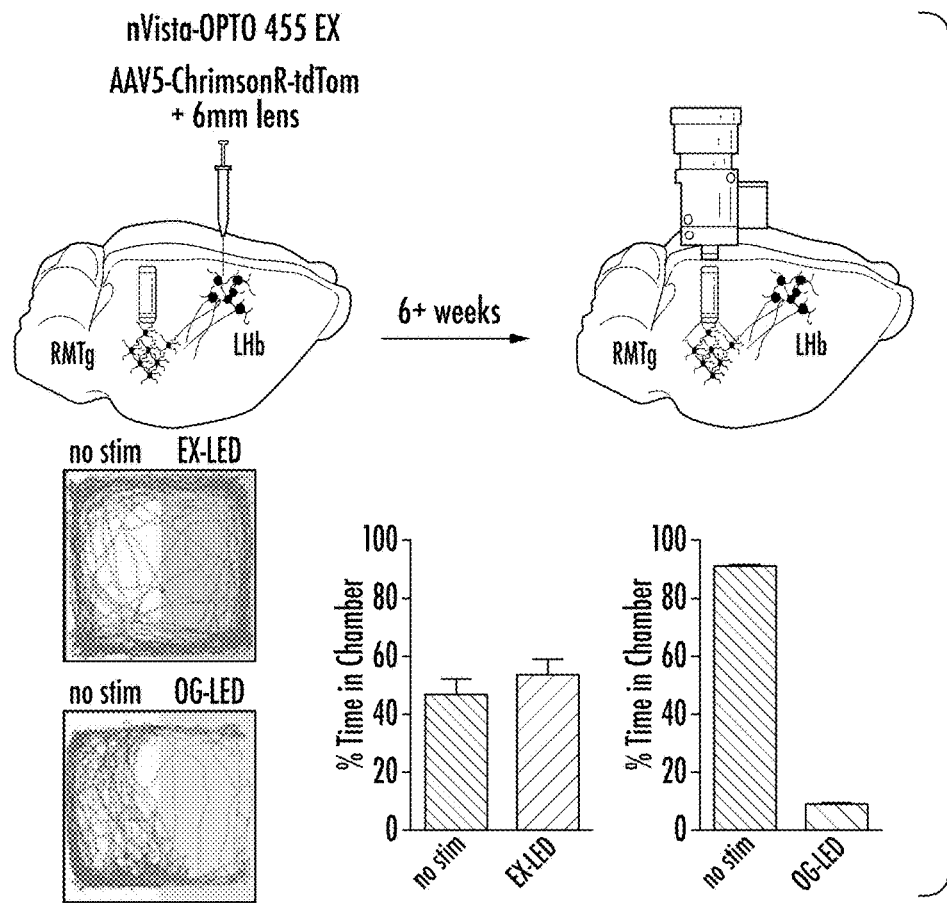
FIGS. 19A-B show examples of data for in vivo characterization of biological crosstalk.
Figure 19B:
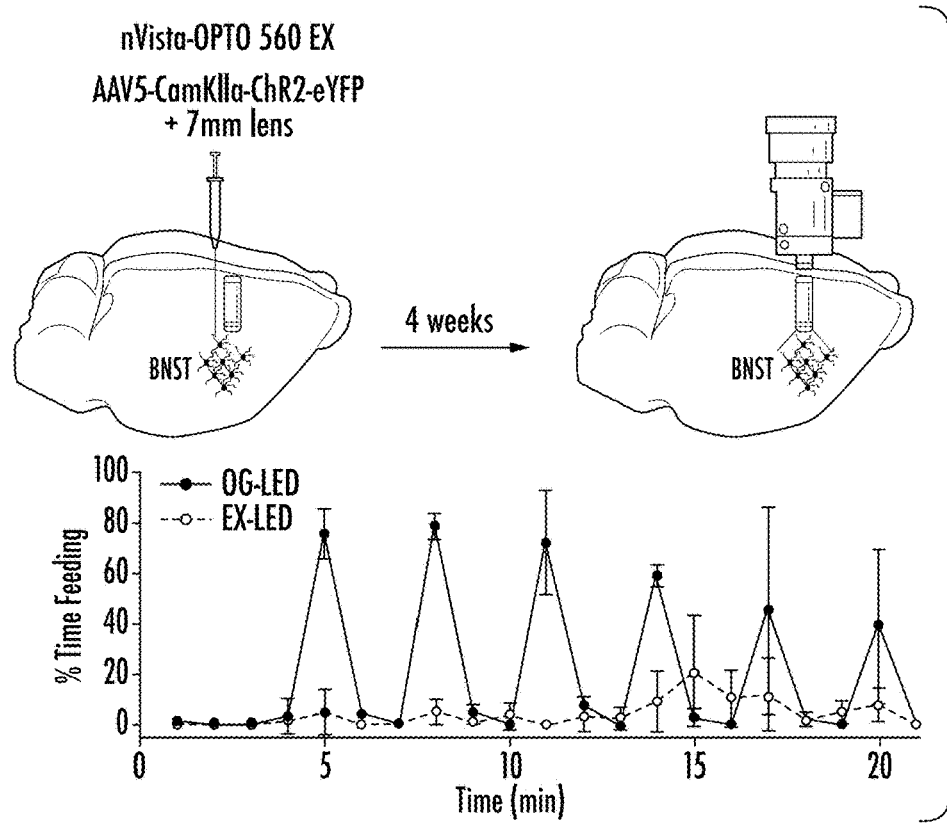

FIGS. 19A-B show examples of data for in vivo characterization of biological crosstalk. We determined if the 1) OG-LED provided enough power to cause the intended behavioral response and 2) if the EX-LED altered behavior. For nVista-OPTO 455EX, mice were injected with AAVS-syn-ChrimsonR-tdTom into the LHb and a 6 mm lens was inserted above the RMTg (FIG. 19A, upper) For nVista-OPTO 560EX, mice were injected with AAV5-CamKIIa-ChR2-eYFP and a 7 mm lens was implanted above the BNST (FIG. 19B, upper). In a real time place preference assay, mice did not show any preference or avoidance to a chamber paired with exposure to EX-LED from the nVista-OPTO 455EX. Mice showed a real time place aversion to a side of a chamber paired with exposure to 60 Hz OG-LED from the nVista-OPTO 455EX (FIG. 19A, lower). In a feeding assay, mice did not show any changes in feeding during exposure to EX-LED from the nVisla-OPTO 560EX. Mice showed increased feeding during exposure to 20 Hz OG-LED from the nVista-OPTO 560EX (FIG. 19B, lower).

Figure 20A:
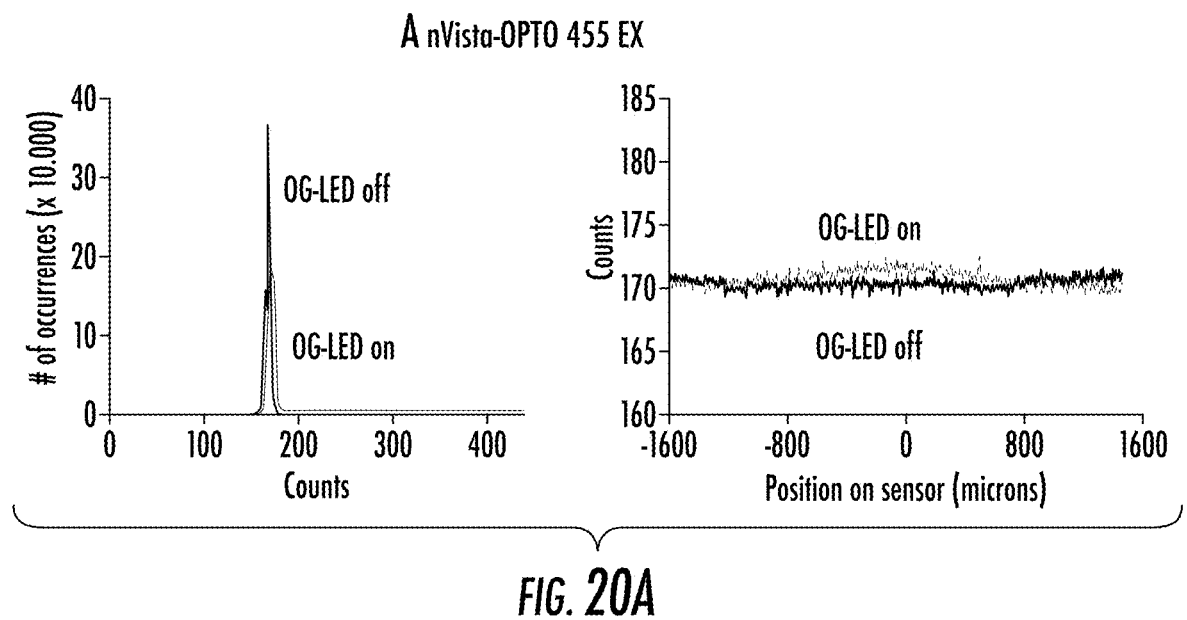
FIGS. 20A-B show examples of data for in vivo characterization of optical crosstalk.
Figure 20B:
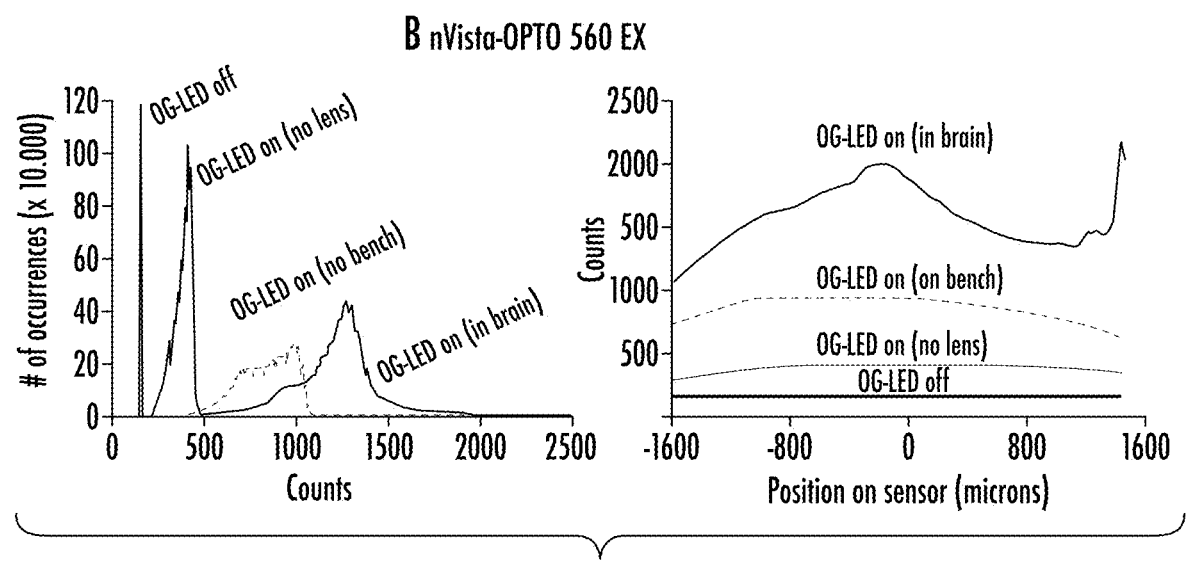

FIGS. 20A-B show examples of data for in vivo characterization of mechanical crosstalk. To determine if the OG-LED excited autofluorescence in the brain tissue, endoscope, or microscope, naive mice (not expressing opsin or indicator), were implanted with 4 mm lenses above the hippocampus or dorsal striatum. Imaging sessions consisted of OG-LED off for 30 s, OG-LED on for 30 s, repeated 3 times. EX-LED was off the entire time. The nVista-OPTO 455EX OG-LED did not activate any autofluorescence in the brain tissue, endoscope or microscope, as evident by no significant change in fluorescent counts between OG-LED on and OG-LED off (FIG. 20A). The nVista-OPTO 560EX OG-LED significantly activated autofluorescence in the microscope, endoscope, and brain tissue, as evident by significantly more counts of fluorescence between OG-LED on and OG-LED off (FIG. 20B).

Figure 21:
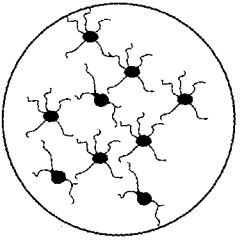
FIG. 21 shows non-limiting examples of suitable opsin/indicator combinations for use with the disclosed compact optogenetic microscope systems.

FIG. 21 shows non-limiting examples of suitable opsin/indicator combinations for use with the disclosed compact optogenetic microscope systems. ChR2 shows minimal in vitro and in vivo crosstalk. RGECO and RCaMP are currently being validated in vivo. Simultaneous GCaMP imaging with somal red-shifted opsin manipulation will require further engineering of red-shifted opsins, such that they are not excited somally by blue light.

Figure 22:
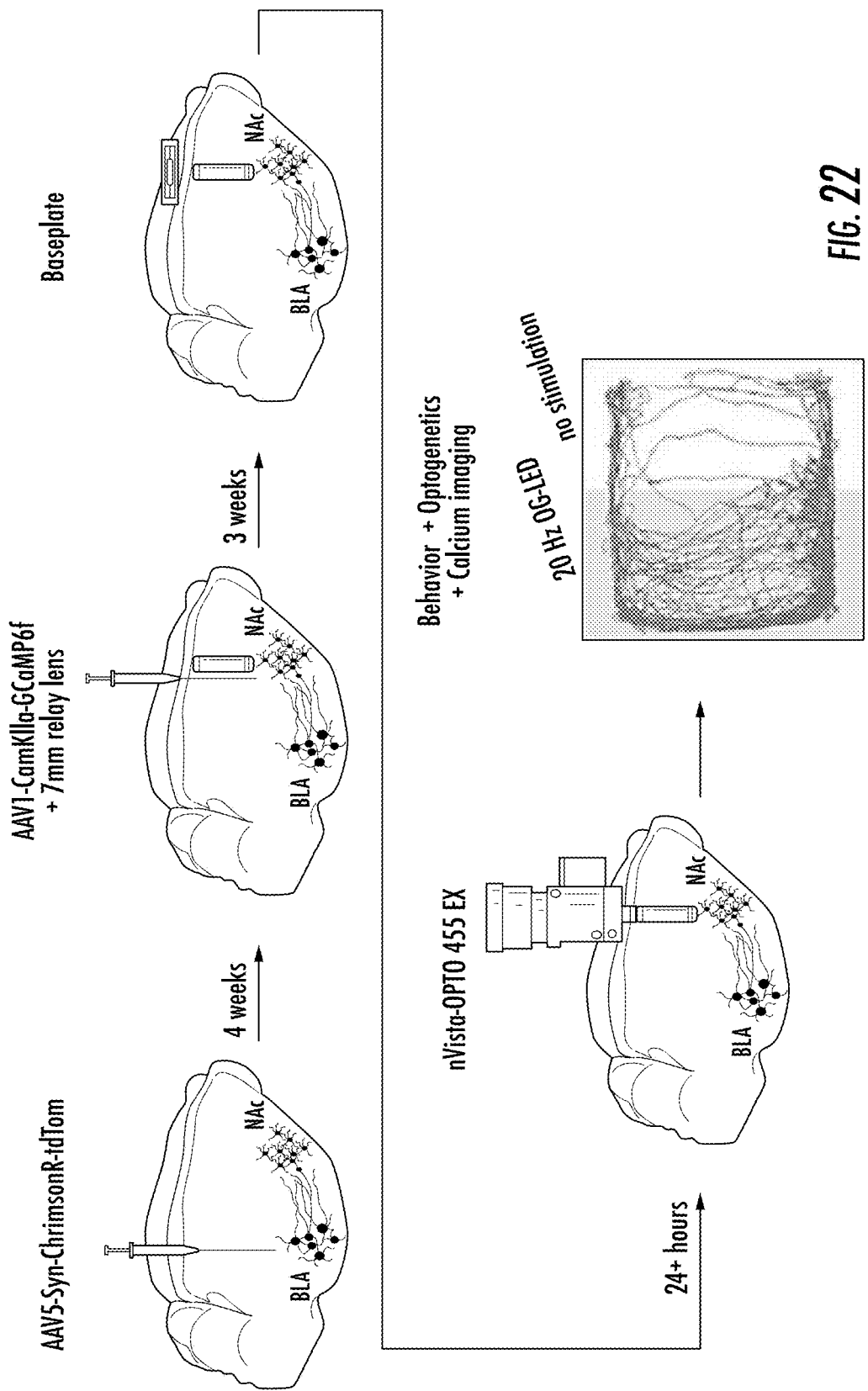
FIG. 22 illustrates one non-limiting example of the steps taken in setting up and performing an optogenetic study using the disclosed compact optogenetic microscope systems.

FIG. 22 illustrates one non-limiting example of the steps taken in setting up and performing an optogenetic study using the disclosed compact optogenetic microscope systems. Mice were injected with AAVS-Syn-ChrimsonR-td-Tom into the BLA. 4 weeks later mice were injected with AAV1-CamKIIa-GCaMP6f into the NAc. In the same surgery, mice were implanted with a 7 mm relay lens above the NAc. Three weeks later mice were implanted with a baseplate that allows for attachment of the nVista-OPTO microscopes. Mice were given access to an open chamber for 20 minutes. If the mouse made a cross into the stimulation-paired side of the chamber, it received is of 20 Hz OG-LED every Ss. If the mouse crossed into the no stimulation-paired side, it received no OG-LED stimulation. Imaging via the EX-LED occurred during the entire 20 minutes. As expected, we found that mice spent more time in the stimulation-paired side of the chamber, demonstrating that the BLA-Io-NAc circuit is rewarding. In addition, we observed an increase in calcium activity that coincided with delivery of the OG-LED.

We have developed two new compact optogenetic microscope systems that allow for imaging and optogenetic manipulation in the same field-of-view in freely behaving animals. We have conducted in vitro and in vivo biological feasibility studies to determine which opsin/indicator combinations are feasible with each microscope. Finally, we have demonstrated simultaneous optogenetic manipulation and calcium imaging in a freely behaving mouse. Combining optogenetics and calcium imaging in an integrated light weight microscope may allow researchers to begin to establish a causal link between neural circuit dynamics and behavior.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An imaging device, comprising:
a) a baseplate configured to be attached to a subject having a target region to be imaged;
b) a removeable and replaceable cable assembly; and
c) a device body having a sensor cap assembly that comprises an image sensor configured to image the target region when the sensor cap assembly is connected to the device body,
wherein the device body is connected to and separated from the baseplate in a tools-free reproducible manner, and
wherein the device body comprises outer spring clips to secure the device body to the baseplate through compression and release of the outer spring clips.

2. The imaging device of claim 1, wherein the baseplate comprises one or more subject attachment mechanism configured to attach the baseplate to the subject to prevent the baseplate from moving relative to the target region.

3. The imaging device of claim 1, wherein the baseplate and device body comprise corresponding mating surfaces that mechanically prevent at least one of
a rotational movement and an axial movement between the baseplate and the device body when the device body is attached to the baseplate.

4. The imaging device of claim 3, wherein the device body comprises one or more V-grooves complementary to one or more bumps in the baseplate configured to have the device body be connected to and separated from the baseplate via kinematic coupling of the device body and the baseplate.

5. The imaging device of claim 4, wherein the one or more V-grooves are positioned to cause the device body to snap to a particular alignment with the baseplate.

6. The imaging device of claim 4, wherein the one or more bumps are evenly spaced.

7. The imaging device of claim 4, wherein the one or more bumps comprise three or four bumps.

8. The imaging device of claim 4, wherein the one or more bumps comprise partial-cylinder bumps.

9. The imaging device of claim 4, wherein the one or more bumps comprise partial-sphere bumps.

10. The imaging device of claim 1, wherein the outer spring clips comprise bent sheet metal clips.

11. The imaging device of claim 1, wherein the outer spring clips comprise molded plastic clips.

12. The imaging device of claim 1, wherein the cable assembly comprises: a cable PCBA, a cap covering cable wires soldered to the cable PCBA, and a threaded collar.

13. The imaging device of claim 12, wherein the threaded collar has an O-ring located inside of it, and wherein the threaded collar is configured to slide down to connect the O ring to and to encapsulate the cap when the cable assembly and the sensor cap assembly are connected to the device body.

14. The imaging device of claim 1, wherein the baseplate comprises shelf-like features extending from at least two edges of the baseplate.

15. The imaging device of claim 1, wherein the sensor cap assembly includes a socket, wherein a header on the cable assembly is dimensioned to plug into the socket.

16. The imaging device of claim 1, wherein the device body has a volume of 10 cubic centimeters or less.

17. The imaging device of claim 1, wherein the device body weighs less than 3 grams.

18. The imaging device of claim 1, wherein the device body has a housing containing one or more optical elements along an image collection pathway from the target region to the sensor cap assembly.

19. The imaging device of claim 1, wherein the baseplate has a hole and the device body has an objective lens configured to fit at least partially through the hole to capture light from the target region when the device body is connected to the baseplate.

20. An imaging device, comprising:
a) a baseplate configured to be attached to a subject having a target region to be imaged;
b) a removeable and replaceable cable assembly; and
c) a device body having a sensor cap assembly that comprises:
an image sensor configured to image the target region when the device body is connected to and separated from the baseplate in a tools-free, reproducible manner, and
a socket;
wherein a header on the cable assembly is dimensioned to plug into the socket.

* * * * *